(12) United States Patent
Christensen et al.

(10) Patent No.: US 8,541,227 B2
(45) Date of Patent: Sep. 24, 2013

(54) CELL COUNTING

(75) Inventors: Nanna K Christensen, Lynge (DK); Jesper Laursen, Allerød (DK); Lars Winther, Smørum (DK)

(73) Assignee: Dako Denmark A/S, Glostrupk (DK)

( * ) Notice: Subject to any disclaimer, the term of this patent is extended or adjusted under 35 U.S.C. 154(b) by 940 days.

(21) Appl. No.: 11/884,247

(22) PCT Filed: Feb. 6, 2006

(86) PCT No.: PCT/IB2006/000613
§ 371 (c)(1),
(2), (4) Date: Aug. 13, 2007

(87) PCT Pub. No.: WO2006/090283
PCT Pub. Date: Aug. 31, 2006

(65) Prior Publication Data
US 2008/0194508 A1 Aug. 14, 2008

Related U.S. Application Data

(60) Provisional application No. 60/656,267, filed on Feb. 25, 2005.

(30) Foreign Application Priority Data

Feb. 25, 2005 (GB) .................................. 0503941.7

(51) Int. Cl.
*C12M 1/34* (2006.01)
*G01N 33/543* (2006.01)
*G01N 31/22* (2006.01)

(52) U.S. Cl.
USPC ..... 435/287.9; 435/7.21; 435/7.24; 435/7.31; 435/7.32; 435/287.2; 436/10; 436/63; 436/172; 436/518; 436/524; 436/528; 436/548; 422/73; 422/408; 422/425; 422/429; 422/430; 422/503

(58) Field of Classification Search
USPC .................. 435/7.21, 7.24, 7.31, 7.32, 287.2, 435/287.9; 436/10, 63, 172, 524, 528, 548, 436/518; 422/56, 73, 99, 82.08, 408, 425, 422/429, 430, 503
See application file for complete search history.

(56) References Cited

U.S. PATENT DOCUMENTS

| 4,110,604 A | 8/1978 | Haynes et al. | |
| 5,039,487 A * | 8/1991 | Smith | ............................. 422/56 |

(Continued)

FOREIGN PATENT DOCUMENTS

| EP | 0 267 724 A1 | 5/1988 |
| EP | 0 321 889 | 6/1989 |

(Continued)

OTHER PUBLICATIONS

Nicholson et al., Evaluation of a Method for Counting Absolute Numbers of Cells with a Flow Cytometer, (Clinical and Diagnostic Laboratory Immunology 4 (3): 309-313 (May 1997).*

(Continued)

*Primary Examiner* — Gail R Gabel
(74) *Attorney, Agent, or Firm* — Finnegan, Henderson, Farabow, Garrett & Dunner, L.L.P.

(57) ABSTRACT

The inventions relates to compositions and method for determining the absolute counts of cells per unit volume of a sample. Such a method comprises: (a) providing a container containing (i) a predetermined quantity of microparticles; and (ii) a cell-binding agent; in which the microparticles are disposed in or on a matrix which adheres to at least one wall of the container such that substantially all the microparticles are thereby attached to the container; (b) adding a known volume of sample to the container; (c) determining the ratio of microparticles to cells by counting microparticles and cells in a volume of the sample; and (d) determining the absolute count of cells by multiplying the number of cells per microparticle by the concentration of microparticles in the sample. Preferably, the matrix retains substantially all the microparticles in or on the container during routine handling, including inversion, of the container, in the absence of mechanical retaining means such as a retainer grid in the container.

29 Claims, 52 Drawing Sheets

Dual 1 Matrix

(56) References Cited

U.S. PATENT DOCUMENTS 5,627,037 A * 5/1997 Ward et al. .................. 435/7.21
5,723,218 A 3/1998 Haugland et al.

FOREIGN PATENT DOCUMENTS

| EP | 0 470 810 | 2/1992 |
|---|---|---|
| EP | 0 470 810 A1 | 2/1992 |
| WO | WO 02/32398 A2 | 4/2002 |

OTHER PUBLICATIONS

Schnizlein-Bick et al., "Evaluation of TrucCount absolute count tubes for determining CD4 and CD8 cell numbers in human immunodeficiency virus-positive adults", Clin. and Diagnostic Lab. Immunology, American Society for Microbiology, vol. 7, No. 3, May 2000, pp. 336-343.

Reimann et al., "Multisite comparison of CD4 and CD8 T-Lymphocyte counting by single-versus multiple-platform methodologies: Evaluation of Beckman Coulter flow-count fluorospheres and the tetraONE system", Clin. and Diagnostic Lab. Immunology, American Society for Microbiology, vol. 7, No. 3, May 2000, pp. 344-351.

Jani et al., "Affordable CD4+ T cell counts by flow cytometry II. The use of fixed whole blood in resource-poor settings", Jour. Immunological Methods, Elsevier, vol. 257, No. 1-2, Nov. 2001, pp. 145-154.

Anonymous, "BD Trucount Tubes" [online], [retrieved on Aug. 10, 2007], Retrieved from the Internet: <URL: http://www.bdbiosciences.com/external_files/is/doc/tds/Package_Inserts_CE/live/Web-enabled/23/3483-05-340334-PI-CE-usen.pdf>.

Nicholson, Janet K.A, et al. (1997) Evaluation of a Method for Counting Absolute Numbers of Cells with a Flow Cytometer, Clinical and Diagnostic Laboratory Immunology, 4: 309-313.

British Search Report, dated Aug. 30, 2005, for counterpart application No. GB0503941.7.

* cited by examiner

Control

Control

Matrix

Matrix

FITC Control

FITC Matrix

RPE Control

RPE Matrix

RPE-Cy5 Control

RPE-Cy5 Control

APC Control

APC Control

Dual 1 Control

Dual 1 Matrix

Dual 2 Control

Dual 2 Matrix

Dual 3 Control

Dual 3 Matrix

Dual 4 Control

Dual 4 Matrix

CDC3 FITC

CDC3 RPE

CDC3 RPE-Cy5

CDC3 APC

CD3-FITC/CD4-FITC

CD3-APC/CD4-APC

CD3-PB

CD4-RPE/CD8-RPE

CD3 RPE-A680 Day 0

CD3 RPE-A680 Day 8

CD4 FITC Day 0

CD4 FITC Day 8

Control

Matrix

Control

Matrix

CELL COUNTING

CROSS REFERENCE TO RELATED APPLICATIONS

This application is the United States National Stage of International Application PCT/IB2006/000613, filed 6 Feb. 2006 and designating the United States of America, which claims the benefit of the filing date of and right of priority to U.S. Provisional Application No. 60/656,267, filed 25 Feb. 2005 and to United Kingdom application 0503941.7, filed 25 Feb. 2005, all such applications hereby incorporated by reference in their entirety.

FIELD

This invention relates to the fields of diagnosis, assays, standardisation and enumeration of particles, in particular cells. In particular, the invention relates to methods and compositions for identifying the concentration or "absolute count" (cells per unit volume) of one or more cell types in a sample.

BACKGROUND

Human immunodeficiency virus type 1 (HIV-1) infects cells that express the CD4 receptor (De Wolf et al., 1988, *AIDS Res Hum Retroviruses* 1988; 4:433-440) and, as a result, depletes its host of CD4 lymphocytes (Lang et al., 1989, *J Acquir Immune Defic Syndr* 1989; 2:63-69). This depletion of CD4 T lymphocytes has been linked to the immunopathogenesis of HIV infection and progression of the disease (Fahey et al., 1990, *N Engl J Med* 1990; 322:166-172; Masur, 1989, *Ann Intern Med* 1989; 111:223-231).

A CD4 count of <=200 cells/µl has been included as an AIDS-defining event (Centers for Disease Control. 1992B, *Morbid Mortal Weekly Rep* 1992; 41(RR-17):1-35), as these measurements are useful predictors for the onset of opportunistic diseases such as *Pneumocystis carinii* pneumonia (Centers for Disease Control. 1992A, *Morbid Mortal Weekly Rep* 1992; 41(RR-4):1-11). With the advent of highly active antiretroviral therapy, CD4 T-lymphocyte measurements have been used to monitor immune reconstitution (Autran et al., 1997, Science 1997; 277:112-116).

The current predicate methodology for determining absolute CD4 T-lymphocyte counts is dependent upon immunophenotypic identification of cells with fluorescently labelled monoclonal antibodies directed against the CD4 antigen. Relative percentages of CD4 T cells are determined with a flow cytometer. An absolute CD4 count is derived by multiplying the percentage of lymphocytes that are CD3+ CD4+ by the absolute lymphocyte count determined with a hematology instrument.

However, the overnight shipment of blood may result in increased intrinsic variability in the absolute lymphocyte count depending on the hematology instrument that is used (Koepke and Landay 1989, *Clin Immunol Immunopathol* 1989; 52:19-2; Paxton et al., 1993, *Ann N Y Acad Sci* 1993; 677:440-443). Therefore, the absolute CD4 count in overnight samples may have increased variability due solely to the hematological determinants.

Thus, the determination of the "absolute count" of a cell type, i.e., the number of cells in a given volume (concentration), is an important consideration in the general field of cytometry and the field of HIV diagnosis and monitoring in particular.

U.S. Pat. No. 4,110,604 describes a method and apparatus for determining the concentration of particles in a fluid, for example, platelets, through use of a second "reference" particle suspended in the fluid (e.g., red blood cells). The "reference" particle differs in a physical characteristic, for example, electrical impedance, from the particle of interest and is present at a predetermined or determinable concentration or density. The number of red blood cells is counted, as is the number of platelets. Then, by knowing or determining the number of red blood cells in a given unit of volume, an equation can be used to arrive at the number of platelets in the same unit volume. Alternatively, a reference particle could be included in the sample at a known concentration, and then the reference particle is counted along with the platelets. By knowing the concentration of reference particles, it is possible to determine the concentration of platelets.

Such a system as described in U.S. Pat. No. 4,110,604 discriminates between the particles based on their physical characteristics, and is not amenable for use to distinguish between two subpopulations of the same cell type, for example $CD3^+$ $CD4^+$ and $CD3^+$ $CD8^+$ cells. Use of flow cytometry and cell binding agents (capable of binding to cell markers) partially overcomes this problem. Thus, the need for precise and reproducible monitoring of CD4 T-lymphocyte levels in HIV-infected patients has led several companies to develop simpler methods for measuring absolute CD4 and CD8 T-lymphocyte counts (Bene et al., 1998; Denny et al., 1995; Nicholson et al., 1994; O'Gorman, et al., 1997; Paxton, et al., 1995).

European Patent EP 0470810 describes a method for determining the absolute counts of a cell population within a sample by means of flow cytometry. The method makes use of a tube. The tube may comprise a diluent, and the sample is added to the tube containing the diluent. The diluent is said to comprise a solution of isotonic buffer such as phosphate buffered saline, one or more cell markers capable of labelling cells in the population of interest, a fixative such as paraformaldehyde, and a known number of fluorescent microparticles.

The specification of EP 0470810 specifically envisages that the tube may be coated with blocking agents such as bovine serum albumin, caesin or gelatin to prevent adhesion of the components of the diluent to the tube walls, and that these blocking agents may be coated on and dried in the tube using a preservative such as trehalose.

In the method described in EP 0470810, the sample is added to the tube, and the cells are allowed to be labelled with the cell markers. A fluorescence trigger is set to include essentially all the microparticles and cells, and one or more fluorescence gates are set to distinguish between these. The number of cells which meet or exceed the fluorescence trigger are counted, and the number of cells per microparticle for each fluorescence gate is multiplied by the known concentration of microparticles to arrive at the absolute count of cells per unit volume. Thus, knowledge of the number of cells for any population and number of microparticles provides a ratio. Knowing the number of microparticles per unit volume and then multiplying by the first ratio provides the number of cells in a population per unit volume, i.e., the absolute count of the cells.

However, the method described in EP 0470810 makes use of tubes containing a large volume of diluent, which results in certain disadvantages. The diluent present in the tubes described in EP 0470810 necessitates prolonged incubation time and higher amounts of the cell-binding agents (and thus higher cost). Furthermore, the presence of the diluent impedes efficient lysing of the erythrocytes. Erythrocyte lysing is a procedure recommended by the Centres for Disease Control and Prevention (CDC), The European Working Group on Clinical Cell Analysis (EWGCCA) and The British Committee for Standards in Haematology (BCSH) for enumeration of CC3-CD4 positive cells.

The percentage of CD4+ cells out of the total lymphocyte population cannot be determined using the method described in EP 0470810 since there is no marker for total lymphocytes included. This is crucial in paediatric patients where a CD4 count is not sufficient for monitoring disease progression. Children under the age of 5 have higher levels of CD4 positive lymphocytes than adults and thus a percentage of CD4+ cells out of the total lymphocytes is necessary for determining whether treatment should be initiated. Close monitoring of HIV infection is of particular importance in children, since the infection can actually be cured in very young patients.

Finally, the large volume of the diluent means that the tubes described in EP 0470810 are not easily adapted for manufacture as a disposable component, leading to a higher price.

Disposable containers for absolute cell counting are known in the art. Such containers comprise dispensed portions or aliquots containing a known, fixed number of microparticles per tube. Knowledge of the number of microparticles and, crucially, maintenance of this number within the tube during handling (e.g., prior to and during addition of the sample), is essential to the accuracy of the counts obtained.

It is known for example, to employ disposable containers containing a pre-determined number of microparticles. For example, a commercially available counting system comprises BD TruCOUNT Tubes (Catalog No. 340334, BD Biosciences San Jose, Calif.). TruCOUNT absolute-count tubes contain a lyophilised pellet that dissolves during sample preparation, releasing a known number of fluorescent beads. The tube comprises a stainless steel retainer in the form of a grid which is positioned near the closed end of the tube and above the lyophilised pellet. The stainless steel retainer prevents the lyophilised pellet from falling out of the container during routine handling (such as for example, inversion or shaking of the tube), and accordingly maintains the fixed predetermined number of microparticles in the tube.

Nevertheless, problems remain with such embodiments. These generally arise from the fact that the lyophilisation results in a pellet, which is "fluffy" and easily breaks up from handling. Specifically, it is crucial to avoid disturbing the lyophilised pellet during sample handling and addition. Thus, the operating instructions for the TruCOUNT tubes specifically caution against disturbing the steel retainer and the pellet containing the beads, and advise pipetting above the stainless steel retainer. Furthermore, depending on the pitch of the stainless steel grid, it may not be totally effective in preventing portions of the lyophilised pellet from being detached and falling out of the tube. In order to minimise disturbance to the lyophilised pellet and grid, the TruCOUNT tubes have to be packaged in a protective pouch in a controlled atmosphere. Once the protecting pouch has been opened, the pellet will absorb moisture and consequently shrink. When this happens, the pellet is at risk of falling through the grid. Thus, when any of the tube, the pellet or grid is disturbed, or portions are lost, the absolute count obtained is potentially subject to error. The operating instructions for the TruCOUNT tubes state that the tubes should be discarded if the pellet has been disturbed in any manner.

Other problems arise from the nature of the beads employed in the TruCOUNT tubes. These give a very small forward scatter signal on the flow cytometer, and therefore the beads are seen in the same area as debris from lysed erythrocytes or unlysed erythrocytes. This means that it is not possible to use a trigger on the forward scatter parameter since this would either include both beads and debris/erythrocytes or exclude both. Instead a fluorescence trigger has to be used, which is a disadvantage, as some users prefer to use a scatter trigger instead of a fluorescence trigger.

Furthermore, methods of absolute counting which employ microbeads need to be carefully optimised to maintain the precision and consistency (i.e., count to count variability) of counts. One primary problem is that not all beads in the mixed sample may be counted, i.e., the actual number of beads counted with the flow cytometer is lower than expected from the predetermined number present in the tube. This arises due to the tendency of microparticles to adhere to one another to form doublets, triplets, quadruplets, etc. This is a particular problem with the beads used in the TruCOUNT tubes described above, in which (depending on batch) there is usually 5-10% multiple beads in a tube. Although this can be accounted for in the bead value quoted, it may give rise to discrepancies in the absolute counts.

In addition to adhering to one another, microparticles also tend to adhere to the surface of the container. Finally, some particles are not registered by the flow cytometer due to dead time in the sample acquisition. These factors compound to cause a discrepancy between the number of beads applied to the flow cytometer and the number of beads registered by the detectors of the flow cytometer in prior art methods.

A further problem is inter-count variability, i.e, the consistency of counts obtained through repeated processing. In other words, it is of the outmost importance that the variation in count between identical samples is low, i.e. one obtains a similar count every time a particular sample is measured. Here, the primary cause of the non-reproducibility appears to be microparticles adhering to the walls of the container in variable numbers.

The primary cause of this is the "stickiness" of the microparticles, i.e., the tendency of the microparticles to adhere to other components. This appears to be dependent on the nature of the material from which the microparticles are made, and the conditions in the environment in which they are counted. Variables such as pH, ionic strength, hydrophobicity and temperature of the sample medium can and do cause microparticles to have increased adhesiveness. Coating the walls of the container with for example BSA can reduce but not completely eliminate the problem. Multiplying the count obtained with a correction factor to account for the "lost" beads may also help reduce the discrepancy.

Nevertheless, it is clear that there are problems in the prior art, which have the potential to reduce the precision and accuracy of the absolute counts.

SUMMARY

In order to solve the problems inherent in the prior art, we herein disclose the encapsulation of microparticles within an embedding medium, or "matrix", as a means to retain the microparticles within a container.

According to a $1^{st}$ aspect of the present invention, we provide a method for determining the absolute counts of cells per unit volume of a sample, the method comprising: (a) providing a container containing: (i) a predetermined quantity of microparticles; and (ii) a cell-binding agent; in which the microparticles are disposed in or on a matrix which adheres to at least one wall of the container such that substantially all the microparticles are thereby attached to the container; (b) adding a known volume of sample to the container to release microparticles from said wall; (c) determining the ratio of microparticles to cells by counting microparticles and cells in a volume of the sample; and (d) determining the absolute count of cells by multiplying the number of cells per microparticle by the concentration of microparticles in the sample.

Preferably, the matrix retains substantially all the microparticles in or on the container during routine handling of the container. In various embodiments, the microparticles are retained when the container is inverted.

Preferably, the microparticles are retained in the absence of other, preferably mechanical, retaining means.

Preferably, the microparticles are retained in the absence of a retainer grid in the container.

In some embodiments, the matrix comprises a carbohydrate, preferably a sugar or a mixture of sugars, a polymer or a protein.

Preferably, the matrix comprises a 1:2, 1:1 or 2:1 mixture of any two of fructose, trehalose and raffinose. Preferably, the matrix comprises a 1:1 mixture of fructose: trehalose.

Preferably, the matrix is present at a quantity of less than 5 mg, preferably 3 mg or less. Preferably, the matrix contains an anti-oxidant; preferably, the antioxidant comprises butylated hydroxytoluene (BHT).

In a some embodiments, substantially all microparticles are released into the sample volume on addition of sample. Preferably, substantially all microparticles are discrete when counted. Preferably, the microparticles do not substantially form doublets or multiplets when counted.

In other embodiments, following addition of sample, preferably during counting of microparticles, the microparticles do not form doublets.

Preferably, the cells and microparticles are counted in a flow cytometer.

In one embodiment, the cells comprise micro-organisms, preferably yeast or bacteria.

In another embodiment, the cells comprise lymphocytes and/or the sample comprises unlysed whole blood. The cell-binding agent may comprise an antibody, preferably a monoclonal antibody, capable of binding to an antigen selected from the group consisting of: CD2, CD3, CD4, CD5, CD7, CD8, CD10, CD13, CD14, CD15, CD16, CD19, CD20, CD22, CD33, CD34, CD38, CD45, CD56, CD57, CD64, CDw65, CD117 and CD133.

Preferably, the matrix and microparticles are deposited on a wall of the container through at least partial removal of solvent from a suspension of microparticles in an aqueous solution of matrix, preferably by evaporation of solvent.

The microparticles may comprise polystyrene, latex, agarose or acrylamide beads, preferably polystyrene beads.

Preferably, the microparticles and the cell-binding agent are independently detectable by virtue of comprising a signal generating means, preferably a fluorescent signal generating means. Preferably, the fluorescent signal generating means comprises a fluorochrome selected from the group consisting of: fluorescein isothiocyanate (FITC), phycoerythrin (PE), PE-CY5, PE-CY5.5, PE-CY7, PE-A680, PE-TR (TEXAS RED), allophycocyanin (APC), APC-CY7, PACIFIC BLUE, CASCADE YELLOW, coumarines, ALEXA dyes or Q-DOTS.

In some embodiments, the microparticles and the cell-binding agent are labelled with different fluorochromes.

In some embodiments, the container may comprise more than one cell-binding agent.

For example, the container may comprise an anti-CD3 antibody coupled to phycoerythin, an anti-CD4 antibody coupled to APC and an anti-CD45 antibody coupled to FITC. Alternatively, or in addition, the container may comprise an anti-CD34 coupled to phycoerythin, an anti-CD45 coupled to FITC or APC.

Alternatively, or in addition, the container may comprise an anti-CD3 antibody coupled to PACIFIC BLUE, an anti-CD4 antibody coupled to FITC, an anti-CD8 antibody coupled to APC, an anti-CD19 antibody coupled to RPE-CY5, an anti-CD45 antibody coupled to CASCADE YELLOW and an anti-CD56 antibody coupled to RPE.

Alternatively, or in addition, the container may comprise propidium iodide and TWEEN. Preferably, the container is disposable.

There is provided, according to a $2^{nd}$ aspect of the present invention, a composition comprising (a) a predetermined quantity of microparticles; and optionally (b) a cell-binding agent; in which the microparticles are disposed in or on a matrix which is capable of adhering to at least one wall of the container such that substantially all the microparticles are thereby attached to the container.

Preferably, the composition is suitable for determining the absolute counts of cells of a sample.

The composition may further comprise one or more features as defined in the $1^{st}$ aspect of the invention.

We provide, according to a $3^{rd}$ aspect of the present invention, a container comprising a composition according to the $2^{nd}$ aspect of the invention, in which the matrix adheres to the container.

As a $4^{th}$ aspect of the present invention, there is provided use of a composition according to the $2^{nd}$ aspect of the invention, or a container according to the $3^{rd}$ aspect of the invention, for determining the absolute counts of cells per unit volume of a sample.

We provide, according to a $5^{th}$ aspect of the present invention, a method for producing a composition according to $2^{nd}$ aspect of the invention, comprising: (a) providing a solution or suspension of microparticles, a matrix and optionally a cell-binding agent; and (b) removing at least a portion of solvent from said suspension preferably by evaporation of solvent.

The method may further comprise one or more features as defined in the $1^{st}$ aspect of the invention.

The present invention, in a $6^{th}$ aspect, provides a method for producing a container according to the $3^{rd}$ aspect of the invention, comprising: (a) providing a container containing a solution or suspension of microparticles, a matrix and optionally a cell-binding agent; and (b) removing at least a portion of solvent preferably by evaporation of solvent from said suspension to deposit the matrix, cell-binding agent and microparticles on a wall of the container.

In a $7^{th}$ aspect of the present invention, there is provided a kit for determining the absolute counts of cells in a sample comprising a composition according to the $2^{nd}$ aspect of the invention or a container according to the $3^{rd}$ aspect of the invention, and optionally instructions for use.

Preferably, the cells comprise CD3+ CD4+ cells.

Preferably, we provide such a kit for the detection, diagnosis or monitoring of HIV infection or the diagnosis of AIDS.

According to an $8^{th}$ aspect of the present invention, we provide a method comprising determining a first absolute count of a cell type at a first time point by a method according to the $1^{st}$ aspect of the invention, and determining a second count of the cell type at a second time point.

Preferably, the second count is an absolute count of the cell type at the second time point determined by a method according to the $1^{st}$ aspect of the invention.

Preferably, the samples are from the same individual, preferably the same organ or tissue of an individual.

We provide, according to a $9^{th}$ aspect of the invention, a method comprising determining a first absolute count of a first cell type by a method according to the 1$^{st}$ aspect of the invention, and determining a second count of a second cell type.

Preferably, the second count is an absolute count of the second cell type determined by a method according to the 1$^{st}$ aspect of the invention.

Preferably, the samples are from the same individual, preferably the same organ or tissue within an individual.

Alternatively, or in addition, the samples are from different individuals within a population or cohort.

In some highly advantageous embodiments, the first and second counts are compared to provide information about the status of the sample or each sample, or the status of the tissue, organ, organism, cohort or population or of each tissue, organ, organism, cohort or population from which the sample(s) is (are) derived.

The status may be selected from the group consisting of: health status, nutritional status, mental status, propensity to disease, presence or absence of disease, presence or absence of latent infection, preferably HIV infection.

Preferably, the cell type or the first cell type comprises CD4+ lymphocytes. Preferably, the cell type or the second cell type comprises total lymphocytes in the same sample. Preferably, the infection comprises HIV infection and/or the disease comprises AIDS.

There is provided, in accordance with a 10$^{th}$ aspect of the present invention, a composition comprising a 1:1 mixture of fructose: trehalose together with a predetermined quantity of microparticles and optionally a cell-binding agent.

As an 11$^{th}$ aspect of the invention, we provide a method comprising: (a) providing a container containing a predetermined quantity of microparticles disposed in or on a matrix which adheres to at least one wall of the container such that substantially all the microparticles are thereby attached to the container; (b) adding a known volume of sample to the container; (c) detecting microparticles in a volume of the sample.

We provide, according to a 12$^{th}$ aspect of the invention, a method for treatment of a disease, the method comprising determining the absolute counts of cells per unit volume of a sample using a method according to the first aspect of the invention, determining whether the absolute count of the cells is diagnostic of a disease in an individual from whom the sample is taken, and administering an effective quantity of a pharmaceutical compound capable of treating that disease to that individual.

According to a 13$^{th}$ aspect of the present invention, we provide a kit for determining the absolute counts of cells in a sample comprising a composition or a container as described together with a pharmaceutical composition capable of treating a disease characterised by a particular absolute count of the cell, and optionally instructions for use.

Preferably, the disease comprises hairy cell leukaemia, the cell comprises a hairy cell and the pharmaceutical compound comprises a purine nucleoside analogues (2'-deoxycoformycin or 2-chlorodeoxyadenosine). Alternatively, the disease may comprise acute promyelocytic leukemia (APL), the cell comprises a myeloid population expressing CD13 and CD33 but not CD34 or HLA-DR and the pharmaceutical compound comprises all-trans retinoic acid.

There is provided, according to a 14$^{th}$ aspect of the present invention, a composition comprising a 1:1 mixture of fructose: trehalose together with a predetermined quantity of microparticles and optionally a cell-binding agent or an antioxidant or both.

We provide a method, composition, container, use or kit substantially as hereinbefore described with reference to and as shown in FIGS. 1 to 11 of the accompanying drawings.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855, Lars-Inge Larsson "*Immunocytochemistry: Theory and Practice*", CRC Press inc., Boca Raton, Fla., 1988, ISBN 0-8493-6078-1, John D. Pound (ed); "*Immunochemical Protocols, vol 80*", in the series: "Methods in Molecular Biology", Humana Press, Totowa, N.J., 1998, ISBN 0-89603-493-3, Handbook of Drug Screening, edited by Ramakrishna Seethala, Prabhavathi B. Fernandes (2001, New York, N.Y., Marcel Dekker, ISBN 0-8247-0562-9); Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3; and The Merck Manual of Diagnosis and Therapy (17th Edition, Beers, M. H., and Berkow, R, Eds, ISBN: 0911910107, John Wiley & Sons). Each of these general texts is herein incorporated by reference.

BRIEF DESCRIPTION OF THE FIGURES

FIG. 1A: scatter plot, control. FIG. 1B: fluorescence plot, control. FIG. 1C: scatter plot, matrix. FIG. 1D: fluorescence plot, matrix.

FIG. 2A: CD3 FITC, control. FIG. 2B: CD3 FITC, matrix. FIG. 2C: CD3 RPE, control. FIG. 2D: CD3 RPE, matrix. FIG. 2E: CD3 RPE/Cy5, control. FIG. 2F: CD3 RPE/CY5, matrix. FIG. 2G: CD3 APC, control. FIG. 2H: CD3 APC matrix.

FIG. 2I: CD3 FITC, CD4-APC, control. FIG. 2J: CD3 FITC, CD4-APC, matrix. FIG. 2K: CD3-APC, CD4-FITC, control. FIG. 2L: CD3-APC, CD4-FITC, matrix. FIG. 2M: CD3-PB, CD4-RPE, control. FIG. 2N: CD3-PB, CD4-RPE, matrix. FIG. 2O: CD3-PB, CD8-RPE, control. FIG. 2P: CD3-PB, CD8-RPE matrix.

FIG. 3A: CD3 FITC. FIG. 3B: CD3 RPE. FIG. 3C: CD3 RPE-CY5. FIG. 3D: CD3 APC.

FIG. 3E: CD3/CD4 FITC. FIG. 3F: CD3/CD4 APC. FIG. 3G: CD3PB. FIG. 3H: CD4/CD8 RPE.

FIG. 4A: CD3 RPE-A680 Day 0. FIG. 4B: CD3 RPE-A680 Day 8. FIG. 4C: CD4 FITC Day 0. FIG. 4D: CD4 FITC Day 8.

FIG. 5A: lysed sample, FACSCalibur. FIG. 5B: unlysed sample, FACSCalibur. FIG. 5C: lysed sample, Cyan ADP. FIG. 5D: unlysed sample, Cyan ADP.

FIG. 6A: lysed sample, FACSCalibur. FIG. 6B: unlysed sample, FACSCalibur. FIG. 6C: lysed sample, Cyan ADP. FIG. 6D: unlysed sample, Cyan ADP.

FIG. 12 Comparison of the plots obtained with anti-myeloperoxidase in solution and embedded in a matrix. The first plot displays the FSC vs. SSC and the second shows anti-MPO-APC vs. SSC, where the positive granulocytes can be gated.

DETAILED DESCRIPTION

Reagent Matrix

Figure 1A:
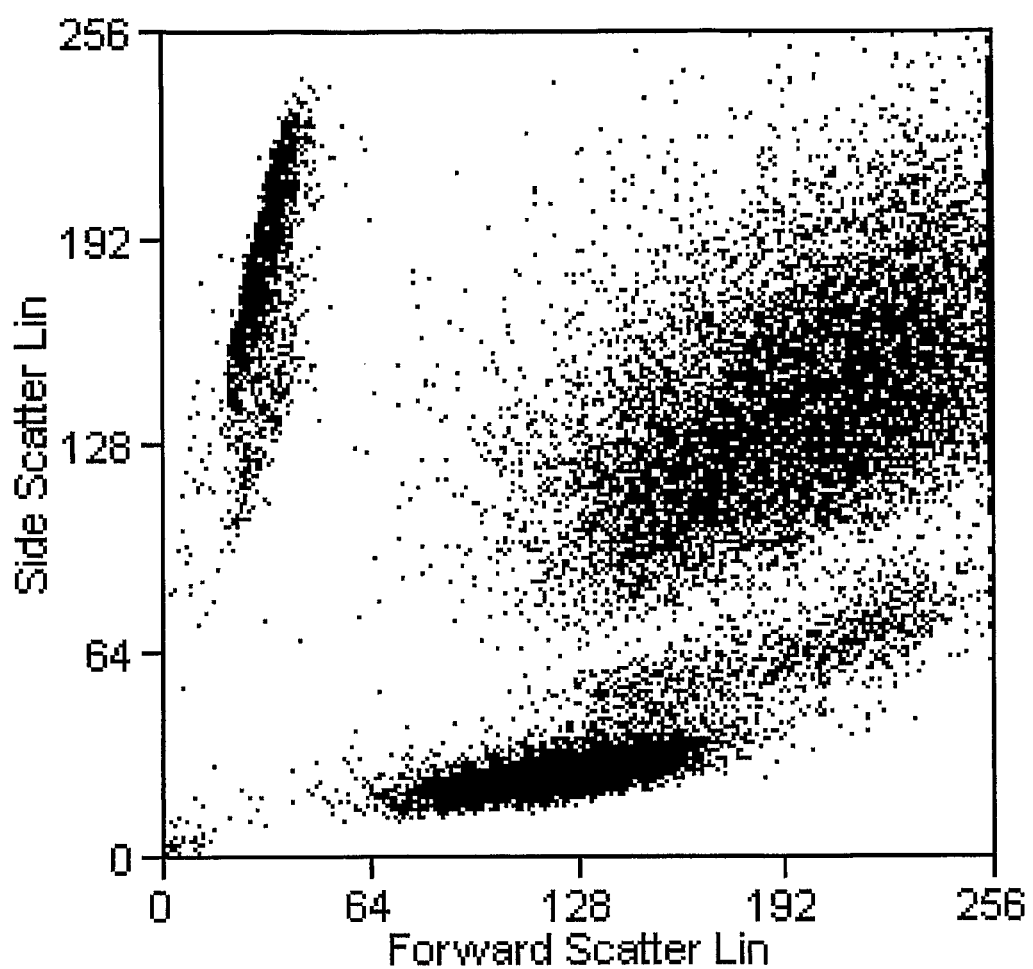
FIGS. 1A-1D show the scatter- and fluorescent properties of CytoCount™ beads in the control (A+B) and incorporated in the Matrix (C+D).
Figure 1B:
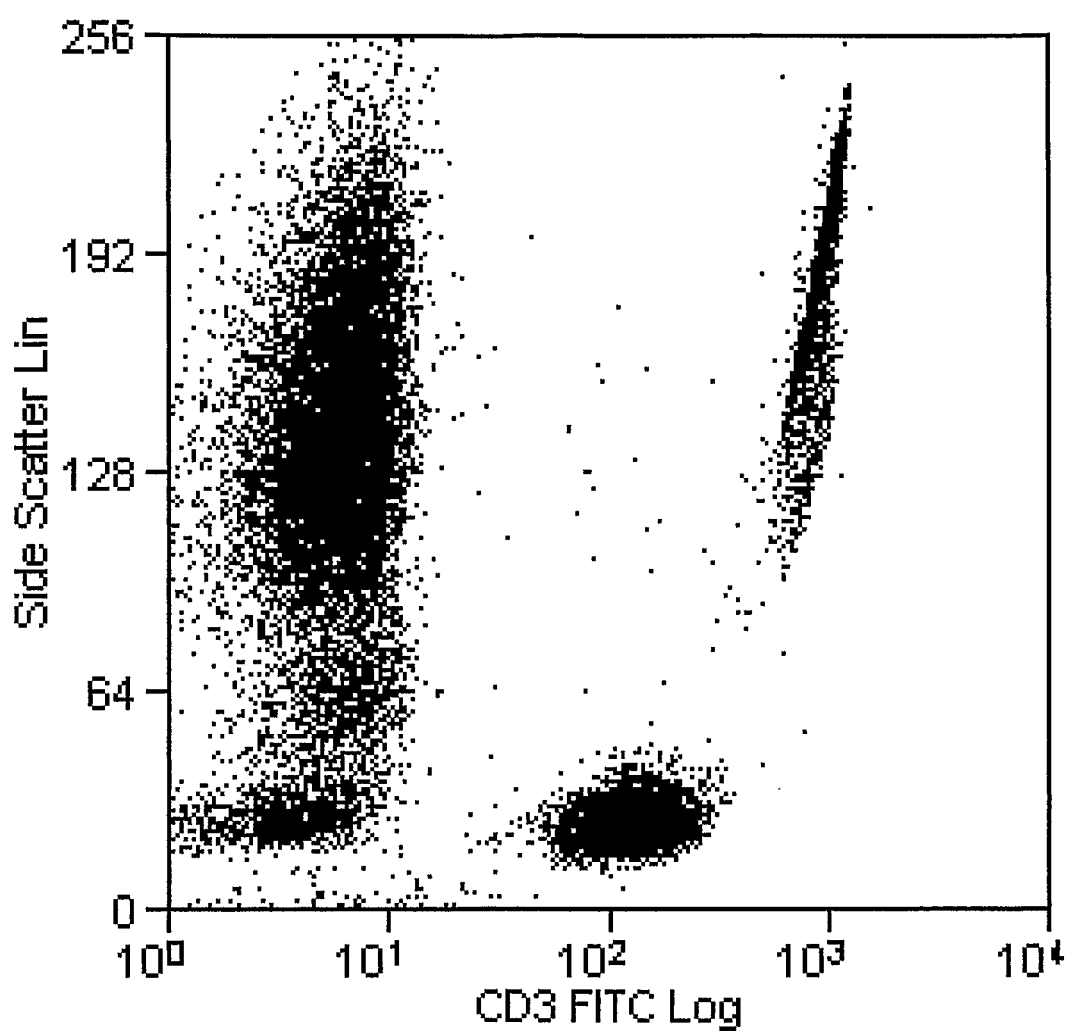
Figure 1C:
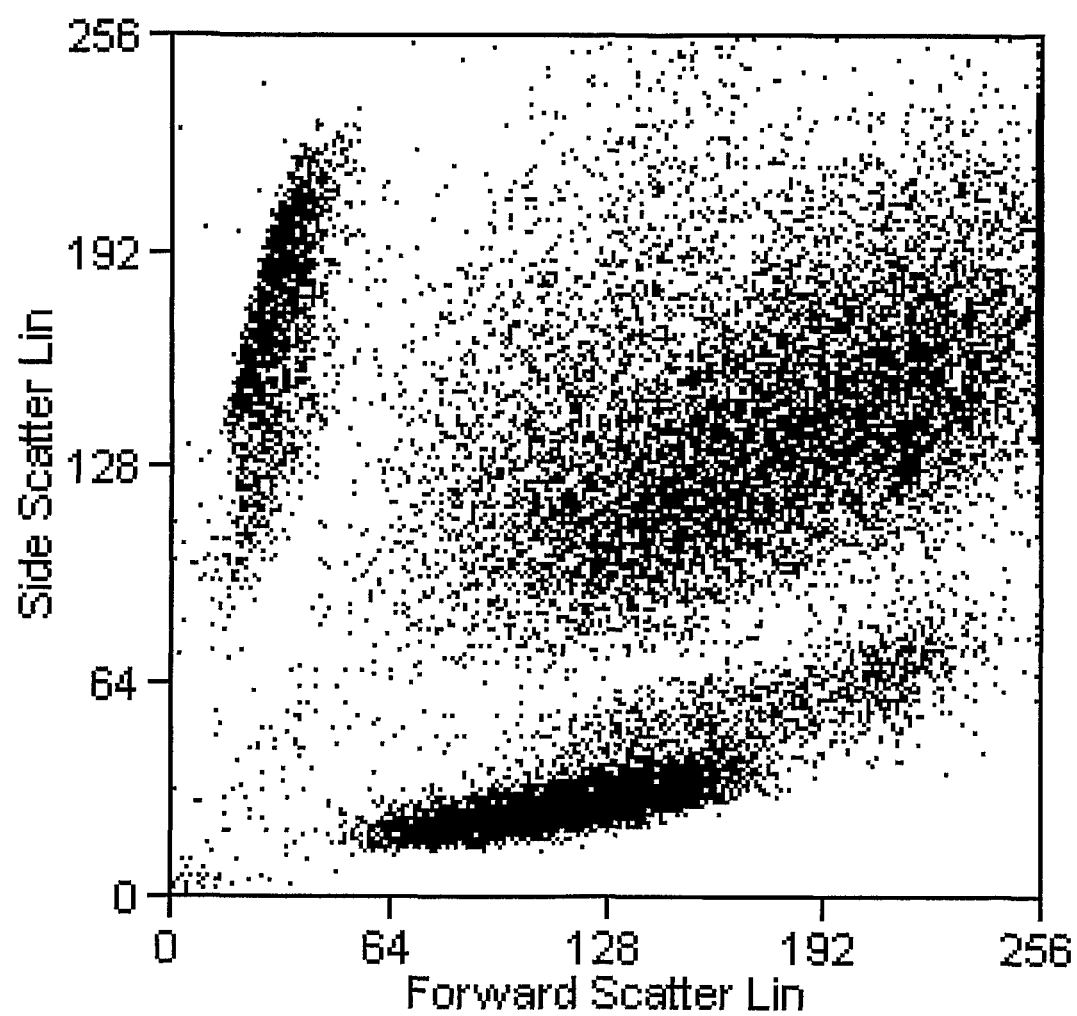
Figure 1D:
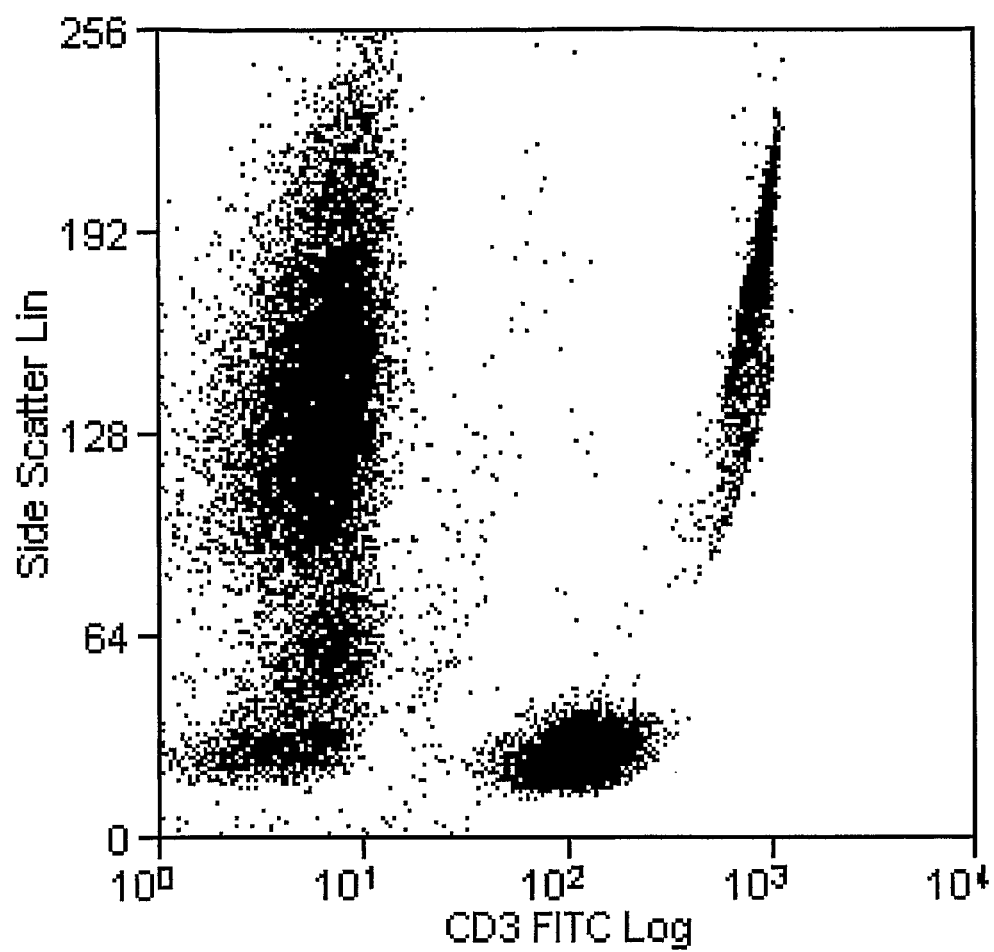

According to the methods and compositions described here, we provide for a composition comprising a predetermined quantity of microparticles disposed in or on a matrix. The composition may optionally, but preferably, comprise a cell-binding agent. For convenience, such a composition or combination of the matrix, microparticles and cell-binding agent is referred to in this document as the "reagent matrix".

The invention generally provides for the embedding or encapsulation of microparticles in an embedding medium, or matrix, which matrix is anchored to the wall of the container. The matrix is capable of adhering to a container to retain substantially the microparticles (and/or the cell-binding agent, as the case may be) in or on the container during routine handling, in the absence of specific restraining means in the container. The microparticles are therefore associated with the matrix in such a way that they are effectively stuck to the container wall(s), during storage and handling of the container comprising the matrix. This enables the container to be handled and stored without loss of microparticles therefrom. The microparticles are present in a known or predetermined quantity, and substantially all the microparticles are attached to the container via the matrix.

Such an embodiment effectively attaches the microparticles to the container, and thereby prevents loss of microparticles without the need for a retaining grid or other similar mechanical restraints in the container. Our invention effectively retains substantially all the microparticles within the container through routine handling. Count precision and accuracy (count to count reproducibility) is maintained, and furthermore no substantial loss of counts is observed as a result of bead-to-bead or bead-to-container adhesion.

An important feature of the methods and compositions described here is the use of a matrix, or embedding medium. The matrix comprises material, details of which are set out below, which is capable of at least attaching or adhering to at least one wall of the container when dry, so that microparticles embedded therein are held to the container. However, when a sample containing cells of interest is added to the container, the matrix releases the microparticles into the sample medium (see below).

The microparticles are associated with the matrix. They may be disposed in, under, on or around, the matrix. They be in particular be supported by or embedded in the matrix. The microparticles may be mixed with the matrix or combined with it. In various embodiments, the microparticles are scattered in the matrix preferably in a uniform dispersion. The exact nature of the relative location or association with the matrix is not important so long as the matrix functions as an adhesive to attach the microparticles to the container during storage and handling (i.e., in the absence of sample).

The reagent matrix is easily made, by providing a suspension of microparticles in a (preferably) aqueous solution of matrix, and at least partially removing solvent by drying or evaporation. In contrast to the prior art, the reagent matrix does not undergo lyophilisation during its production, but is merely dried or evaporated to remove solvent. Lyophilisation, also known as freeze-drying, is a method of drying food or blood plasma or pharmaceuticals or tissue in which material is frozen and then warmed in a vacuum so that the ice sublimes. Such lyophilisation results in a "fluffy" pellet (such as in the prior art TruCOUNT tubes described above), with its attendant problems described above. Example 1 below shows that lyophilisation results in a pellet which is fluffy, foamy and comprises air bubbles. In other words, the reagent matrix as described here is not lyophilised, and is therefore less prone to breaking apart.

The microparticles may be suspended in solvents other than water. Such solvents may comprise methanol, ethanol, propanol, isopropanol, ethylene glycol, propylene glycol or other alcohols, tetrahydrofuran, N-methylpyrrolidinon (NMP) or other solvents. Preferably, the solvents are such that they preserve the stability and fluorescence of microparticles and other reagents.

The microparticles are present in a known or predetermined number in the matrix, and are preferably labelled with a reporter molecule such as a fluorescent molecule or fluorochrome. The matrix may comprise one or more cell-binding agents. Cell binding agents are described in further detail below, but are essentially molecules which are capable of binding to at least one cellular component and therefore identifying it. Preferably, the cell-binding agents are capable of identifying a cell of interest, in such a manner as to enable it to be counted. Exposure of the matrix comprising cell-binding agents to a sample therefore enables the identification and/or enumeration of the cell type of interest.

For this purpose, the one or more cell-binding agents are preferably labelled, preferably with a reporter molecule such as a fluorescent molecule. In highly advantageous embodiments, the cell-binding agent is distinguishable from the microparticles, preferably by virtue of comprising a different label from the microparticles or being of a different size.

In order to obtain the absolute counts of a cell of interest in a sample, a known volume of sample is added to a container comprising the reagent matrix. This releases the microparticles, which are present in a known number, into the sample medium. The cell-binding agent, where present, is allowed to bind to and identify the cells of interest in the sample medium. In order to achieve this, the tube containing the sample may be vortexed and allowed to react for a period of time sufficient for all the relevant cells in the sample to be labelled by the cell-binding agent.

Subsequently, the sample medium may be diluted with an isotonic diluent for subsequent analysis and possible sorting directly on a flow cytometer. The dilution may be any suitable amount such as 20:1 or 10:1, but preferably a 5:1 or 2:1 dilution is used. The low dilution allows for a faster analysis of the sample and is particularly advantageous for a microtitre plate format where small volumes are required. Otherwise the erythrocytes may first be lysed using one of several techniques known to those skilled in the art, e.g., by use of a hypotonic buffer. Since the reagent matrix described herein does not contain a diluent, the treatment of the sample is not restricted, but any technique can be used at will.

The sample medium is then mixed to ensure a homogenous distribution of the microparticles in solution. This can be done using orbital mixing, ultrasound, surface acoustic waves or other forms of mixing, such as by pumping liquid in and out of containers (e.g., jet mixing). Subsequently, the sample medium (or a portion thereof) is run on a flow cytometer. The number of cells of interest as well as the number of microparticles in that portion is counted. This enables the relative number of cells of interest and microparticles in the portion of sample to be determined (in particular the number of cells per microparticle). As the microparticles are present in a known quantity, and the volume of the sample is known, the number of microparticles in a unit volume can be readily established. The absolute count of the cells of interest is calculated by multiplying the number of cells per microparticle with the number of microparticles in a unit volume.

In a some embodiments the sample added is whole blood, and the erythrocytes are lysed prior to running the sample. In another embodiment the sample is run on the flow cytometer unlysed. The methods and compositions described here allow a free choice of whether or not to lyse the sample.

The methods and compositions described here are particularly suited for single platform counting methodologies, in particular where throughput or hands on time is important. It is also suitable for use in complex flow kits with many components or many samples, and may easily be adapted for routine runs by unskilled labour. Examples include haematology and immunology labs, blood banks and clinical research labs.

Advantages

The use of a matrix to retain the microparticles provides a number of advantages to the reagent matrix described here for absolute cell counting.

Retention of Microparticles in Container

The reagent matrix overcomes the problems inherent in the prior art, in particular the problem of maintaining the predetermined number of microparticles through time and handling.

As the matrix adheres to the container to retain the microparticles therein, there is no need for provision of further restraining means such as a retraining grid. Thus, the container as described in this document is capable of being routinely handled, such as by being transported from one location to another, with minimal risk (preferably in the absence of) the matrix being lost from the container.

In various embodiments, the container with the reagent matrix is capable of being so handled with less than 20% of the microparticles being lost, preferably with less than 15%, more preferably less than 10%, 8%, 6%, 5%, 4%, 3%, 2%, or 1% of the microparticles being detached from the wall, in the absence of a further restraining means, preferably mechanical restraining means such as a stainless steel grid. In advantageous embodiments, this is the case when the container is inverted once. By inversion we mean that the container is moved to a position in which the microparticles are above an open end of the container. Preferably, the inversion is such that the microparticles are uppermost, and an open end of the container is lowermost.

In various embodiments, in the course of a single inversion, less than 20%, preferably less than 15%, more preferably less than 10%, 8%, 6% 5%, 4%, 3%, 2%, or 1% of the microparticles are lost from the container. In various embodiments, less than 5% (preferably less than 1%) of the microparticles are detached from the wall, or lost from the tube, when the container is inverted and held in the inverted position for at least 5 seconds. In some advantageous embodiments, the container may be inverted 50 times continuously without substantial loss as set out above.

Preferably, the container is capable of being so handled in at least one of the following ways, without substantial loss as outlined above: between manufacturing site to warehouse, during dispatch to point of sale, between one lab and another, within the lab from one bench to another.

Release of Microparticles into Sample Medium

As described above, microparticle-microparticle adhesion and microparticle-container adhesion can adversely affect the accuracy and precision of the counts obtained.

We have found, surprisingly, however, that the use of an embedding medium, which is capable of adhering to the container surface, does not significantly affect the beads in a manner which affects counting. In particular, we find that the process of being embedded in the matrix does not substantially adversely enhance the "stickiness" of the microparticles.

As shown in the Examples, we observe neither formation of bead-doublets nor any major loss of beads due to the beads sticking to the walls of the sample vial and the fluorescence intensity is unchanged. Thus, contrary to expectations, no substantial reduction in the accuracy and precision of the count possible is observed, and good reproducibility of counts is obtained. This is something which is completely unexpected from the prior art, which has hitherto avoided the use of an embedding medium which is too adhesive or gelatinous in nature.

The microparticles do not substantially stick to one another, following addition of sample.

In various embodiments, the microparticles configured in the methods and compositions described here do not substantially form significant numbers of bead-doublets, triplets, quadruplets or multiplets, after the sample is added to the container containing the microparticles and matrix. Preferably, at least 90%, more preferably at least 95%, more preferably at least 96%, more preferably at least 97%, more preferably at least 98%, more preferably at least 99%, most preferably at least 99.9%, of the microparticles are discrete, i.e., exist as single microparticles without formation of multiplets.

Furthermore, the microparticles do not substantially stick to the surface of the container, following addition of sample Thus, in various embodiments, after the sample is added, or at least at the counting step, the matrix preferably dissolves or disperses in such a way as to release substantially all the microparticles into the medium. In various embodiments, at least 90%, more preferably at least 95%, more preferably at least 96%, more preferably at least 97%, more preferably at least 98%, more preferably at least 99%, most preferably at least 99.9%, of the microparticles are so released. Preferably, less than 5%, more preferably less than 4%, more preferably less than 3%, more preferably less than 2%, more preferably less than 1%, most preferably less than 0.1% of the microparticles adhere to the container after the sample is added, or at the counting step.

In highly advantageous embodiments, the preferred percentages set out above persist through sets of microparticles, matrix and container within a single batch, preferably over at least 3 runs, more preferably over at least 5 runs.

Other Advantages

The reagent matrix described here enables more efficient counting, and less cost in the manufacture of the tubes. Thus, there is no requirement for a large volume of diluent to be packaged with the container, as in the method described in EP 0470810. Since the antibody-antigen recognition reaction is dependant on the concentration of the antibody, a smaller combined volume of reagents and sample as disclosed herein allows for faster reaction with smaller amounts of reagents. Furthermore, a concentrated sample can be analysed faster that a dilute one on a flow cytometer capable of high-speed data acquisition, and can be analysed on miniaturised devices. The fact that diluent is not present (as in EP 0470810) also allows efficient lysis of erythrocytes.

Matrix

The matrix is such that it retains the microparticles in the container when dry but releases the microparticles into the sample medium when a sample containing cells of interest is added to the container. Preferably, the matrix dissolves in the sample medium (or a solvent such as water contained therein) to effect release.

For this purpose, the matrix preferably comprises a gelatinous, viscous, material, which may be liquid, semi-solid or gel-like in consistency. Preferably, the matrix is a viscous liquid.

The matrix may be substantially free of water, or it may comprise water. Preferably (although appearing dry) the matrix contains some water. Preferably less than 30% of the matrix is water. The matrix may comprise liquid other than water, such as glycerol, ethylene glycol, propylene glycol or others.

The matrix is preferably substantially free of water. In various embodiments, the matrix has a viscosity of $10^3$ cP more, preferably $10^4$ cP, more preferably $10^5$ cP, most preferably $10^6$ cP or more. The viscosity may be a dynamic viscosity or a kinematic viscosity, and is preferably measured at a temperature of 25 degrees Celsius. Measurements of viscosity by the use of viscometers are known in the art. Preferably, the viscosity is measured using a Brookfield-type viscometer which determines the required force for rotating a disk in the fluid at known speed. Rheometers and plastometers, which are viscometers that can measure fluids with high viscosity or molten polymers, may also be employed The matrix may preferably exist as a single contiguous mass, or it may be attached to the container as a number of separate pieces. Preferably it is contiguous. Preferably, however, the matrix is such that during handling or storage no portion of the matrix effectively detaches from the container to cause loss of microparticles.

In various embodiments, therefore, the matrix is water soluble, preferably readily soluble in aqueous media. In advantageous embodiments, the matrix dissolves when a sample containing the cells of interest is added into a container comprising the matrix, or otherwise breaks up in such a manner as to release the microparticles into the sample medium. Preferably, all or substantially all of the microparticles are released into the sample medium.

The matrix may be present in any suitable quantity in a container. Preferably, the amount of matrix is sufficient to hold the required number of microparticles in the container. In various embodiments, the amount of matrix is less than 100 mg, preferably less than 50 mg, preferably less than 30 mg, preferably less than 20 mg, preferably less than 10 mg. In advantageous embodiments, the matrix is present at an amount of less than 5 mg, preferably 3 mg or less than 3 mg.

Preferably, the matrix should comprise a non-oxidising (reducing) environment in order to avoid any unwanted redox-reactions. Thus, where a carbohydrate matrix (see below) is employed, the carbohydrates should be non-reducing. Furthermore the matrix should be composed such that is does not crystallise, crack or change phase at any temperature that it may be subjected to under normal transportation and storage.

It is preferable to use a matrix with low melting point to avoid crystallization of the matrix. A high molecular weight is preferable to reduce the osmotic effect on the sample preparation.

In some embodiments, the matrix is based on a water soluble sugar mixture. The matrix or embedding medium may comprise one or more compounds including carbohydrates, polymers, small proteins or others.

Examples of suitable carbohydrates for use in a matrix include saccharose, arabinose, ribulose, fructose, sorbose, glucose, mannose, gulose, galactose, sucrose, lactose, maltose, trehalose, starch, raffinose and melizitose. Cellulose as well as carboxylated or otherwise derivatised cellulose products may also be employed.

Examples of suitable polymers for use in a matrix include polyvinylalcohols, polyethylene glycols, polyethylene imines, polyacryl amides, polyaziridines, glycols, polyacrylic acids, esters or derivatives thereof. It should be clear, that block co-polymers of the aforementioned could also be used.

Examples of small proteins include BSA other albumins or protein fragments such as Byco A.

Mixtures of two or more of the above may also be used. The components of the matrix may be present in any suitable proportion consistent with the desirable properties outlined above. Specifically, we disclose matrices comprising mixtures of carbohydrates, for example, fructose, trehalose and raffinose. Thus, the matrix may comprise any two of fructose, trehalose and raffinose, preferably at a 2:1 ratio, a 1:1 ratio or a 1:2 ratio.

The matrix may comprise 2:1, 1:1 or 1:2 of fructose and trehalose. One highly advantageous embodiment is 3 mg of a 1:1 mixture of fructose and trehalose. The amount of carbohydrate has been determined as the maximum amount that still allows good lysing of the sample.

The matrix may perform other functions, such as providing a stable and inert medium for preserving the microparticles during storage. For this purpose, other components may also be included.

These may include any one or more of preservatives, detergents, fixatives, antioxidants and pH-stabilizers. Examples of preservatives include BRONIDOX, sodium azide and thiomersal. Examples of detergents include TWEEN, TRITON, BRIJ, PLURONIC and TETRONIC, as well as derivatives and mixtures of the aforementioned. Examples of fixatives include vinylsulfone and glutaraldehyde.

The matrix may comprise one or more antioxidants, which are molecules that are radical scavengers. The radicals can be O-, N- C- or S-radicals. In some embodiments, the matrix may comprise scavengers for oxygen-derived radicals such as the superoxide anion or the hydroxyl radical formed by atmospheric oxygen under influence of light, heat or other environmental factors. Examples of such radical scavengers are ascorbic acid, beta-carotene, bilirubin, butylated hydroxytoluene (BHT), butylated hydroxyanisol (BHA) tert-butylhydroquinone (TBHQ) d-alpha-tocopherol, TROLOX and hydroxyanisol. Examples of pH-stabilizers include Good buffers, HEPES, MES, phosphate, citrate.

Microparticles

In general, the microparticles or beads are particles with scatter properties that put them in the context of the cells of interest when registered by a flow cytometer. They can be either labelled with antibodies, fluorochromes or other small molecules or unlabelled. In some embodiments of the invention, the beads are polystyrene beads with molecules embedded in the polymer that are fluorescent in most channels of the flow-cytometer.

The microparticles employed in the methods and compositions described here should preferably be small, and are preferably between 0.1 µm and 100 µm, preferably about 5 µm in diameter. The microparticle should preferably be made of such material and be of such size as to stay suspended, with minimal agitation if necessary, in solution or suspension (i.e., once the sample is added). It should preferably not settle any faster than the cells of interest in the sample. The material from which the microparticles are made should be such as to avoid clumping or aggregation, i.e., the formation of doublets, triplets, quadruplets and other multiplets.

The concentration of the microparticle in the sample suspension should be greater than or equal to the number of cells to be counted. Generally, a 3:1 ratio of microparticles to cells is sufficient. However, a 1:1 ratio is preferred.

The microparticle should preferably be labelled with a reporter molecule, such as a fluorescent molecule (which is described in further detail elsewhere). Alternatively, or in addition, a microparticle which is autofluorescent may be employed.

Microparticles may be selected from the group consisting of fixed chicken red blood cells, coumarin beads, liposomes containing a fluorescent dye, fluorescein beads, rhodamine beads, fixed fluorescent cells, fluorescent cell nuclei, microorganisms and other beads tagged with a fluorescent dye. However, particularly advantageous examples of compact particles that may be used in the invention include microbeads, such as agarose beads, polyacrylamide beads, polystyrene beads, silica gel beads, etc.

Beads

In some embodiments, the microparticle comprises a bead or microbead.

Beads or microbeads suitable for use include those which are used for gel chromatography, for example, gel filtration media such as SEPHADEX. Suitable microbeads of this sort include SEPHADEX G-10 having a bead size of 40-120 (Sigma Aldrich catalogue number 27,103-9), SEPHADEX G-15 having a bead size of 40-120 µm (Sigma Aldrich catalogue number 27,104-7), SEPHADEX G-25 having a bead size of 20-50 µm (Sigma Aldrich catalogue number 27,106-3), SEPHADEX G-25 having a bead size of 20-80 µm (Sigma Aldrich catalogue number 27,107-1), SEPHADEX G-25 having a bead size of 50-150 µm (Sigma Aldrich catalogue number 27,109-8), SEPHADEX G-25 having a bead size of 100-300 µm (Sigma Aldrich catalogue number 27,110-1), SEPHADEX G-50 having a bead size of 20-50 µm (Sigma Aldrich catalogue number 27,112-8), SEPHADEX G-50 having a bead size of 20-80 µm (Sigma Aldrich catalogue number 27,113-6), SEPHADEX G-50 having a bead size of 50-150 µm (Sigma Aldrich catalogue number 27,114-4), SEPHADEX G-50 having a bead size of 100-300 µm (Sigma Aldrich catalogue number 27,115-2), SEPHADEX G-75 having a bead size of 20-50 µm (Sigma Aldrich catalogue number 27,116-0), SEPHADEX G-75 having a bead size of 40-120 µm (Sigma Aldrich catalogue number 27,117-9), SEPHADEX G-100 having a bead size of 20-50 µm (Sigma Aldrich catalogue number 27,118-7), SEPHADEX G-100 having a bead size of 40-120 µm (Sigma Aldrich catalogue number 27,119-5), SEPHADEX G-150 having a bead size of 40-120 µm (Sigma Aldrich catalogue number 27,121-7), and SEPHADEX G-200 having a bead size of 40-120 µm (Sigma Aldrich catalogue number 27,123-3).

SEPHAROSE beads, for example, as used in liquid chromatography, may also be used. Examples are Q-SEPHAROSE, S-SEPHAROSE and SP-SEPHAROSE beads, available for example from Amersham Biosciences Europe GmbH (Freiburg, Germany) as Q SEPHAROSE XL (catalogue number 17-5072-01), Q SEPHAROSE XL (catalogue number 17-5072-04), Q SEPHAROSE XL (catalogue number 17-5072-60), SP SEPHAROSE XL (catalogue number 17-5073-01), SP SEPHAROSE XL (catalogue number 17-5073-04) and SP SEPHAROSE XL (catalogue number 117-5073-60) etc.

Other preferred particles for use in the methods and compositions described here include plastic microbeads. While plastic microbeads are usually solid, they may also be hollow inside and could be vesicles and other microcarriers. They do not have to be perfect spheres in order to function in the methods described here. Plastic materials such as polystyrene, polyacrylamide and other latex materials may be employed for fabricating the beads, but other plastic materials such as polyvinyl chloride, polypropylene and the like may also be used. Polystyrene is a preferred material. The microparticles include unlabelled beads, beads with antibodies, fluorochromes or other small molecules conjugated to the surface or beads with fluorochromes embedded in the polymer.

Cell-Binding Agent

The cell-binding agent comprises a molecule which is capable of binding to a target molecule on or in a cell, and thereby allowing the identification of the cell based on the possession of that target molecule. The cell-binding agent, in many embodiments, enables the labelling of one or more populations of cells.

In highly advantageous embodiments, the cell-binding agent is dispersed in the matrix or reagent matrix in the same manner as the microparticles, as outlined above. Furthermore, preferably, the cell-binding agent is capable of adhering to the container via the matrix, in the same manner as described for the microparticles.

In some embodiments, the target molecule comprises a cell marker, and the cell-binding agent comprises an antibody. Methods of manufacturing polyclonal and monoclonal antibodies, including artificial antibodies, are well known in the art, and a brief description is set out below.

In some embodiments, the antibodies can be against any cell-marker on or in the cells of interest, conjugated to fluorescent labels to make them visible on the flow-cytometer. Examples of such markers include CD2, CD3, CD4, CD5, CD7, CD8, CD10, CD13, CD14, CD15, CD16, CD19, CD20, CD22, CD33, CD34, CD38, CD45, CD56, CD57, CD64, CDw65, CD117 and CD133 or any other marker that will help in identifying the relevant cell-population.

In an alternative embodiment, the cell-binding agent comprises a molecule capable of binding to, preferably intercalating with, DNA, i.e., a. DNA-dye. Examples of such molecules include propidium iodide, Acridine orange, thiazole orange, thioflavin T, 7-amino-actinomycin D (7-AAD), DAPI, Hoechst 33342, TO-PRO-3 iodide, etc. Nucleic acid dyes are described in detail in U.S. Pat. Nos. 4,544,546, 4,883,867 and 4,937,198. For example, we disclose an embodiment comprising a Matrix containing propidium iodide and TWEEN.

In other embodiments, the cell-binding agent comprises a molecule capable of binding to DNA in a sequence-specific manner. Examples of such molecules include DNA-probes, RNA-probes, PNA-probes, LNA-probes or probes made of other oligonucleotide analogues including molecules made up of DNA or RNA incorporating single or stretches of modified nucleotides and/or intercalating molecules.

In further other embodiments, the cell-binding agent comprises non-immunoglobulin affinity proteins such as affibodies or other reagents with specificity for certain cell-markers.

In highly advantageous embodiments, the cell-binding agent is labelled with a reporter molecule, preferably a fluorochrome, to enable the cell-binding agent and the cell to which it is bound, if any, to be identified and preferably counted. These are disclosed in detail later.

We set out a non-exhaustive list of highly advantageous embodiments of the methods and compositions.

Progression of HIV Infection

One embodiment suitable for absolute enumeration of T-helper/inducer lymphocytes employs one or more cell-binding agents capable of identifying any marker for a T-helper/inducer lymphocyte. For example, the cell-binding agent may comprise a labelled anti-CD4 antibody, for example, a mouse-anti-CD4 antibody. Such an embodiment may be used for assessing the risk of AIDS, as well as the onset of opportunistic diseases such as *Pneumocystis carinii* pneumonia. Counting of CD4+ T-helper/inducer cells may also be used as a gauge of immune reconstitution following treatment with anti-HIV drugs.

Stem Cell Counting

Another embodiment suitable for counting stem cells comprises one or more cell-binding agents capable of identifying any marker for a stem cell. For example, the cell-binding agent may comprise a labelled antibody, for example, a fluorescein-mouse-antibody against any one or more of Alkaline phosphatase, Alpha-fetoprotein (AFP), Bone morphogenetic protein-4, Brachyury, Cluster designation 30 (CD30), Cripto (TDGF-1), GATA-4 gene, GCTM-2, Genesis, Germ cell nuclear factor, Hepatocyte nuclear factor-4 (HNF-4), Nestin, Neuronal cell-adhesion molecule (N-CAM), Oct-4, Pax6, Stage-specific embryonic antigen-3 (SSEA-3), Stage-specific embryonic antigen-4 (SSEA-4), Stem cell factor (SCF or c-Kit ligand), Telomerase, TRA-1-60, TRA-1-81, and Vimentin.

A cell-binding agent capable of binding to alkaline phosphatase, Cluster designation 30 (CD30), GCTM-2, Genesis, Germ cell nuclear factor, Oct-4, Stage-specific embryonic antigen-3 (SSEA-3), Stage-specific embryonic antigen-4 (SSEA-4), Telomerase, TRA-1-60 or TRA-1-81 may be used for absolute counting of embryonic stem (ES) or embryonal carcinoma (EC) cells.

A cell-binding agent capable of binding to Alpha-fetoprotein (AFP), GATA-4 gene or Hepatocyte nuclear factor-4 (HNF-4) may be used for absolute counting of endoderm cells.

A cell-binding agent capable of binding to Bone morphogenetic protein-4 and/or Brachyury may be used for absolute counting of mesoderm cells.

A cell-binding agent capable of binding to Cripto (TDGF-1) may be used for absolute counting of ES or cardiomyocyte cells.

A cell-binding agent capable of binding to Nestin may be used for absolute counting of Ectoderm, neural and pancreatic progenitor cells.

A cell-binding agent capable of binding to Neuronal cell-adhesion molecule (N-CAM) or Pax6 may be used for absolute counting of ectoderm cells.

A cell-binding agent capable of binding to Stem cell factor (SCF or c-Kit ligand) may be used for absolute counting of ES, EC, HSC, MSC cells.

A cell-binding agent capable of binding to Vimentin may be used for absolute counting of Ectoderm, neural and pancreatic progenitor cells.

Haematopoietic Stem Cell Counting

Another embodiment suitable for counting stem cells comprises one or more cell-binding agents capable of identifying any marker for a haematopoietic progenitor cell. This includes an embodiment suitable for CD34 enumeration. For example, the cell-binding agent may comprise a labelled antibody, for example, a mouse-anti-CD34 antibody. A patient may be tested for CD34 counts as a means of establishing whether he or she is ready for harvesting of haematopoietic stem cells.

Alternatively, or in addition, the cell-binding agent may comprise anti-CD133 antibody. The CD133 antigen is expressed on stem cells with hematopoietic and nonhematopoietic differentiation potential.

Low-Level Leukocyte Counting

A further embodiment is suitable for counting residual white blood cells in leukodepleted blood products employing a DNA-dye, to distinguish the nucleated white blood cells from the non-nucleated red blood cells. Counting of leukocytes may be used as a quality control for blood products. We therefore disclose a method for absolute counting of leukocytes comprising a DNA-dye such as propidium iodide.

It should be clear that more than one cell marker may be needed in order to get complete separation of cell populations. However, the fluorescence of each marker must have emission wavelengths or intensities that are distinguishable from the others. Furthermore, the microparticles should be distinguishable form the labelled cells by either size, emission wavelength or fluorescence intensity. The combinations of fluorochromes therefore need to be optimised for each embodiment.

Multiple Cell-Binding Agents

It should be clear that the matrix may comprise more than one cell-binding agent. This enables the simultaneous or sequential counting of more than one cell type, as well as allowing cells characterised by the presence of multiple markers to be counted. In embodiments where more than one cell-binding agent is present in the reagent matrix, the cell-binding agents may be labelled with the same reporter, or different reporters (see later).

Thus, it will be evident that where more than one population of cells is to be counted, more than one cell marker may be used (each being specific for a different population). However, the fluorescence of each marker must have emission wavelengths or intensities that are distinguishable not only from each other but also from the microparticle used. When only one immunofluorescence marker is used, the fluorochrome may comprise fluorescein. When two or more immunofluorescence markers are used, the fluorochrome may for example comprise fluorescein and phycoerythrin.

For example, one embodiment is a Matrix containing a combination of antibodies such as CD3-PE (phycoerythrin), CD4-APC (allophycocyanin) and CD45-FITC (fluorescein isothiocyanate). Another embodiment is a Matrix containing a combination of antibodies such as CD34-PE and CD45-FITC/APC. Yet another embodiment is a Matrix containing a combination of antibodies such as CD3-PB (PACIFIC BLUE), CD4-FITC, CD8-APC, CD19-PECy5, CD45-CY (CASCADE YELLOW) and CD56-PE.

In such embodiments, the cell-binding agents are preferably chosen such that the ratio of the counts of cells which are respectively labelled provides useful information. For example, it may be useful to track over time the counts of a cell type with a particular cell marker, against the counts of another cell type with a different marker. Applications for such an embodiment are set out below under "Diagnostic Uses", "Status Determinations" and "Pharmacodiagnostics and Therapeutic Uses".

Label/Reporter/Fluorescent Molecule

In highly advantageous embodiments, the cell-binding agent is labelled with a reporter molecule, to enable the cell-binding agent and the cell to which it is bound, if any, to be identified and preferably counted. Preferably, the microparticles are also labelled with a reporter molecule to enable counting.

Dyes having these properties include the phycobiliproteins (especially phycoerythrin), fluorescein derivatives (such as fluorescein isothiocyanate), peridinin chlorophyll complex (such as described in U.S. Pat. No. 4,876,190), coumarin derivatives (such as aminomethyl coumarin), pthalocyanine dyes (such as ULTRALITE dyes (Ultradiagnostics)) and rhodamine derivatives (such as tetramethyl rhodamine or TEXAS RED (Molecular Probes)).

Preferred examples of fluorochromes include fluorescein isothiocyanate (FITC), phycoerythrin (PE), PE-CY5, PE-CY5.5, PE-CY7, PE-A680, PE-TR (TEXAS RED), allophycocyanin (APC), APC-CY7, PACIFIC BLUE, CASCADE YELLOW, ALEXA dyes, coumarines or Q-DOTS. Any one or more of these fluorochromes may be attached, preferably chemically conjugated, to the cell-binding agent such as an antibody. Optionally, a fluorochrome (or more than one) is attached to the microparticles.

The majority of the fluorochromes are conjugated by reacting a maleimid-coupled fluorochrome with a thiolate-activated antibody, i.e. a chemoselective reaction, whereas FITC, PACIFIC BLUE, CASCADE YELLOW, CY5 and the ALEXA dyes react directly with lysine amino-groups on the antibodies.

The reporter or "label" preferably comprises a light emitting detection means, and the light emitting detection means advantageously emits light of at least a fluorescent wavelength emission. It is preferred that the light emitting detection means comprises a fluorophore or fluorescent tag or group.

A "fluorescent tag" or "fluorescent group" refers to either a fluorophore or a fluorescent molecule or fluorescent protein or fluorescent fragment thereof. The fluorescent tag or group is such that it is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelength that the fluorophore releases energy or fluoresces. "Fluorescent protein" refers to any protein which fluoresces when excited with appropriate electromagnetic radiation. This includes proteins whose amino acid sequences are either natural or engineered.

In some embodiments, the reporter label, preferably fluorescent tag, of the microparticle is different from that of the cell-binding agent. Preferably, the reporter labels are chosen such that the emission wavelength spectrum of one is distinguishable from the excitation wavelength spectrum of the other. The two reporter labels may be excitable by the same wavelength of light, or different wavelengths. Preferably, the emission wavelengths are different. Alternatively, if the decay times of the excited species are different, time resolved fluorescence could be used.

In such an arrangement, it is possible to count the microparticles separately from the cell-binding agents (i.e., the cells to which they are bound), for example, using a different fluorescent channel. However, while distinguishable reporter labels are preferred, it will be clear that this is not absolutely necessary. Indeed, in some embodiments, microparticles which are not labelled with fluorescent tags may be employed, while still being distinguishable from the labelled cells using other parameters. For example, the microparticles may distinguishable form the labelled cells by either size (scatter parameters), emission wavelength (fluorescence parameters) or fluorescence intensity.

It is additionally preferred that the fluorophores comprise fluorescein and tetramethylrhodamine or another suitable pair. In another embodiment, the label comprises two different fluorescent proteins. It is preferred that fluorescent proteins comprise any protein selected from the group consisting of green fluorescent protein (GFP), blue fluorescent protein, red fluorescent protein and other engineered forms of GFP.

Preferably, the polypeptide comprises a cysteine or lysine amino acid through which the label is attached via a covalent bond.

A non-limiting list of chemical fluorophores suitable for use, along with their excitation and emission wavelengths, is presented in Table 1.

TABLE 1

Excitation and emission wavelengths of some fluorophores

| Fluorophore | Excitation (nm) | Emission (nm) | Colour |
| --- | --- | --- | --- |
| PKH2 | 490 | 504 | green |
| PKH67 | 490 | 502 | green |
| Fluorescein (FITC) | 495 | 525 | green |

TABLE 1-continued

Excitation and emission wavelengths of some fluorophores

| Fluorophore | Excitation (nm) | Emission (nm) | Colour |
|---|---|---|---|
| HOECHST 33258 | 360 | 470 | blue |
| R-Phycoerythrin (PE) | 488 | 578 | orange-red |
| Rhodamine (TRITC) | 552 | 570 | red |
| QUANTUM REDO | 488 | 670 | red |
| PKH26 | 551 | 567 | red |
| TEXAS RED | 596 | 620 | red |
| CY3 | 552 | 570 | red |

Examples of fluorescent molecules which vary among themselves in excitation and emission maxima are listed in Table 1 of WO 97/28261 (incorporated herein by reference). These (each followed by [excitation max./emission max.] wavelengths expressed in nanometers) include wild-type Green Fluorescent Protein [395(475)/508] and the cloned mutant of Green Fluorescent Protein variants P4 [383/447], P4-3 [381/445], W7 [433(453)/475(501)], W2 [432(453)/480], S65T [489/511], P4-1 [504(396)/480], S65A [471/504], S65C [479/507], S65L [484/510], Y66F [360/442], Y66W [458/480], 10c [513/527], W1B [432(453)/476(503)], Emerald [487/508] and Sapphire [395/511]. This list is not exhaustive of fluorescent proteins known in the art; additional examples are found in the Genbank and SwissProt public databases.

The fluorescence of the microparticles must be such that in one fluorescence channel it is sufficiently greater than noise from background so as to be distinguishable and also must be distinguishable in other fluorescence channel(s) from the fluorescent dye(s) used as part of the immunofluorescence marker(s) or cell-binding agents. One log difference between the dye(s) and the microparticle fluorescence is sufficient. The concentration of the microparticle should be greater than or equal to the number of cells to be counted. Generally, a 3:1 ratio of beads to cells is sufficient, although a 1:1 ratio is preferred.

Container

For ease of handling, the microparticles and cell-binding agent may be contained in a container. The container can take any suitable form and be made of any suitable material.

The container may in particular take the form of a reagent tube, such as a test tube, or microtitre plate or strips for a microtitre format. Where microtitre plates are used as the container, each of the cell-binding agents, reporters, and microparticles in each of the plates may be the same, or different.

Preferably, the container has a tubular or elongate shape. In some embodiments, the container has a non-circular cross section, for example, a square cross section or a triangular cross section or a polygonal cross section. However, in various embodiments, the container has a circular cross section, and is preferably cylindrical in shape.

The container is preferably closed at one end, and preferably the matrix comprising in which the microparticles are disposed is positioned at or towards the closed end. The closed end may be flat or have a bowl shape. The microparticles are effectively retained in the container during handling through the matrix, and there is therefore no requirement for a retaining grid. Preferably, therefore, the container does not comprise such a grid. The container may, however be closed by a lid or a top seal, e.g. plastic foil (preferred for microtitre plates) or wax or oil to prevent contact with air or moisture. The air in the container could be filtered air, neutral gases, carbon dioxide or any gas that has a protective effect on the reagents in the container. It should be clear that the sample could be added without removing the top seal. Furthermore, a top seal will make it possible to include many different reagent mixtures in one microtitre plate and to use the desired reagent mixtures by simply puncturing the seal, leaving the unused mixtures undisturbed.

The container is preferably transparent or translucent (e.g., frosted) in at least one portion, preferably over the whole of the container. It may however also be impervious to light in order to protect the contents from light. A transparent container may also be packed in a secondary container that is impervious to light, thus protecting the contents from light. The secondary container may be made of foil, preferably a foil bag or pouch. It may also be a box made of plastic or any other material that is or can be made impervious to light.

The primary container may be made of any suitable material, such as glass, heat resistant glass (e.g., Pyrex glass), plastic, polypropylene, polystyrene, etc. Preferably, the material from which the container is made is inert and resistant to chemical attack.

At least a portion of the inner surface of the container, preferably at least one or more of the walls of the container may be treated, by for example coating. The coating may comprise for example, a hydrophobic material such as silicone, or a material capable of preventing components of the sample from sticking to the container. It may also preferably prevent the microparticles (when suspended after addition of sample) from sticking to the surfaces of the container. Such coating material may comprise for example, proteins such as bovine serum albumin (BSA), casein or gelatine. Coating in such a manner with blocking agents prevents non-specific binding to the container.

The container may also comprise a mixing device, preferably incorporated in the container, for mixing the sample or other reagents. Suitable mixing devices comprise vibrating chips or magnets.

The container may be labelled with a means of identification. These may comprise barcodes, infoglyphs or chips, preferably RFID chips. The means of identification may also be capable of storing other information. Such other information may comprise any one or more of the following: patient identification or information, information on the sample, information on the reagents (e.g., manufacture date, lot number, correct protocol), information on steps the sample has been submitted to (e.g., incubation time, temperature, any waiting time between steps, etc).

Preferred containers are those which are employed for laboratory purposes, in particular, for flow cytometry.

Manufacture

The compositions described here are easily manufactured. In general, the material of the matrix is dissolved in an appropriate solvent, such as water, and any required reagents are added to the resulting material.

This is then added to an appropriate container at an appropriate amount, a known number of the microparticles is added, and the solvent removed with agitation if necessary. The solvent may for example be removed by evaporation under reduced pressure or otherwise drying. It is essential that the solvent is not removed by freeze-drying or lyophilisation, as this results in a fluffy pellet (see Example 0).

Removal of solvent results in the deposition of the matrix on the surface of the container. Preferably, not all of the solvent is removed. This enables the matrix to retain some solvent, which allows it to retain its shape or form without crystallisation or cracking.

Due to the simplicity of the manufacturing process it is possible to make many different reagent mixtures in the same production line. Thus it is possible to make panels of different reagent mixtures in one container (microtitre plate) and even produce custom-made panels on demand.

A specific protocol for producing a matrix with microparticles is set out in the Examples.

Sample/Biological Sample

The sample may be derived from any source. In various embodiments, the sample comprises a biological sample, which may preferably comprise a suspension of cells or particles.

As used herein, the term "biological sample" refers to a subset of the tissues of a biological organisms, its cells or component parts. "Biological sample" and "biological specimen" further refer to a homogenate, lysate or extract prepared from a whole organism or a subset of its tissues, cells or component parts, or a fraction or portion thereof.

For example, the biological sample may comprise or be derived from body fluids, including but not limited to sera, plasma, synovial fluid and spinal fluid, blood, mucus, lymphatic fluid, cerebrospinal fluid, saliva, amniotic fluid, amniotic cord blood, urine, vaginal fluid and semen. Furthermore, the biological sample may comprise or be derived from tissues such as ovarian, prostate, heart, placenta, pancreas, ascites, muscle, skin, glandular, kidney, liver, spleen, lung, bone, bone marrow, ocular, peripheral nervous, central nervous, breast and umbilical tissue. Methods for obtaining tissue biopsies and body fluids from mammals and other organisms are well known in the art.

The sample may comprise microorganisms, such as yeast, bacteria, viruses, etc. In particular, the methods and compositions described here are useful for cell counting in the food technology field. The methods we disclose may be used to determine absolute counts of microorganisms used in industrial or biotechnological processes, including fermentation processes. For example, a cell-binding agent which is capable of binding to and identifying a yeast cell may be used to obtain absolute counts of yeast cells in fermentation liquor or media. This is useful in breweries and during the production of beer and wines. Furthermore, the methods and compositions described here are suitable for the counting of live cultures comprising bacterial cells, probiotic cells, etc. One example is the counting of lactic acid bacteria such as *Lactobacillus delbrueckii* subsp. *Bulgaricus* or *Streptococcus salivarius* subsp. *Thermophilus* cells in for example the production of yoghurts. Another example is the determination of absolute count of a recombinant organism in fermentation medium which has been engineered to produce a protein (e.g, a therapeutic protein) or a small molecule such as an antibiotic.

In general, therefore, the methods and compositions described here may be used for absolute counts of any cells involved in food quality controls or cells/particles from any other area that could benefit from cell/particle counting or determination of cell phenotype and/or viability.

In various embodiments, the sample comprises is selected from the group consisting of unlysed whole blood, lymph, spinal fluid, urine and bone marrow. In a some embodiments, the sample comprises whole blood.

The populations of cells that can be counted in a sample such as a biological sample may comprise platelets, red blood cells, white blood cells and subsets and precursors of each. One preferred population of red blood cells comprise reticulocytes. The preferred subsets of leukocytes comprise lymphocytes, monocytes and granulocytes. In one some embodiments, lymphocyte subsets are particularly important and more preferred is the counting of $CD4^+$ T lymphocytes in a whole blood sample.

However, it should be made clear that the methods and compositions described here are applicable to counting any one population of cells (e.g., $CD8^+$ T lymphocytes) as well as to more than one population of cells. For example, in order to count both the number of $CD4^+$ and $CD8^+$ T lymphocytes in a sample, one could use anti-CD4 and anti-CD8 antibodies. In another example, to calculate a three part white blood cell differential, one could use anti-CD45, anti-CD14 and anti-CD15 antibodies. In still another example, to calculate the absolute number of T lymphocytes and/or B lymphocytes, one could use anti-CD3 and/or anti-CD19 (or anti-CD20) antibodies to count T cells or B cells respectively.

In still another example one could use anti-CD3 and anti-CD56 to count natural killer (NK) cells (CD3 negative, CD56 positive) and NK like cells (CD3 positive, CD56 positive). Any population that can be identified by one or a combination of cell markers can be counted alone or can be counted with other populations in the sample.

Any population that can be identified by a single cell marker can be counted alone or can be counted with other populations in the same sample.

Flow Cytometry

The absolute counting method and the compositions for such use as described in this document are particularly suited for use with flow cytometry apparatus. Such apparatus is generally known in the art, but a brief description follows.

In flow cytometry, cells are passed substantially one at a time through one or more sensing regions where each cell is illuminated by an energy source. The energy source generally comprises means that emits light of a single wavelength in a sensing region such as that provided by a laser or a mercury arc lamp with appropriate bandpass filters. The light source may in particular comprise lamps (mercury, xenon); high power water-cooled lasers (argon, krypton, dye laser); low power air-cooled lasers (argon (488 nm), red-HeNe (633 nm), green-HeNe, HeCd (UV)); diode lasers (blue, green, red, violet).

Different sensing regions may include one or more energy sources that emit light at different wavelengths. In series with each sensing region, various light collection means, such as photomultiplier tubes, may be used to gather light that is refracted by each cell (generally referred to as forward light scatter or FSC), and/or light that is reflected orthogonal to the direction of the flow of the cells through a sensing region (orthogonal light scatter, or side scatter, SSC). One or more additional light collection means may be used to collect fluorescent light that may be emitted from the cell as it passes through a sending region and is illuminated by an energy source. Fluorescent emissions at different wavelengths, such as from different fluorescent labels, may be separated by, for instance, conventional thin-film filters, gratings, or the like and separately detected. Light scatter is generally correlated with the physical characteristics of each cell.

Flow cytometers further comprise data recording and storage means, such as a computer, wherein separate channels record and store the light scattered and fluorescence emitted by each cell as it passes through a sending region (i.e., the data collected for each cell comprises "a recorded event"). By plotting orthogonal light scatter versus forward light scatter in either real time or by reanalysis of the data after the events have been recorded, one can distinguish between and count various cell or particle types. For example, using light scatter and by the use of appropriate immunofluorescence markers, such as monoclonal antibodies labelled with fluorochrome of different emission wavelength one can further distinguish between and count cell types within the lymphocyte population (e.g., between CD4+ and CD8+ lymphocytes). U.S. Pat.

Nos. 4,727,020, 4,704,891 and 4,599,307 describe the arrangement of the various components that comprise a flow cytometer and also the general principles of its use.

In various embodiments, the sample is added to the container, matrix, fluorescently labelled microparticles and fluorescently labelled cell-binding agent, and the cell-binding agent is allowed to react with and label the relevant cells of interest. The sample or a portion of the sample is taken and run on a flow cytometer. The flow cytometer is equipped with one or more fluorescence detectors, and a fluorescence trigger is set so that the majority (preferably more than 95%) of microparticles and cells is counted. A fluorescence gate is set so that the fluorescence emissions of each of the microparticles and cells are distinguishable. Alternatively, these fluorescence emissions may be distinguished by their possibly differing emission wavelengths, the different wavelengths being separately detected by the flow cytometer. This may be achieved by the relative brightness of microparticles and cells. The ratio of microparticles to cells in the portion of the sample is utilised together with the known concentration of microparticles to provide an absolute cell count of the relevant cell type.

The Examples set out a specific embodiment which uses flow cytometry to obtain the absolute count of cells.

Kits

We further disclose kits for absolute counting which use or include the methods and compositions described here.

In general, the kit can comprise components of the compositions for absolute counting described here, namely, the matrix, microparticles, and cell-binding agent. The kit may comprise packaging, and it may further comprise instructions for use.

The kit may comprise one or more further elements, including specifically any one or more drugs, pharmaceutical compositions or therapeutic compositions. In particular, the kit may comprise one or more therapeutic reagents suitable for the disease associated with the absolute cell count which it is desired to obtain.

Thus, for example, a kit relevant to HIV/AIDS monitoring, diagnosis or detection may comprise a container with a matrix comprising microparticles and a cell-binding agent which is an anti-CD4 antibody. The kit is suitable for assessing CD4 counts and may comprise anti-retroviral drugs for example, such as protease inhibitors, AZT, etc.

In another example, a kit relevant for monitoring HIV/AIDS in paediatric patients may comprise a container with a matrix comprising microparticles and 6 cell-binding agents which are antibodies against the following cell-markers: CD3, CD4, CD8, CD19, CD45 and CD56. This kit is suitable for assessing CD4-count as well as CD4-positive cells as a percentage of the total lymphocytes.

The kit may comprise one or more containers comprising microparticles, matrix and cell-binding agents. The containers may be arranged in a rack, for example.

The kit may comprise one or more pharmaceuticals. Thus, where the kit comprises a reagent matrix which when used is capable of diagnosing a disease by virtue of the absolute count obtained of a relevant cell type, e.g., CD3+ CD4+, the kit preferably comprises a pharmaceutical which may be used to treat that disease. For example, a kit may comprise a reagent matrix with an anti-CD4 antibody, together with an anti-HIV or anti-AIDS drug such as a protease inhibitor or a anti-retroviral drug. In general, any of the combinations disclosed below under "Pharmacodiagnostics and Therapeutic Uses" may be used as the basis of a kit.

Uses for Calibration, Quality Control and Compensation

The methods and compositions described here may also be used for calibration, quality control, instrument set-up and compensation. They may in particular be used for alignment and setting of laser time delays on a flow cytometer employing beads that preferably are brightly fluorescent and have low variability in both size and fluorescence intensities.

They may in particular be used for quality control of an instrument at regular intervals. A preferred example is daily quality control of the resolution and sensitivity of a flow cytometer.

They may in particular be used for checking the ability of the flow cytometer to resolve bead populations of varying intensities. An example could be a mixture of 2-8 bead populations with different fluorescence intensities (pre-labelled beads) and optionally one blank (not labelled) bead. For compensation, they may be used both for setting online compensation as well as for off-line compensation. In both cases an advantageous embodiment would be a mixture of 2 or more bead populations where each population only carries a single well defined fluorochrome (for example FITC, RPE-CY5, APC or a QUANTUM DOT) and optionally a blank bead population. Preferably, the fluorescence intensities of the labelled bead populations are high.

It should be noted that it is an option to mix independent compositions before use. As an example, a composition with a single bead population carrying FITC may be mixed with a composition with a single bead population carrying RPE before they are analysed on an instrument (e.g. a flow cytometer). As a further example, a composition with 3 bead populations of which the first carries FITC, the second RPE and the third APC (optionally including a blank bead) may be mixed with a composition with one or more bead populations where each population is labelled with a unique fluorochrome (e.g. PACIFIC BLUE, CASCADE YELLOW, RPE-TEXAS RED, RPE-CY5, RPE-CY7, APC-CY7, ALEXA700 or QDOT605).

Another embodiment for compensation is a matrix with one capture bead (a bead carrying covalently bound antibodies with specificity for antibodies of another species an example could be rabbit anti-mouse IgG1). The capture bead can then be loaded with reagent (e.g. monoclonal mouse IgG1 anti-human CD3 labelled with RPE-CY5) thereby turning the capture bead into an RPE-CY5 labelled bead. It is possible to mix a capture bead composition with a pre-labelled bead composition both after capture bead loading as well as before.

In such embodiments it is not necessary to include cell-binding agents. All that is required is a matrix comprising microparticles, in which the microparticles are disposed in or on a matrix which adheres to at least one wall of the container such that substantially all the microparticles are thereby attached to the container. Such matrices may be made in essentially the same manner (and have the similar relevant properties as) the reagent matrices comprising matrix, microparticles and cell-binding agent. We therefore disclose a composition comprising a predetermined quantity of microparticles disposed in or on a matrix which adheres to at least one wall of a container such that substantially all the microparticles are thereby attached to the container.

Another embodiment consists of a composition of pre-labelled beads together with cell-binding reagents. An example of a composition is FITC labelled, RPE Labelled and APC labelled beads as well as Mouse Anti-Human CD3 RPE-CY5. Another example is FITC, labelled, RPE labelled, APC labelled as well as Mouse Anti-Human CD4 RPE-CY5, Mouse Anti-Human CD19 PACIFIC BLUE and Mouse Anti-Human CD8 RPE-CY7. It is possible to mix compositions with pre-labelled beads with compositions with both pre-labelled beads (and/or a blank bead) and cell-binding reagents before as well as after addition of the cell sample.

Information obtained from such embodiments can both be used directly on the instrument (e.g. flow cytometer) for setting the instrument and software controls (one example is for setting compensation parameters and one further example is for setting the PMT voltages). Such setting can be performed manually by a user, automatically by dedicated software or semi-automated (user assisted by software). Similarly, information obtained from such embodiments can be used for quality assurance and thus used to determine whether an instrument is operational or not.

One example could be the determination of whether automated, manual or semi-automated analysis of 6 peak beads (a bead mixture with 6 populations: one blank bead population and 5 fluorescent populations each with a unique intensity) gives rise to detected populations are distinct and well separated by the instrument (e.g. flow cytometer). Information obtained from such embodiments can also be used for monitoring instrument performance. Information obtained from compositions used for compensation can be stored (e.g. in an FCS file) for off-line analysis (e.g. spill-over from each fluorochrome in each fluorescence channel can be measured and used for the calculation of a spill-over matrix). Application of stored information for compensation purposes can be performed by automated, semi-automated or manual means.

As one example, a protocol for calibrating a flow cytometer using beads embedded in a matrix may be conducted as follows: (i) Use a matrix-tube containing calibration beads (ii) dissolve the matrix in the tube with an isotonic buffered diluent (preferably phosphate buffered saline, PBS) thus releasing the beads into solution; (iii) analyse the contents of the tube on the flow cytometer; (iv) adjust the PMT-voltages such that a selected bead peak has a selected intensity mean or median.

As another example, a protocol for monitoring performance of a flow cytometer using beads embedded in a matrix may be conducted as follows: The PMT voltages or peak SD (or CV) obtained in the example above are plotted over time and service is called upon if a threshold value is reached.

A protocol for compensation on a flow cytometer (or data derived from a flow cytometer) using beads embedded in a matrix may be conducted as follows: Compensation is done using beads labelled with the same fluorochromes as the antibodies of interest. These labelled beads are run separately or in a mixture to assess for each fluorochrome how much fluorescence spills over into other fluorescence channels. This spill-over is typically indicated as a fraction or percentage of the signal in the channel assigned to that fluorochrome and is also referred to as the spill-over coefficient (e.g. the signal from a FITC labelled bead may be 1000 in the FITC channel but 300 in the RPE channel. Thus, the FITC spill-over coefficient in the RPE channel is 0.30 or 30%). Based on such a data set of spill-over coefficients, a compensation matrix is calculated. This matrix is allowed to operate on the data set obtained for each cell or particle analysed from the sample of interest. This procedure mathematically removes the signal in any given fluorescence channel that is derived from any other fluorochrome than that belonging to that channel and is well known in the art. The data set for each cell or particle may be corrected for any autofluorescense before the compensation matrix is allowed to operate on the data set.

Diagnostic Uses

The reagent matrix described here may be advantageously employed in the diagnosis of diseases, through the choice of a relevant cell type to be counted. Furthermore, the methods and compositions described here may be also used to monitor health status and to determine the presence of latent infections, for example. The methods and compositions described here may also be used to monitor the progress of treatment, or to provide for an indication of the prognosis.

In various embodiments, the reagent matrix is used to diagnose, detect or monitor HIV/AIDS.

It will be appreciated that it is possible to use the method of absolute counting as set out in this document to compare the absolute count of two cell types. Thus, we provide generally for a method of determining the ratio of the count of a first cell type to the count of a second cell type, the method comprising a method as set out above applied to at least one of (preferably each of) the first and second cell types.

It is evident that a number of diseases are characterised by an imbalance in the ratio of one cell type to another. Accordingly, it is possible to use the methods and compositions described here for absolute cell counting to obtain a diagnosis of, or a preliminary indication of the existence of, such a disease by making the appropriate measurements. It is also envisaged that the methods and compositions described here may be used for an assessment of the prognosis of a patient diagnosed with a disease (which diagnosis, of course, may be conducted using the methods described here).

One example where it is relevant to determine the ratio of specific cell populations is the ratio of $CD4^+$ to $CD8^+$ cells, which is elevated in many patients with immune deficiencies such as AIDS. In the description below, "CD4+ cells" includes "CD3+ CD4+" and "CD8+ cells" includes "CD3+ CD8+" cells.

Thus, we provide for a method of monitoring the progression of HIV infection, the method comprising determining a first absolute count of $CD4^+$ cells and a second absolute count of $CD8^+$ cells in a sample from a patient by a method comprising: (a) providing a container containing: (i) a predetermined quantity of microparticles; and (ii) an anti-CD4 antibody and an anti-CD8 antibody; in which the microparticles are disposed in or on a matrix which adheres to at least one wall of the container such that substantially all the microparticles are thereby attached to the container; (b) adding a known volume of sample to the container; (c) determining the ratio of microparticles to $CD4^+$ cells and $CD8^+$ cells by counting microparticles, $CD4^+$ cells and $CD8^+$ cells in a volume of the sample; (d) determining the absolute count of $CD4^+$ cells and $CD8^+$ cells by multiplying the number of $CD4^+$ cells and $CD8^+$ cells per microparticle by the concentration of microparticles in the sample and (e) determining the ratio of $CD4^+$ to $CD8^+$ cells by dividing the $CD4^+$ count by the $CD8^+$ count. Thus, we obtain the absolute cell counts and the cell ratios at the same time.

Another example of the usefulness of determining ratios of cell populations is set out in U.S. Pat. No. 4,677,061, which describes the importance of determining the ratio of specific cell types in the monitoring of autoimmune patients, particularly patients with multiple sclerosis. In this patent, the ratio of $CD4^+$ or $CD8^+$ lymphocytes to subsets thereof bearing cellular differentiation antigens is determined for the monitoring of multiple sclerosis. Particularly useful is the ratio of $CD4^+$ to $Lp220^+$ cells. Accordingly, the methods and compositions described here may be used to determine the absolute counts of $CD4^+$ cells compared to $CD8^+$ cells, and/or $CD4^+$ cells to $Lp220^+$ cells by the use of appropriate cell-binding agents.

Thus, we provide for a method of diagnosis of multiple sclerosis, the method comprising determining a first absolute count of $CD4^+$ cells in a sample from a patient by a method comprising: (a) providing a container containing (i) a predetermined quantity of microparticles; and (ii) an anti-CD4 antibody; in which the microparticles are disposed in or on a matrix which adheres to at least one wall of the container such that substantially all the microparticles are thereby attached to the container; (b) adding a known volume of sample to the container; (c) determining the ratio of microparticles to $CD4^+$ cells by counting microparticles and $CD4^+$ cells in a volume of the sample; and (d) determining the absolute count of $CD4^+$ cells by multiplying the number of $CD4^+$ cells per microparticle by the concentration of microparticles in the sample.

A second absolute count of $CD8^+$ cells (and/or $Lp220^+$ cells) may be obtained in a similar manner, through use of appropriate anti-CD8 antibodies and/or anti-Lp220 antibodies, and the counts compared. Alternatively, and preferably, a matrix comprising an anti-CD4 antibody together with an anti-CD8 antibody (or together with an anti-Lp220 antibody as the case may be) may be employed. Thus, the aforementioned antibodies (anti-CD4, anti-CD8 and anti-Lp220 conjugated to 3 different fluorescent molecules) could also be combined in one container thus giving the absolute counts as well as the cell ratios simultaneously.

It is also known that other diseases are characterised by an abnormal increase or decrease, with time, of the number of a particular cell type in a human or animal body. We therefore disclose the use of the absolute counting methods and compositions to obtain the absolute count of one cell type at two different times.

An example of a disease associated with cell number changes is HIV infection/AIDS, which is characterised by a decline in the number of $CD4^+$ cells. HIV infections progress through a number of different clinical stages which may be distinguished in a variety of ways. One presently accepted classification system for charting the progress of the disease from initial exposure through the latter stages is described in the Walter Reed Classification System. A number of criteria go into evaluating each of the several stages. For example, the presence or absence of antibodies to HIV or the presence or absence of the virus itself are used as an indication of initial exposure to HIV (WR1). Subsequently, the number of $CD4^+$ lymphocytes in the blood may be measured. A decrease in the number of $CD4^+$ lymphocytes indicates that the disease has progressed (WR3).

We therefore provide a method of diagnosis of HIV/AIDS, the method comprising determining a first absolute count of $CD4^+$ cells in a sample from a patient at a first time point by a method comprising: (a) providing a container containing: (i) a predetermined quantity of microparticles; and (ii) an anti-CD4 antibody; in which the microparticles are disposed in or on a matrix which adheres to at least one wall of the container such that substantially all the microparticles are thereby attached to the container; (b) adding a known volume of sample containing $CD4^+$ cells to the container; (c) determining the ratio of microparticles to $CD4^+$ cells by counting microparticles and $CD4^+$ cells in a volume of the sample; and (d) determining the absolute count of $CD4^+$ cells by multiplying the number of $CD4^+$ cells per microparticle by the concentration of microparticles in the sample.

In various embodiments, the method further comprises establishing a count of total lymphocytes from the patient. Preferably, the percentage of CD4+ cells out of the total lymphocytes is calculated and used for monitoring disease progression in particular for paediatric patients. The count of the total lymphocytes is preferably established in the same sample as that used for counting CD4+ lymphocytes, using preferably the same methodology as described herein.

Alternatively, we provide a method of monitoring HIV the method comprising determining a first percentage of $CD3^+$ $CD4^+$ cells out of the total lymphocytes in a sample from a paediatric patient at a first time point by a method comprising: (a) providing a container containing: (i) a predetermined quantity of microparticles; and (ii) an anti-CD4 antibody; in which the microparticles are disposed in or on a matrix which adheres to at least one wall of the container such that substantially all the microparticles are thereby attached to the container; (b) adding a known volume of sample containing $CD3^+ CD4^+$ cells to the container; (c) determining the ratio of microparticles to $CD4^+$ cells by counting microparticles and $CD4^+$ cells in a volume of the sample; (d) determining the absolute count of $CD4^+$ cells by multiplying the number of $CD4^+$ cells per microparticle by the concentration of microparticles in the sample; (e) determining the ratio of microparticles to lymphocytes by counting microparticles and lymphocytes in a volume of the sample; (f) determining the absolute count of lymphocytes by multiplying the number of lymphocytes per microparticle by the concentration of microparticles in the sample; and (g) determining the CD3+ CD4+ cells as a percentage of the lymphocytes.

The method may further comprise determining a second absolute count of $CD4^+$ lymphocytes in a sample from a patient at a second time point. Preferably, the absolute count of $CD4^+$ cells at the second time point is obtained using a same, similar or corresponding method.

Status Determinations

Apart from disease diagnosis, it is clear that absolute counts of cell types may provide indicators for other conditions of the organism. For example, specific cell types may be counted to establish the health status, nutritional status, mental status, propensity to disease, presence or absence of disease, presence or absence of latent infection, preferably HIV infection of an organism.

For example, estimation of lymphocyte subset counts is a useful tool in diagnosing nutrition and immune changes in continuous ambulatory peritoneal dialysis patients. Flow cytometry can be used to estimate CD3, CD4, CD8, CD19, and CD16+56 antigens using the methods and compositions described here (Grzegorzewska A E, Leander M. Adv Petit Dial. 2002; 18:6-11).

Also, the methods and compositions described here may be used to assist the assessment of activation of immune mechanisms, which is valuable in the early diagnosis of cow's milk allergy (CMA). Large numbers of activated CD19+ B cells and low numbers of CD8+ T cells could be considered as early markers for food allergy since they are already detectable in peripheral blood during the earliest symptoms of CMA (Jarvinen KM, Aro A, Juntunen-Backman K, Suomalainen H. Pediatr Allergy Immunol. 1998 August; 9(3):139-42). Accordingly, the methods and compositions described here may be used to obtain absolute counts of CD19+ B cells and/or CD8+ T cells for assessment of food allergy.

Furthermore, fluorescently labelled multimers of major histocompatibility complex (MHC) molecules are novel reagents that make it possible to directly identify and enumerate disease- and vaccine-induced T-cells by flow cytometric analysis. The antigen specific T cell receptors are recognized by fluorochrome-labelled reagents containing matching peptide-loaded MHC molecules. This makes it possible to utilize flow cytometry for rapid and highly specific visualization of virus specific T cells against e.g. CMV. The use of such multimers in the reagent matrices described here makes it possible to obtain absolute counts of such virus-infected T-cells, for the diagnosis of viral infection and for obtaining information on the likelihood of progression of viral disease.

Pharmacodiagnostics and Therapeutic Uses

It will be evident that the methods and compositions described here may be combined with (known or to be identified) therapeutic methods. Thus, it is possible to use the reagent matrix for diagnosis of a disease, followed by administering a therapeutic regime to alleviate or treat that disease. The reagent matrix therefore also has utility in the field of pharmacodiagnostics.

For example, we disclose the use of the methods and compositions described here for the diagnosis, detection or monitoring of AIDS, followed by the administration of an anti-HIV or anti-AIDS drug such as an anti-retroviral or protease inhibitor.

In general, we disclose the use of any of the methods and compositions described here, in particular, the reagent matrix, for the diagnosis of disease, followed by administration of an appropriate drug to treat or alleviate that disease.

We therefore disclose a method for treatment of a disease, the method comprising determining the absolute counts of cells per unit volume of a sample, the method comprising: (a) providing a container containing: (i) a predetermined quantity of microparticles; and (ii) a cell-binding agent; in which the microparticles are disposed in or on a matrix which adheres to at least one wall of the container such that substantially all the microparticles are thereby attached to the container; (b) adding a known volume of sample to the container; (c) determining the ratio of microparticles to cells by counting microparticles and cells in a volume of the sample; (d) determining the absolute count of cells by multiplying the number of cells per microparticle by the concentration of microparticles in the sample; (e) determining whether the absolute count of the cells is diagnostic of a disease in the individual from whom the sample is taken, and (f) administering an effective quantity of a pharmaceutical compound capable of treating that disease to the patient.

Thus, for example, the methods and compositions described here are useful for the diagnosis and treatment of hairy cell leukemia, Hairy cells display characteristic surface antigens defined by monoclonal antibodies, and a reagent matrix may be employed which comprises comprising microparticles and such antibodies for absolute counting of hairy cells. Such surface antigens include the B-cell markers CD19, CD20 and CD22 as well as the antigens CD11c and CD25, and the reagent matrix will comprise corresponding antibodies capable of detecting such markers. Following diagnosis, hairy cell leukaemia is treated with purine nucleoside analogues (2'-deoxycoformycin or 2-chlorodeoxyadenosine).

As another example, acute promyelocytic leukemia (APL) can be distinguished from other subclasses of acute myeloid leukemia by having a myeloid population expressing CD13 and CD33 but not CD34 or HLA-DR. A reagent matrix comprising microparticles and antibodies capable of detecting such antigens is used for absolute counting of this myeloid population. Following diagnosis, APL is effectively treated using all-trans retinoic acid, when properly diagnosed.

Furthermore, in general, in order to establish diagnosis or establishment of state, the samples are obtained from the same individual, preferably the same organ or tissue within an individual. However, it will be clear that the methods and compositions described here for absolute counting may be used for epidemiological studies, in which the samples may be obtained from different individuals within a population or cohort of interest. The first and second counts may then be compared to provide information about the status of the sample or of each sample, or the status of the tissue, organ, organism, cohort or population from which the sample is derived or of each such tissue, organ, organism, cohort or population. The samples are preferably from different individuals within a population or cohort.

Antibody

The cell-binding agent may preferably comprise an immunoglobulin, preferably an antibody. The antibody is capable of binding to, preferably specifically biding to, the antigen of interest (as described elsewhere in this document) in order to identify a cell type so that it is counted.

Antibodies comprise immunoglobulin molecules Immunoglobulin molecules are in the broadest sense members of the immunoglobulin superfamily, a family of polypeptides comprising the immunoglobulin fold characteristic of antibody molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). The methods described here of detecting detectable entities and of using the reference standard may therefore make use of any immunoglobulin superfamily molecule which is capable of binding to a target. Peptides or fragments derived from immunoglobulins may also be used.

Antibodies, as used herein, refers to complete antibodies or antibody fragments capable of binding to a selected target, and including Fv, ScFv, F(ab') and F(ab')$_2$, monoclonal and polyclonal antibodies, engineered antibodies including chimeric, CDR-grafted and humanised antibodies, and artificially selected antibodies produced using phage display or alternative techniques. Small fragments, such as Fv and ScFv, possess advantageous properties for diagnostic and therapeutic applications on account of their small size and consequent superior tissue distribution. Preferably, the antibody is a single chain antibody or ScFv.

The antibodies may be altered antibodies comprising an effector protein such as a toxin or a label. Use of labelled antibodies allows the imaging of the distribution of the antibody in vivo. Such labels may be radioactive labels or radioopaque labels, such as metal particles, which are readily visualisable within the body of a patient. Moreover, they may be fluorescent labels (such as the ones described here) or other labels which are visualisable on tissue samples removed from patients. Antibodies with effector groups may be linked to any association means as described above.

Antibodies may be obtained from animal serum, or, in the case of monoclonal antibodies or fragments thereof, produced in cell culture. Recombinant DNA technology may be used to produce the antibodies according to established procedure, in bacterial, yeast, insect or preferably mammalian cell culture. The selected cell culture system preferably secretes the antibody product.

Growing of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, for example foetal calf serum, or trace elements and growth sustaining supplements, for example feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

Use of insect cells as hosts for the expression of proteins has advantages in that the cloning and expression process is relatively easy and quick. In addition, there is a high probability of obtaining a correctly folded and biologically active protein when compared to bacterial or yeast expression. Insect cells may be cultured in serum free medium, which is cheaper and safer compared to serum containing medium. Recombinant baculovirus may be used as an expression vector, and the construct used to transfect a host cell line, which may be any of a number of lepidopteran cell lines, in particular *Spodoptera frugiperda* Sf9, as known in the art. Reviews of expression of recombinant proteins in insect host cells are provided by Altmann et al. (1999), *Glycoconj J* 1999, 16, 109-23 and Kost and Condreay (1999), *Curr Opin Biotechnol*, 10, 428-33.

In vitro production provides relatively pure antibody preparations and allows scale-up to give large amounts of the desired antibodies. Techniques for bacterial cell, yeast, insect and mammalian cell cultivation are known in the art and include homogeneous suspension culture, for example in an airlift reactor or in a continuous stirrer reactor, or immobilised or entrapped cell culture, for example in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules are described in the above references and also in, for example, EP 0623679; EP 0368684 and EP 0436597, which are incorporated herein by reference.

The cell culture supernatants are screened for the desired antibodies, preferentially by immunofluorescent staining of cells expressing the desired target by immunoblotting, by an enzyme immunoassay, for example a sandwich assay or a dot-assay, or a radioimmunoassay.

For isolation of the antibodies, the immunoglobulins in the culture supernatants or in the ascitic fluid may be concentrated, for example by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or immunoaffinity chromatography, for example affinity chromatography with the a protein containing a target or with Protein-A.

Antibodies generated according to the foregoing procedures may be cloned by isolation of nucleic acid from cells, according to standard procedures. Usefully, nucleic acids variable domains of the antibodies may be isolated and used to construct antibody fragments, such as scFv.

The methods described here preferably employ recombinant nucleic acids comprising an insert coding for a heavy chain variable domain and/or for a light chain variable domain of antibodies. By definition such nucleic acids comprise coding single stranded nucleic acids, double stranded nucleic acids consisting of the coding nucleic acids and of complementary nucleic acids thereto, or these complementary (single stranded) nucleic acids themselves.

Furthermore, nucleic acids encoding a heavy chain variable domain and/or for a light chain variable domain of antibodies can be enzymatically or chemically synthesised nucleic acids having the authentic sequence coding for a naturally-occurring heavy chain variable domain and/or for the light chain variable domain, or a mutant thereof. A mutant of the authentic sequence is a nucleic acid encoding a heavy chain variable domain and/or a light chain variable domain of the above-mentioned antibodies in which one or more amino acids are deleted or exchanged with one or more other amino acids. Preferably the modification(s) are outside the complementary determining regions (CDRs) of the heavy chain variable domain and/or of the light chain variable domain of the antibody. Such a mutant nucleic acid is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly yeast, bacterial or mammalian cells, to obtain an optimal expression of the heavy chain variable domain and/or a light chain variable domain.

The term mutant is intended to include a DNA mutant obtained by in vitro or in vivo mutagenesis of DNA according to methods known in the art.

Recombinant DNA technology may be used to improve antibodies. Thus, chimeric antibodies may be constructed in order to decrease the immunogenicity thereof in diagnostic or therapeutic applications. Moreover, immunogenicity may be minimised by humanising the antibodies by CDR grafting [European Patent 0 239 400 (Winter)] and, optionally, framework modification [European Patent 0239400; Riechmann et al., (1988) Nature 322:323-327; and as reviewed in international patent application WO 90/07861 (Protein Design Labs)].

Recombinant nucleic acids may be employed comprising an insert coding for a heavy chain variable domain of an antibody fused to a human constant domain γ, for example γ1, γ2, γ3 or γ4, preferably γ1 or γ4. Likewise recombinant DNAs comprising an insert coding for a light chain variable domain of an antibody fused to a human constant domain κ or λ, preferably κ may also be used.

More preferably, CDR-grafted antibodies, which are preferably CDR-grafted light chain and heavy chain variable domains only, may be used. Advantageously, the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule. Such antibodies are known as ScFvs.

Antibodies may moreover be generated by mutagenesis of antibody genes to produce artificial repertoires of antibodies. This technique allows the preparation of antibody libraries, as discussed further below; antibody libraries are also available commercially. Hence, artificial repertoires of immunoglobulins, preferably artificial ScFv repertoires, are used as an immunoglobulin source.

Isolated or cloned antibodies may be linked to other molecules, for example nucleic acid or protein association means by chemical coupling, using protocols known in the art (for example, Harlow and Lane, Antibodies: a Laboratory Manual, (1988) Cold Spring Harbor, and Maniatis, T., Fritsch, E. F. and Sambrook, J. (1991), Molecular Cloning: A Laboratory Manual. Cold Spring Harbor, N.Y., Cold Spring Harbor Laboratory Press).

EXAMPLES

Several examples (Example 1 through Example 10) of the evaluation and practice of the present invention are now presented. It is to be understood that these examples are provided to illustrate some of the benefits and uses of the present invention and are not intended to be exhaustive or limiting of the invention in any way.

Example 0

Drying of Matrix Incorporating Microparticles Using Lyophilisation

1. Three 20% (w/v) solutions of fructose, trehalose and raffinose are made.
2. 4 tubes are made up with 1: fructose; 2: fructose:trehalose, 1:1; 3: fructose:raffinose, 1:1; 4: fructose:trehalose:raffinose, 1:1:1.
3. To each tube is added 100 μL of microparticles.
4. The tubes are cooled to −18° C. for 1 h.

Still frozen, the tubes are placed on a Heto CT110 cold trap equipped with an Edward RV12 vacuum pump.

After two hours the solvent had been removed by lyophilisation, but the process had caused the matrix to form bubbles and cracks in all tubes, enabling part of the matrix to fall out of the tubes. Thus the matrix-tubes were discarded and a slower drying process was developed.

Example 1

Reagent Matrix: Reagents and General Procedures

A. Reagents Used in the Examples Described

TABLE 2

Reagents used in the method examples

| Reagent | Supplier | Catalogue # |
|---|---|---|
| CD3 FITC UCHT1 | Dako A/S | F0818 |
| CD3 RPE UCHT1 | Dako A/S | R0810 |
| CD3 RPE-Cy5 UCHT1 | Dako A/S | C7067 |
| CD3 RPE-A680 UCHT1 | Dako A/S | — |
| CD3 Pacific Blue UCHT1 | Dako A/S | PB982 |
| CD3 APC UCHT1 | Dako A/S | C7225 |
| CD4 RPE MT310 | Dako A/S | R0805 |
| CD4 FITC MT310 | Dako A/S | F0766 |
| CD4 APC MT310 | Dako A/S | C7226 |
| CD8 RPE DK25 | Dako A/S | R0806 |
| CD8 APC DK25 | Dako A/S | C7227 |

TABLE 2-continued

Reagents used in the method examples

| Reagent | Supplier | Catalogue # |
|---|---|---|
| CD19 RPE-CY5 HD37 | Dako A/S | C7066 |
| CD45 RPE-CY5 T29/33 | Dako A/S | C7099 |
| CD45 FITC T29/33 | Dako A/S | F0861 |
| CD45 APC T29/33 | Dako A/S | C7230 |
| CD45 CASCADE YELLOW T29/33 | Dako A/S | — |
| CD56 RPE MOC-1 | Dako A/S | R7127 |
| MPO APC MPO-7 | Dako A/S | C7246 |
| Negative control | Dako A/S | X0968 |
| CytoCount ™ beads | Dako A/S | S2366 |
| Easy-Lyse ™ | Dako A/S | S2364 |
| Uti-Lyse ™ | Dako A/S | S3350 |
| INTRASTAIN | Dako A/S | K 2311 |
| Fructose | Sigma | F-0127 |
| Trehalose | Sigma | T-9531 |
| TruCOUNT ™ tubes | Becton Dickinson | 340334 |
| MultiTEST ™ reagent | Becton Dickinson | 342417 |
| FACS ™ Lysing solution | Becton Dickinson | 349202 |

Note:
Dako A/S was previously known as DakoCytomation A/S

B. Preparation of the Matrices
1. 20% (w/v) solutions of the sugars are made up and mixed in a 1:1 ratio.
2. 15 μL of the mixture is added to 5 mL Falcon tubes (Becton Dickinson).
3. If desired, antibodies are added in the required amount.
4. CytoCount™ beads are added to each tube using reverse pipetting in the required amount.
5. The mixtures are dried under vacuum at room temperature over night and are subsequently stored at 2-8° C. protected from light until used.

C. Lysing using Easy-Lyse™
1. 2 mL of Easy-Lyse™ is added to each tube.
2. The tubes are vortexed quickly
3. The tubes are incubated in the dark for 15 min. at room temperature D. Lysing using Uti-Lyse™
1. 100 μL of Uti-Lyse™ reagent A is added to each tube.
2. The tubes are vortexed quickly.
3. The tubes are incubated in the dark for 10 min. at room temperature.
4. 1 mL of Uti-Lyse™ reagent B is added to each tube.
5. The tubes are vortexed quickly.
6. The tubes are incubated in the dark for 10 min. at room temperature.

E. Lysing Using FACS™ Lysing Solution
1. 450 μL of FACS™ Lysing solution is added to each tube.
2. The tubes are vortexed quickly
3. The tubes are incubated in the dark for 15 min. at room temperature.

Example 1A

Reagent Matrix: Improved Procedure for Matrix Preparation

Preparation of the Matrices
1. 20% (w/v) solutions of the sugars are made up and mixed in a 1:1 ratio.
2. 15 μL of the mixture is added to 5 mL Falcon tubes (Becton Dickinson).
3. Antibodies are added in the required amount.

4. If desired, an antioxidant is added in the required amount.

5. CytoCount™ beads are added to each tube using reverse pipetting in the required amount.

6. The mixtures are dried under vacuum at 2-8° C. over night and are subsequently stored at 2-8° C. protected from light until used.

Example 2

CD4-Counting with Matrix-Embedded Counting Beads

This Example describes CD4-counting using counting beads incorporated in a carbohydrate matrix, compared to adding the counting beads immediately prior to analysing the sample.

Procedure 20 matrices are prepared according to procedure B, Example 1, and using 100 µL CytoCount™ beads.

Preparing the Matrix Samples Along with the Corresponding Controls

1. To each of 40 Falcon tubes (20 Matrix and 20 controls) is added 10 µL CD3 FITC, 10 µL CD4 RPE and 10 µL CD45 RPE-Cy5.

2. To each tube is added 100 µL of whole blood specimen.

3. The samples are vortexed and incubated in the dark for 15 min. at room temperature.

4. Half the tubes (10 Matrix and 10 controls) are lysed with Easy-Lyse™ according to procedure C, Example 1; the other half is lysed with Uti-Lyse™ according to procedure D, Example 1, to remove erythrocytes.

All the samples are analysed on a FACSCalibur™ flow cytometer with Cellquest™ software version 3.3. For the controls, 100 µL of CytoCount™ beads are added immediately prior to analysing. All samples are vortexed for 5 seconds immediately before analysing. The count of CD4 lymphocytes per unit specimen volume is obtained.

Results

The results are shown in FIG. 1A-D.

FIG. 1 shows the scatter- and fluorescent properties of CytoCount™ beads in the control (A+B) and Matrix sample (C+D). Both samples are lysed with Easy-Lyse™.

In the scatter-plots (A+C) the beads are placed in the upper left-hand corner, whereas the lymphocytes are the dense population at the bottom of the plots. In the fluorescence plots (B+D) the beads are in the upper right-hand corner and the lymphocytes are in the middle at the bottom of the plots. The plots are quite similar for Matrix and control samples except that the beads and the granulocytes are spread out slightly more in the scatter plots. In the fluorescence plots the beads are placed exactly the same for Matrix and control.

TABLE 3

CD4 count/µL specimen as determined in Example 2

| Sample type | Control/Easy-Lyse ™ | Matrix/Easy-Lyse ™ | Control/Uti-Lyse ™ | Matrix/Uti-Lyse ™ |
|---|---|---|---|---|
| Mean | 1037 | 1069 | 1060 | 1113 |
| Standard Dev. | 28.4 | 25.4 | 28.5 | 18.7 |
| C.V. | 2.7 | 2.4 | 2.7 | 1.7 |

The results show that the Matrix does not affect the fluorescence of the beads and there is no formation of doublets. The counts for the Matrix-samples are consistent with the counts obtained with the controls and the CV's are very low. High consistency and low variation are of the outmost importance in absolute counting to ensure that a sample will give the same count and thus the same diagnosis regardless of whether tested today or tomorrow. It would be possible to adjust the counts to give an even closer match with the controls.

Summary

CytoCount™ counting beads can be incorporated into a carbohydrate matrix without any affect on the fluorescence; giving rise to counts that are consistent with the controls. The CV's obtained with the Matrix samples are very low.

Example 3

CD3 Counting with Matrix Embedded Antibody-Conjugates and Counting Beads

This Example describes the use of matrices containing 4 different antibody-conjugates along with counting beads.

Procedure 4 matrices are prepared according to procedure B in Example 1 with 100 µL CytoCount™ beads and 10 µL CD3 FITC, CD3 RPE, CD3 RPE-Cy5 and CD3 APC respectively, i.e. only one antibody-conjugate per Matrix-tube.

Preparing the Matrix Samples Along with the Corresponding Controls

To 4 new Falcon tubes is added 10 µL CD3 FITC, CD3 RPE, CD3 RPE-Cy5 and CD3 APC respectively. These are the controls.

1. To all 8 tubes (4 controls and 4 Matrix-tubes) is added 100 µL of whole blood specimen.

2. The samples are vortexed and incubated in the dark for 15 min. at room temperature.

3. The samples are lysed with Easy-Lyse™ according to procedure C, Example 1.

For the controls, 100 µL of CytoCount™ beads are added immediately prior to analysing. All samples are vortexed for 5 seconds immediately before analysing. All the samples are analysed on a FACSCalibur™ flow cytometer with Cellquest™ software version 3.3 to give the fluorescent intensity of the CD3-positive cells.

Results

The results are shown in FIGS. 2 A-H.

FIG. 2 shows the fluorescence vs. side scatter plots of whole blood stained with 4 different CD3-conjugates in the control (FIG. 2A, FIG. 2C, FIG. 2E and FIG. 2G) compared to the Matrix (FIG. 2B, FIG. 2D, FIG. 2F and FIG. 2H) where the conjugates are incorporated in the Matrix.

The fluorescence intensities are in all cases comparable, and there are no problems with separating the CD3-positive populations (dense population centred at the bottom of the plots) from the negative populations.

TABLE 4

Median fluorescent intensities determined in Example 3

| Fluorochrome | Control | Matrix | Matrix/Control % |
|---|---|---|---|
| FITC | 228.8 | 205.4 | 89.8 |
| RPE | 264.2 | 143.3 | 54.2 |
| RPE-CY5 | 264.2 | 171.5 | 64.9 |
| APC | 283.9 | 237.1 | 83.5 |

Summary

The antibody-conjugates that are incorporated in the matrix displayed fluorescent intensities that are comparable to the controls and allowed for easy and unambiguous gating of the CD3 positive population.

Example 3A

CD4 Counting with Matrix Embedded Antibody-Conjugates and Counting Beads (Two Colour Antibody-Conjugate Mixtures)

This Example describes the use of 4 matrices containing 4 different two-colour antibody-conjugate mixtures along with counting beads.

Procedure 4 two-colour mixtures are prepared as 1:1 mixtures of the single antibodies:

TABLE 5

Mixtures used in Example 3A

| Antibody-mix | Antibody-conjugates | |
| --- | --- | --- |
| Dual 1 | CD3-FITC | CD4-APC |
| Dual 2 | CD3-APC | CD4-FITC |
| Dual 3 | CD3-PB | CD4-RPE |
| Dual 4 | CD3-PB | CD8-RPE |

4 matrices are prepared according to procedure B in Example 1 with 50 µL CytoCount™ beads and 5 µL Dual 1, Dual 2, Dual 3 and Dual 4 respectively.

Preparing the Matrix Samples Along with the Corresponding Controls

To 4 new Falcon tubes is added 5 µL Dual 1, Dual 2, Dual 3 and Dual 4 respectively. These are the controls.

1. To all 8 tubes (4 controls and 4 Matrix-tubes) is added 50 µL of whole blood specimen.
2. The samples are vortexed and incubated in the dark for 15 min. at room temperature.
3. The samples are lysed with Uti-Lyse™ according to procedure D, Example 1.

For the controls, 50 µL of CytoCount™ beads are added immediately prior to analysing. All samples are vortexed for 5 seconds immediately before analysing. All the samples are acquired and analysed on a Cyan™ ADP with Summit v4.2 software to determine the count of CD3+ CD4+ or CD3+ CD8+ cells. The threshold is set on CD3 except for Dual 2, where it is set on CD4, since the beads are not positive in the APC-channel.

Results

The results are shown in FIGS. 2 I-P.

Figure 2A:
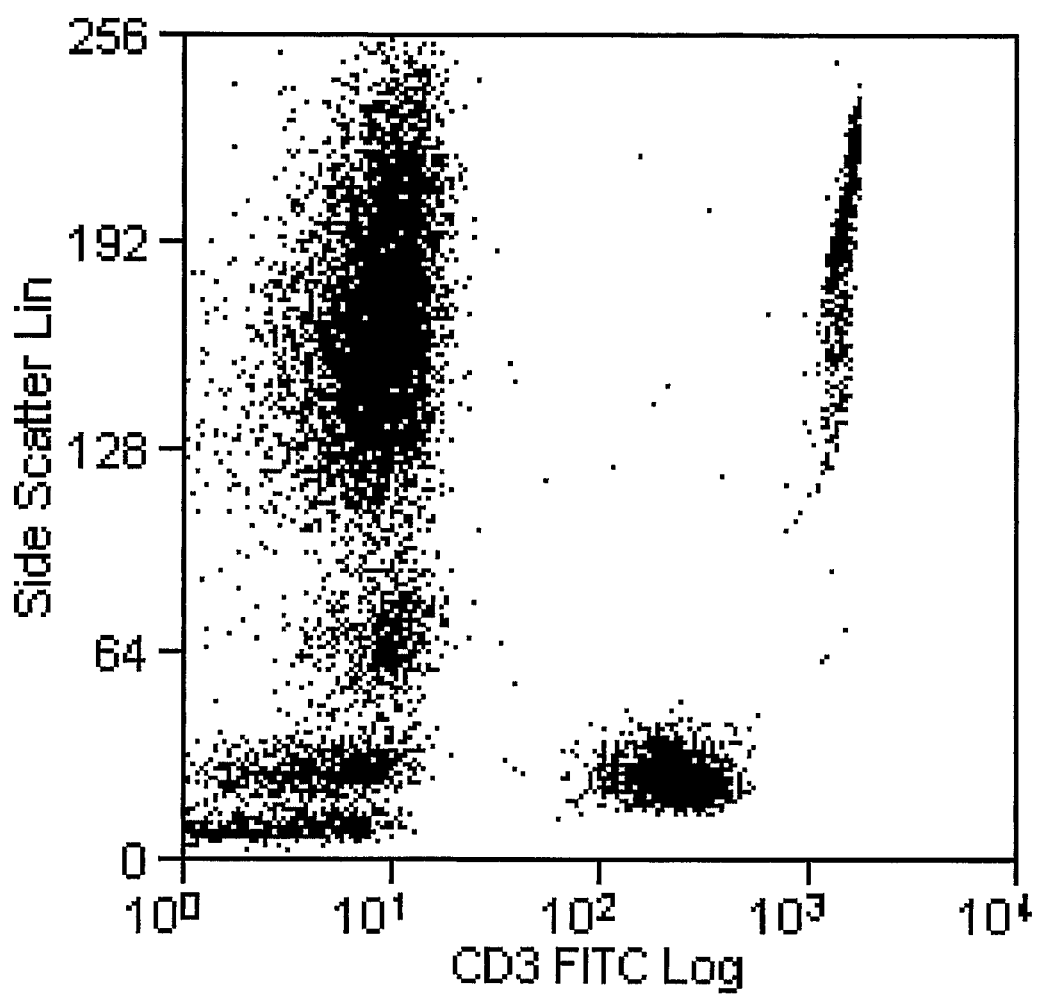
FIGS. 2A-2H show the fluorescence vs. side scatter plots of whole blood stained with 4 different CD3-conjugates in the control (FIGS. 2A, 2C, 2E and 2G) compared to the Matrix (FIGS. 2B, 2D, 2F and 2H) where the conjugates are incorporated in the Matrix.
Figure 2B:
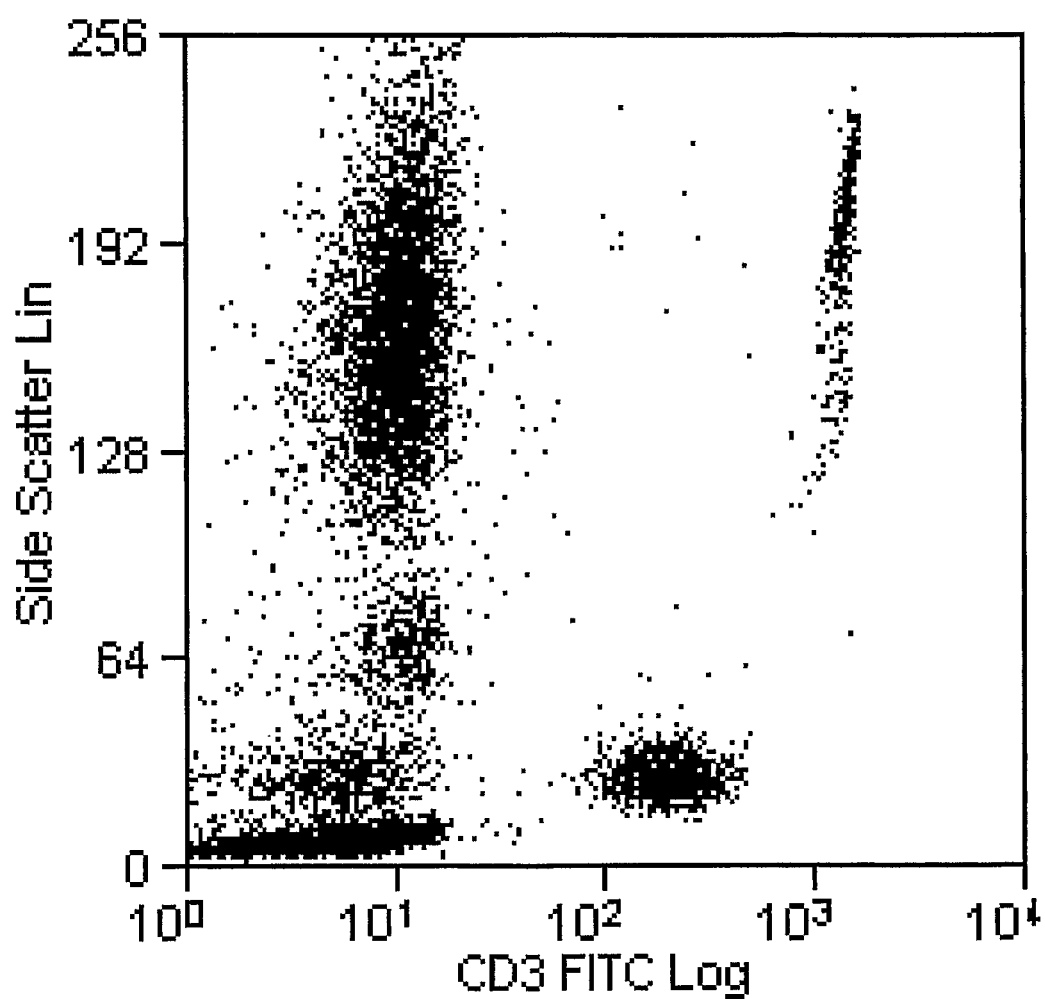
Figure 2C:
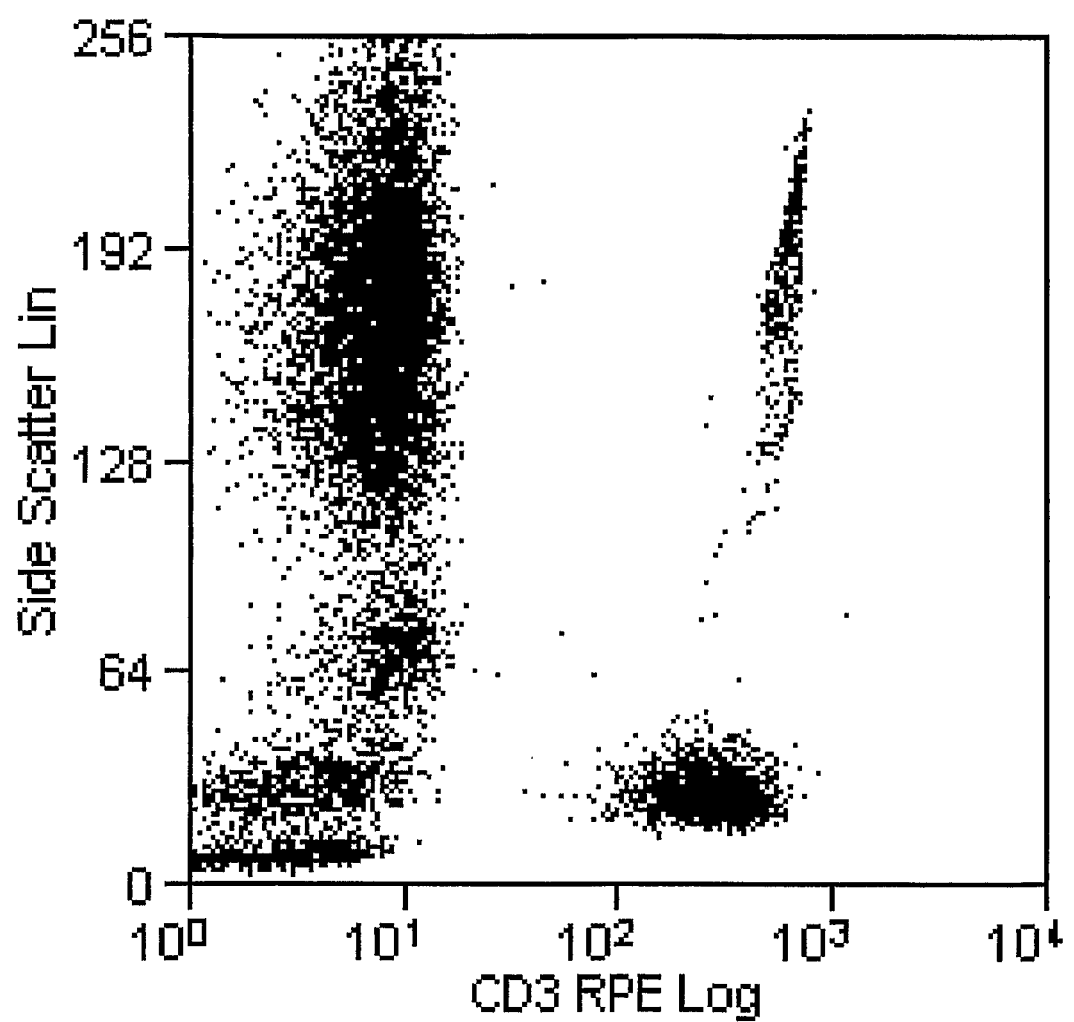
Figure 2D:
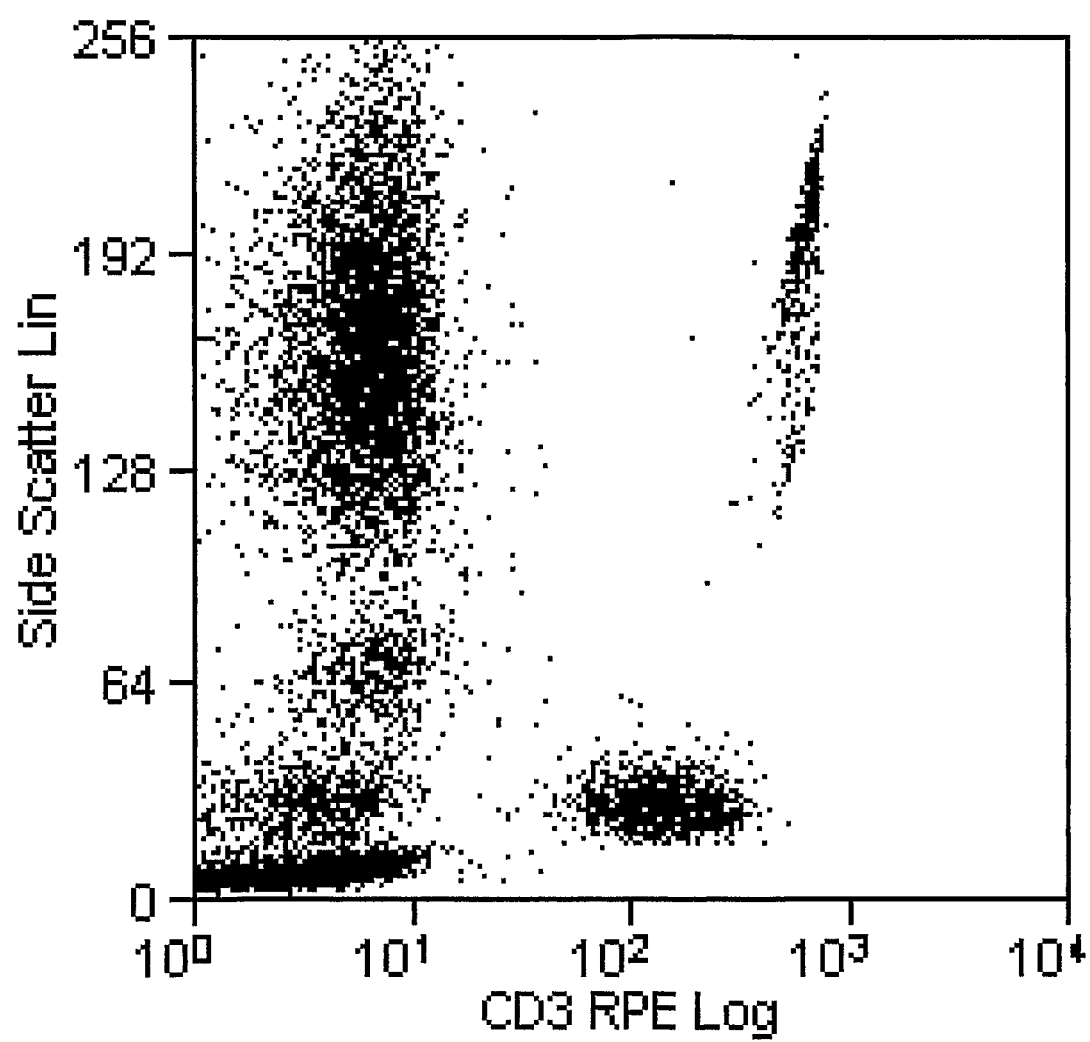
Figure 2E:
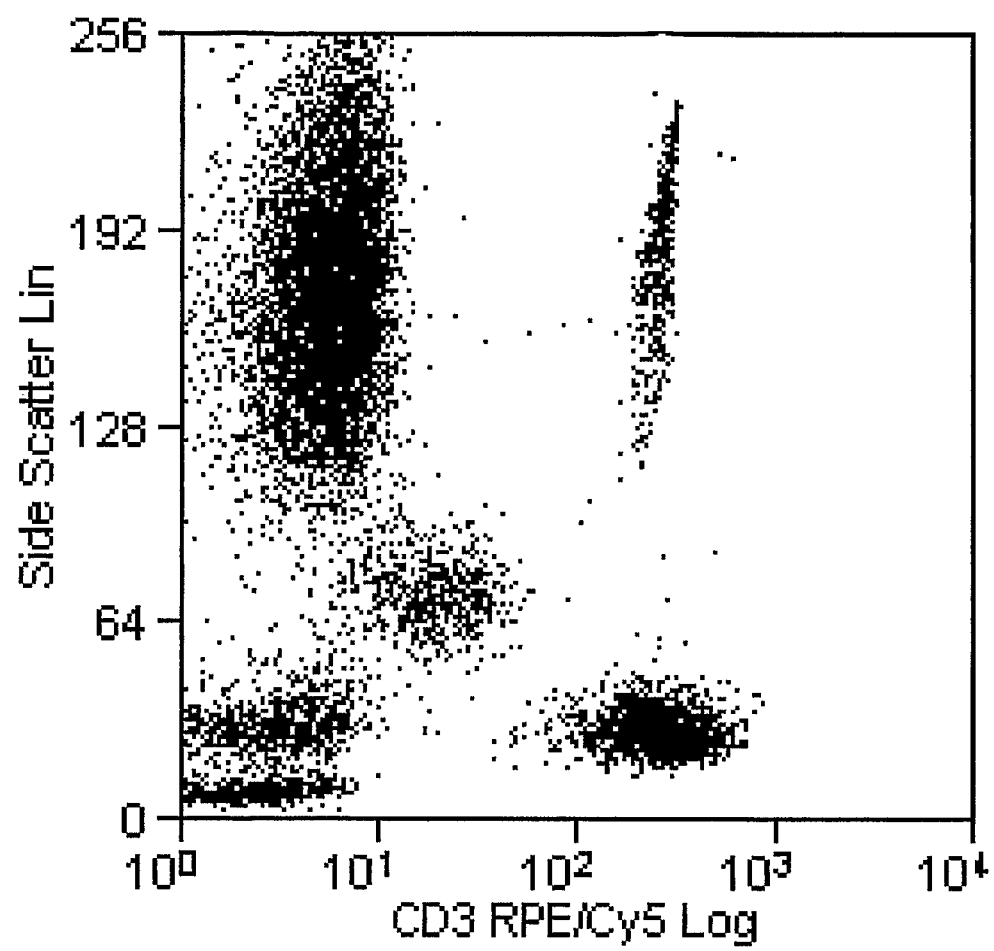
Figure 2F:
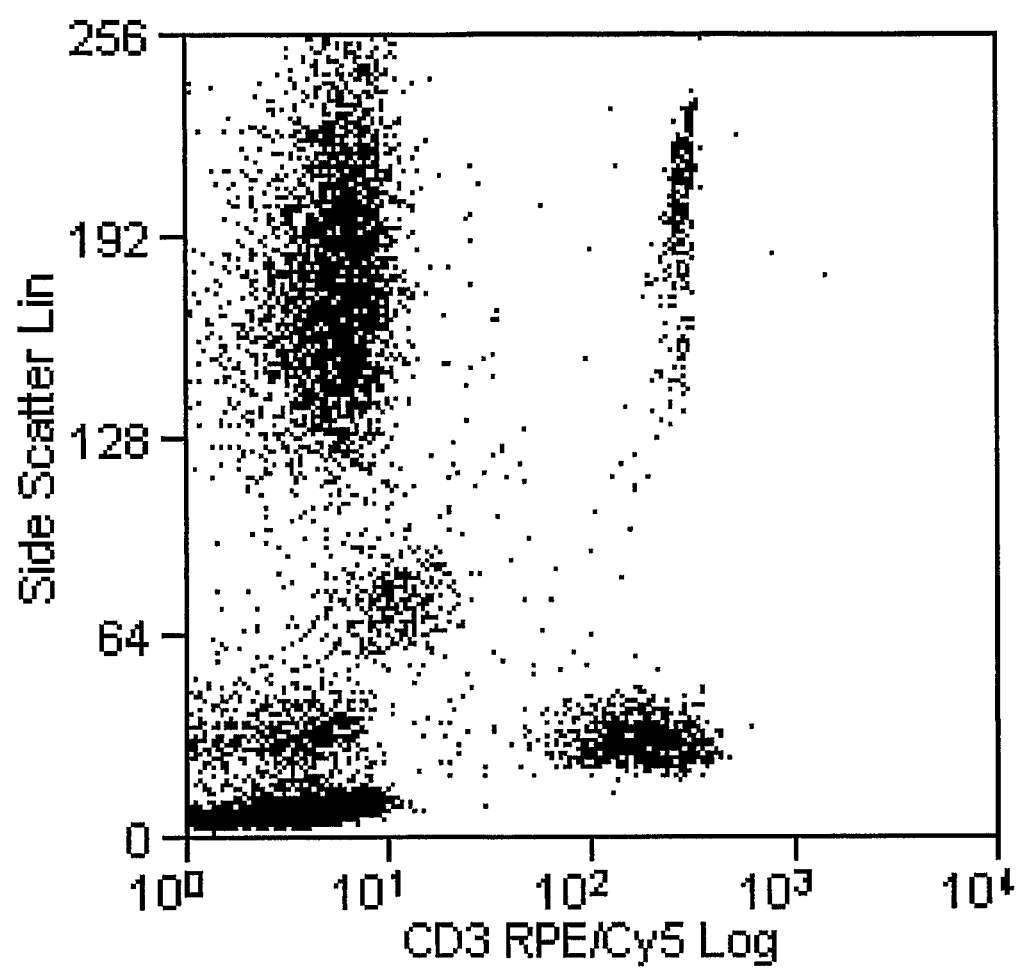
Figure 2G:
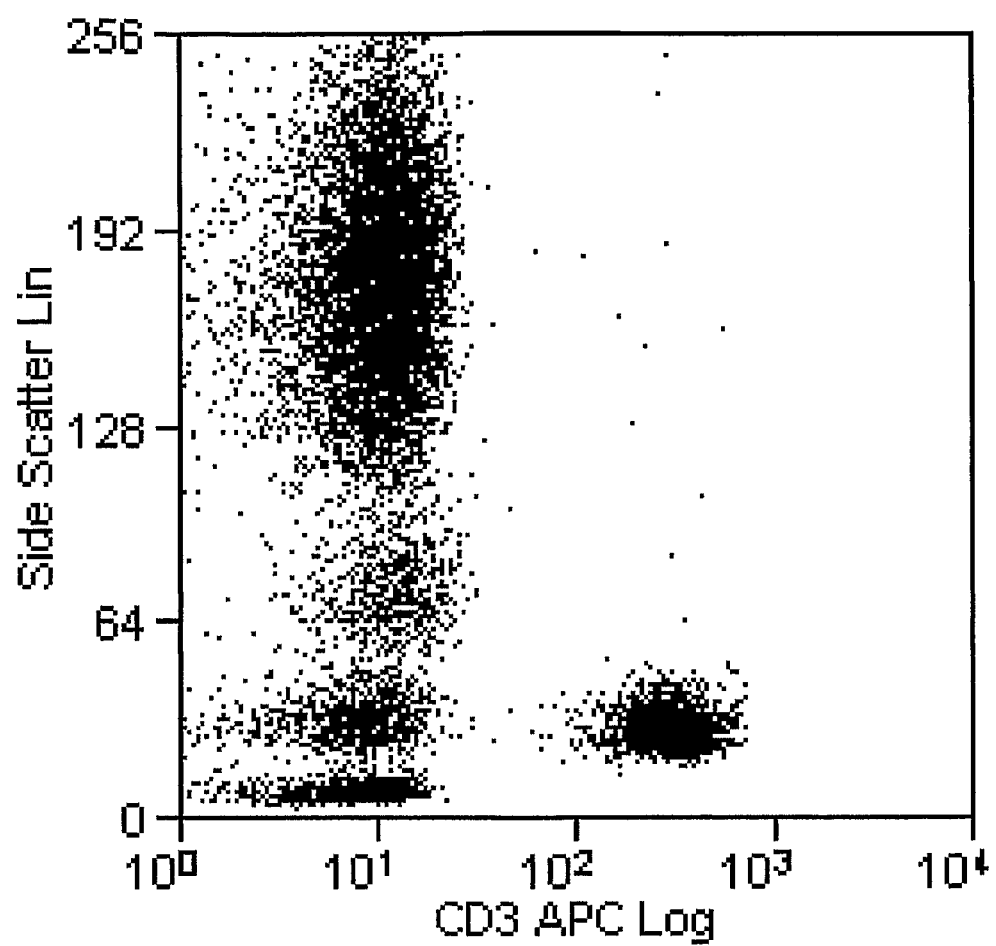
Figure 2H:
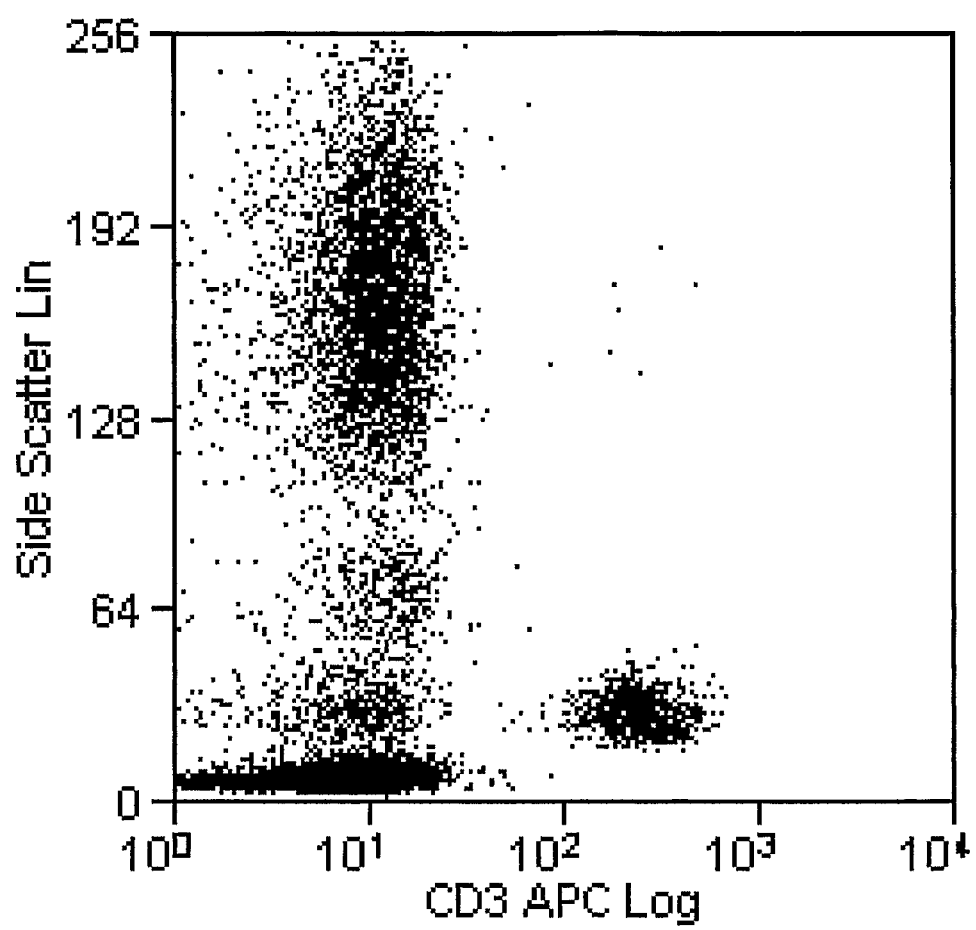
Figure 2I:
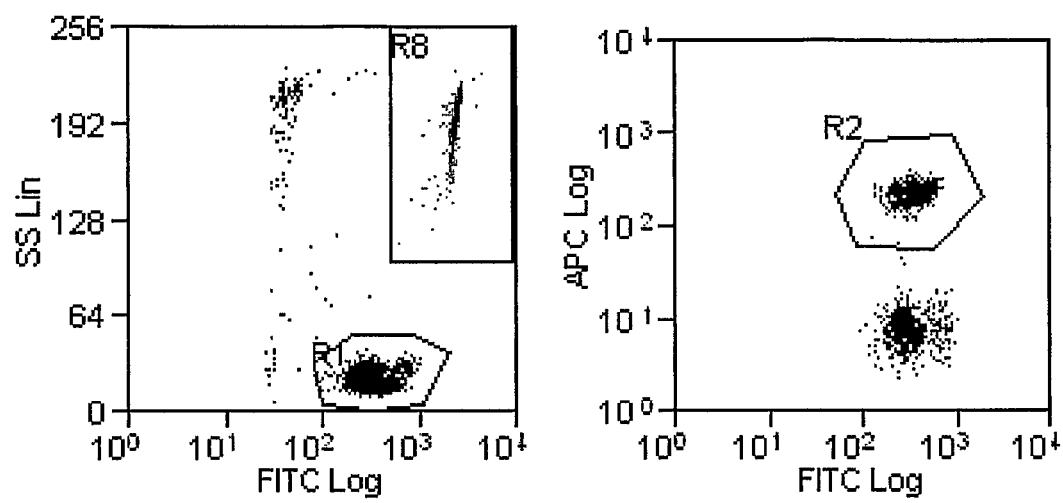
FIGS. 2I-2P show the fluorescence vs. side scatter and fluorescence vs. fluorescence plots of whole blood stained with 4 different 2-colour mixtures in the control (FIGS. 2I, 2K, 2M and 2O) compared to the Matrix (FIGS. 2J, 2L, 2N and 2P) where the conjugates are incorporated in the Matrix.
Figure 2J:
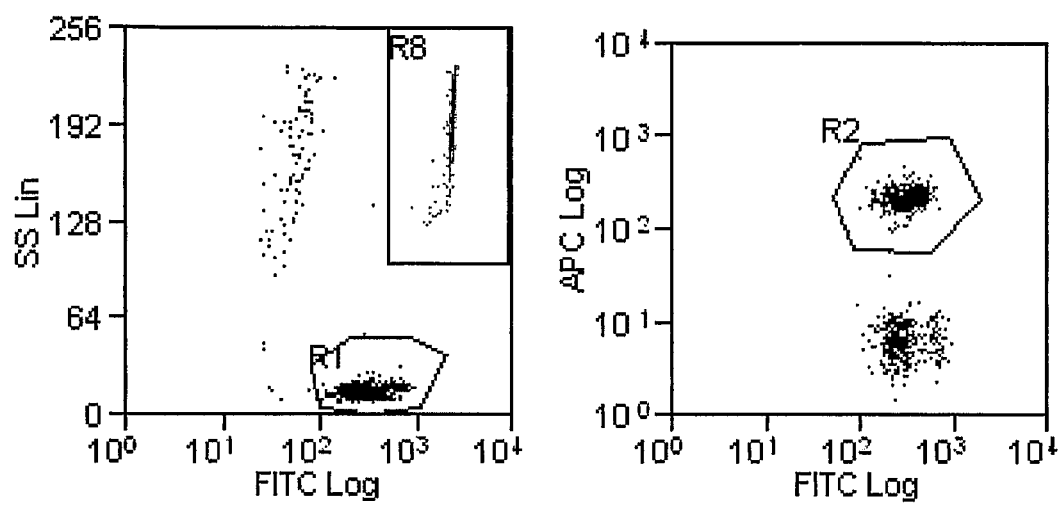

FIGS. 2I and 2J shows the plots for Dual 1 control and matrix, respectively. The plots are CD3-FITC vs. side scatter, where the T-lymphocytes (the bottom centre of the plot) and the beads (upper right side of the plot) are gated and the CD3-FITC vs. CD4-APC plot showing only the T-lymphocytes where the CD4-positive T-lymphocytes are gated.

Figure 2K:
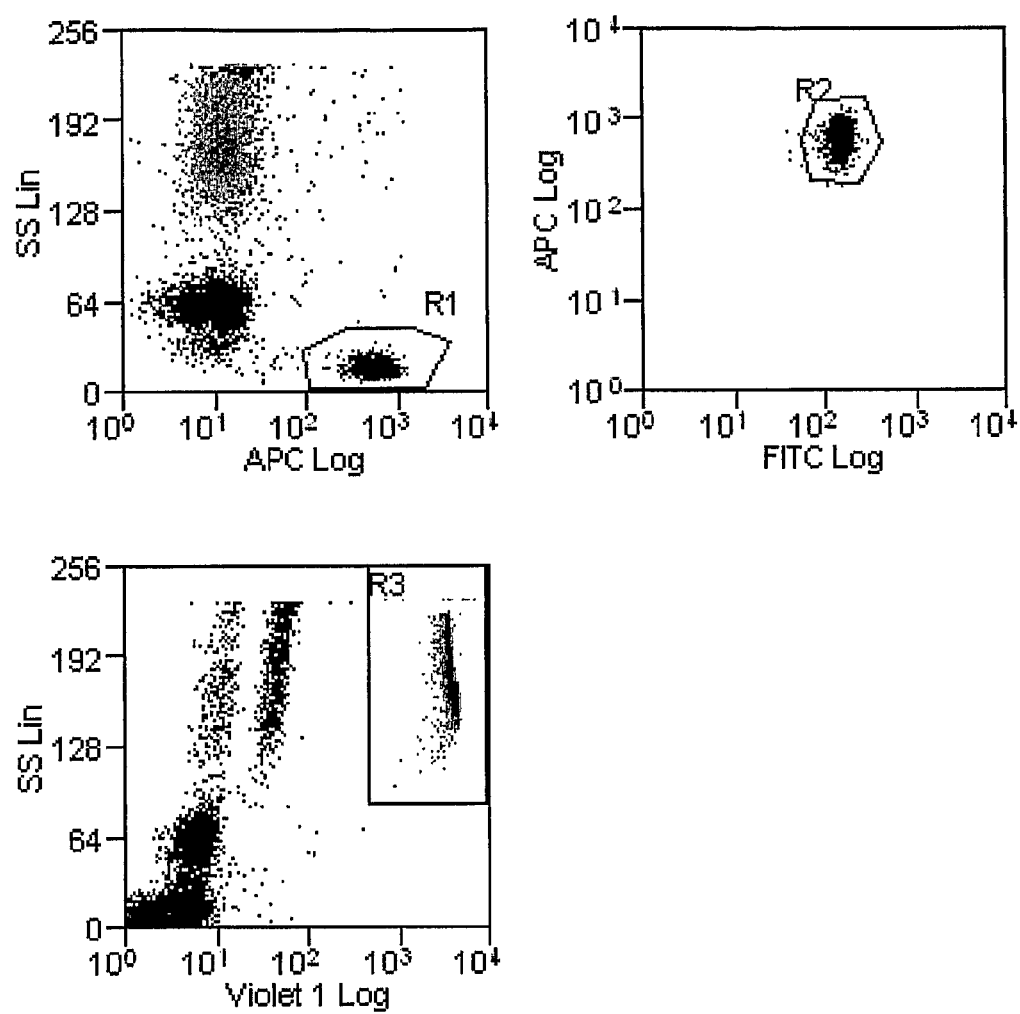
Figure 2L:
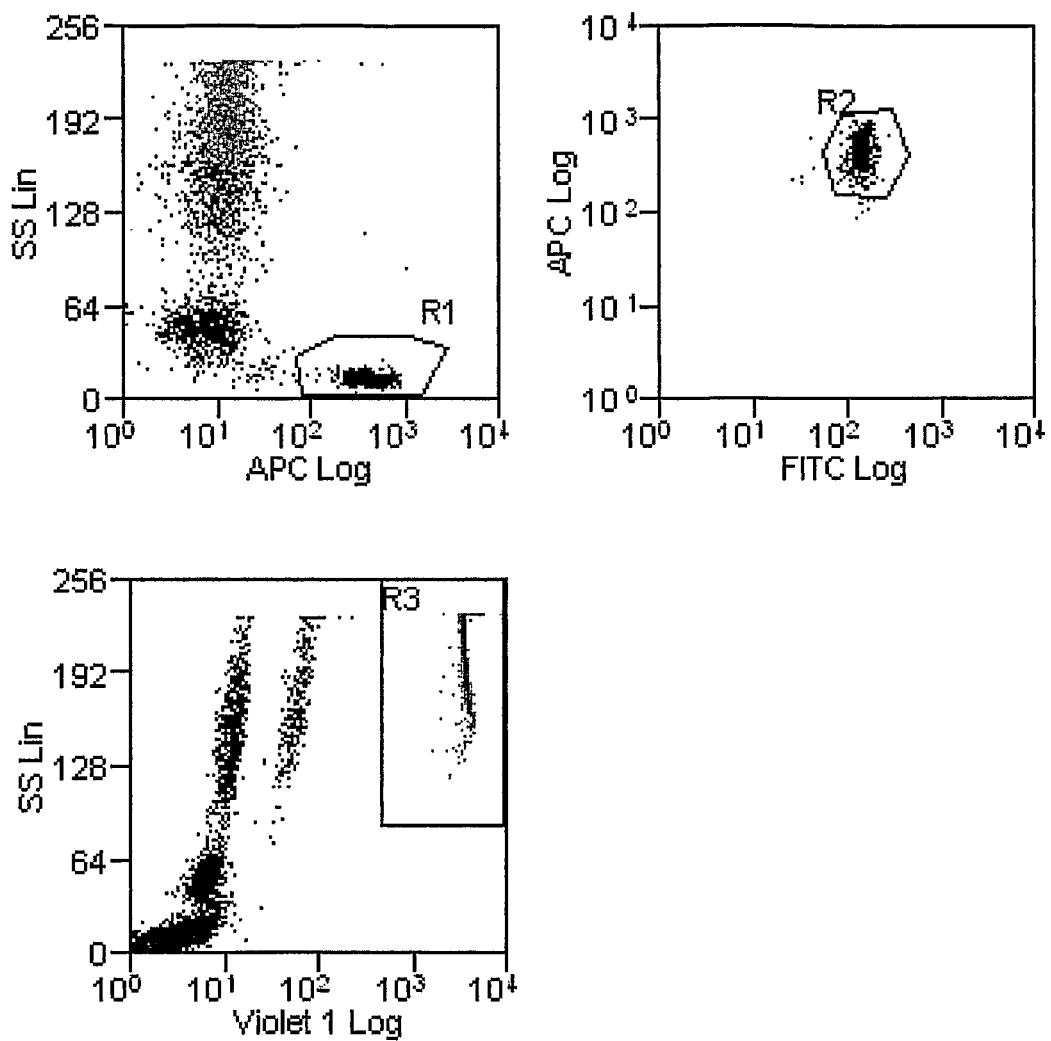

FIGS. 2K and 2L shows the plots for Dual 2 control and matrix, respectively. The plots are CD3-APC vs. side scatter, where the T-lymphocytes (the bottom centre of the plot) are gated, the CD3-APC vs. CD4-FITC plot showing only the T-lymphocytes where the CD4-positive T-lymphocytes are gated and the violet 1 vs. side scatter where the beads are gated.

Figure 2M:
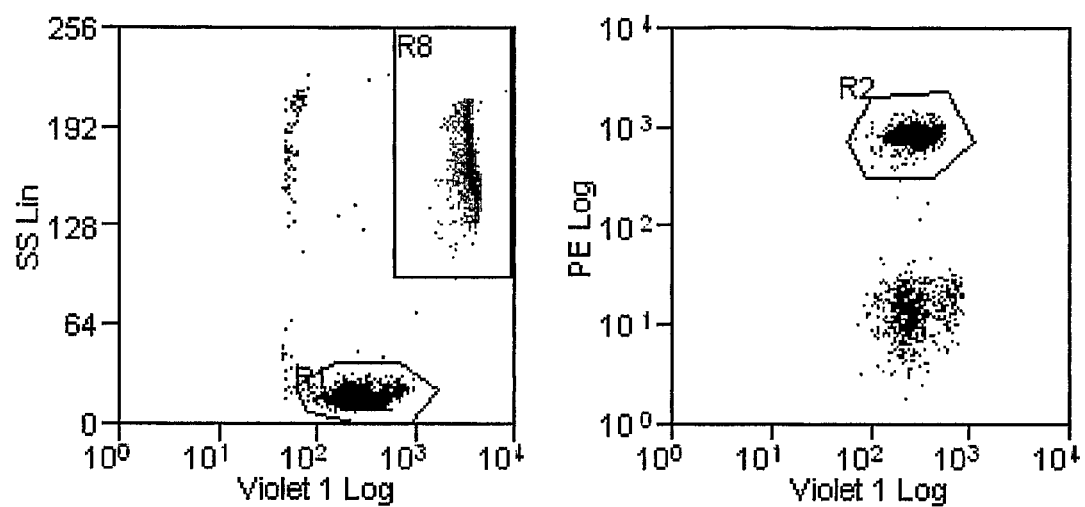
Figure 2N:
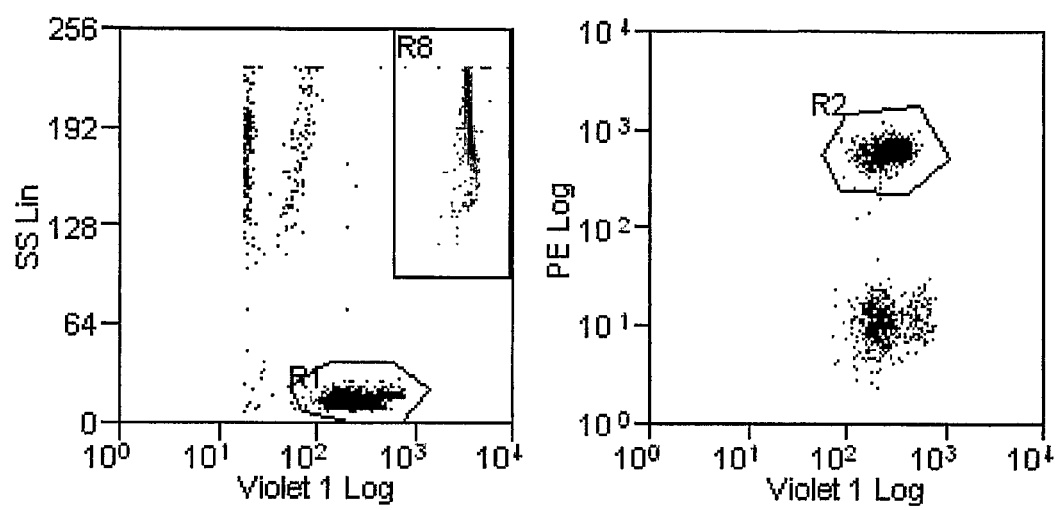

FIGS. 2M and 2N shows the plots for Dual 3 control and matrix, respectively. The plots are CD3-PB vs. side scatter, where the T-lymphocytes (the bottom centre of the plot) and the beads (upper right side of the plot) are gated and the CD3-PB vs. CD4-PE plot showing only the T-lymphocytes where the CD4-positive T-lymphocytes are gated.

Figure 2O:
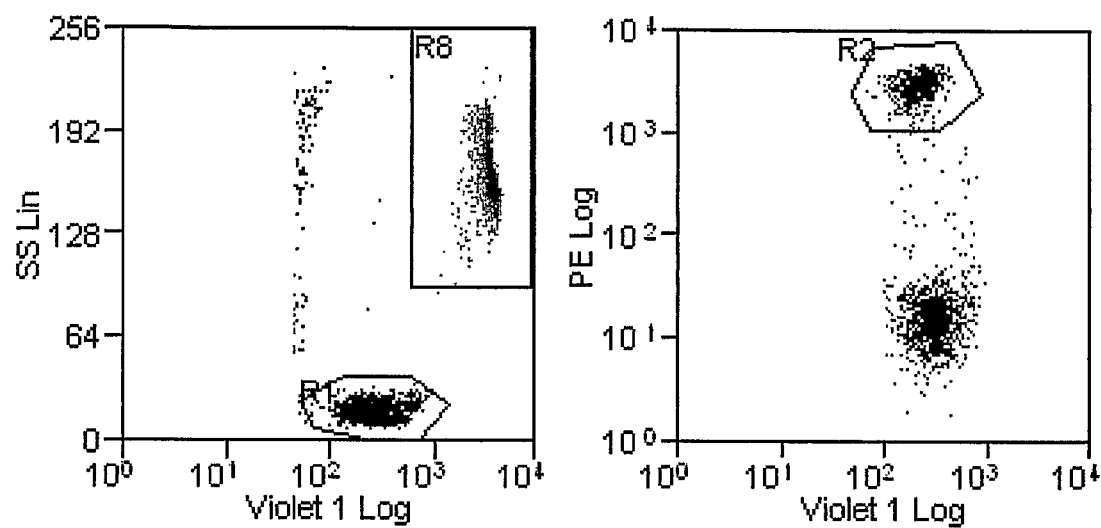
Figure 2P:
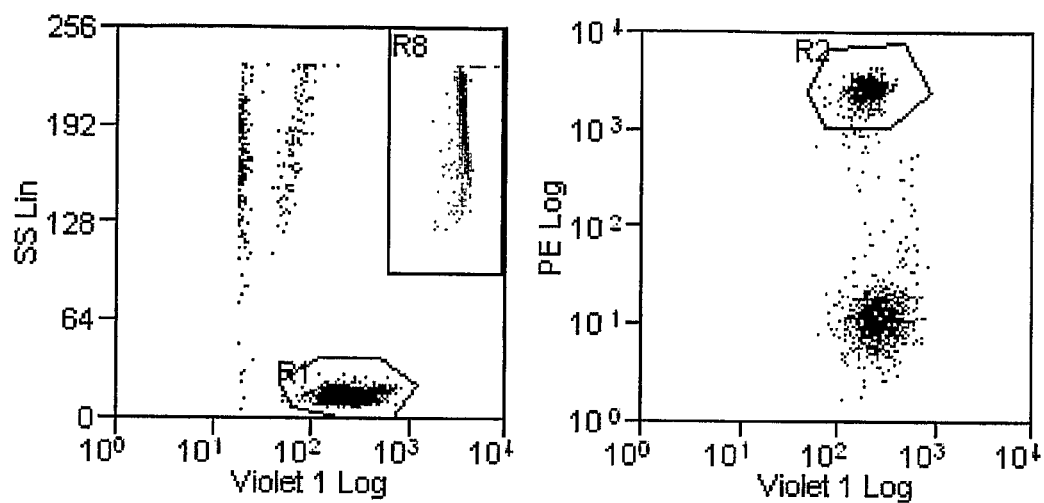
Figure 3A:
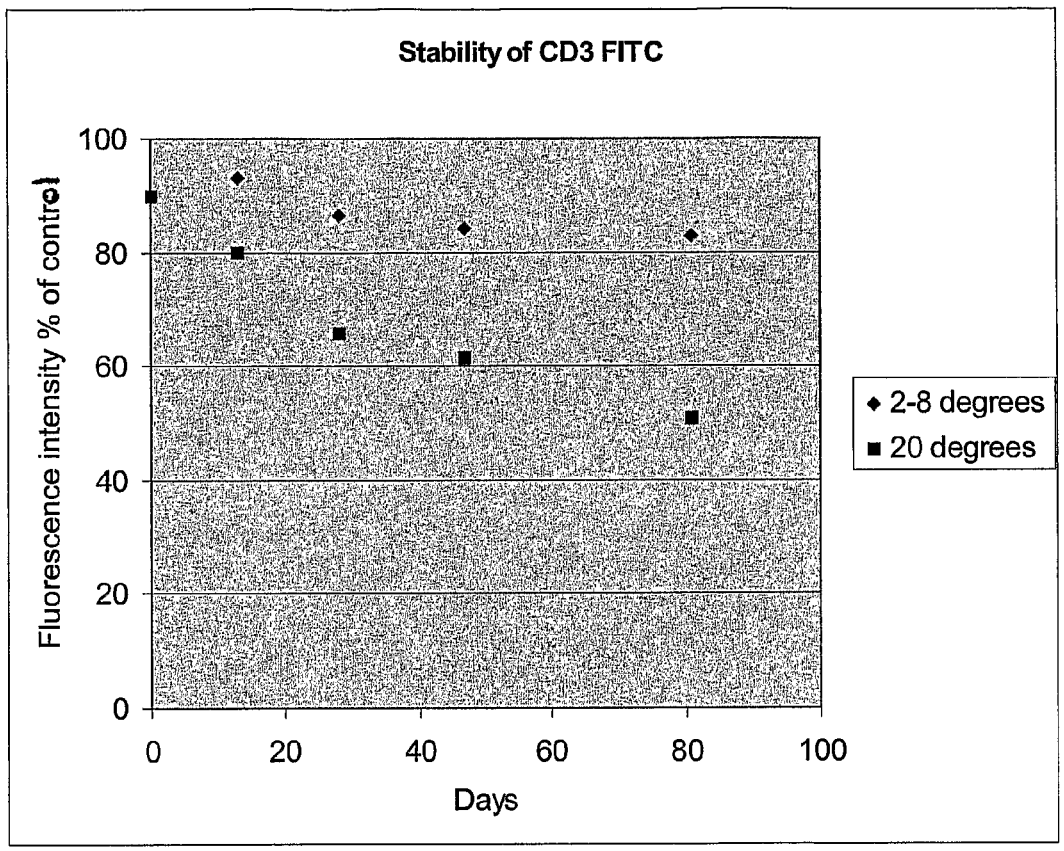
FIGS. 3A-3D show the change in fluorescence intensity in percent of the controls of 4 different antibody-conjugates (CD3 FITC, CD3 RPE, CD3 RPE-Cy5 and CD3 APC) embedded in a Matrix and stored for up to 81 days. The diamond shapes represent storage at 2-8° C., whereas the squares represent storage at 20° C.
Figure 3B:
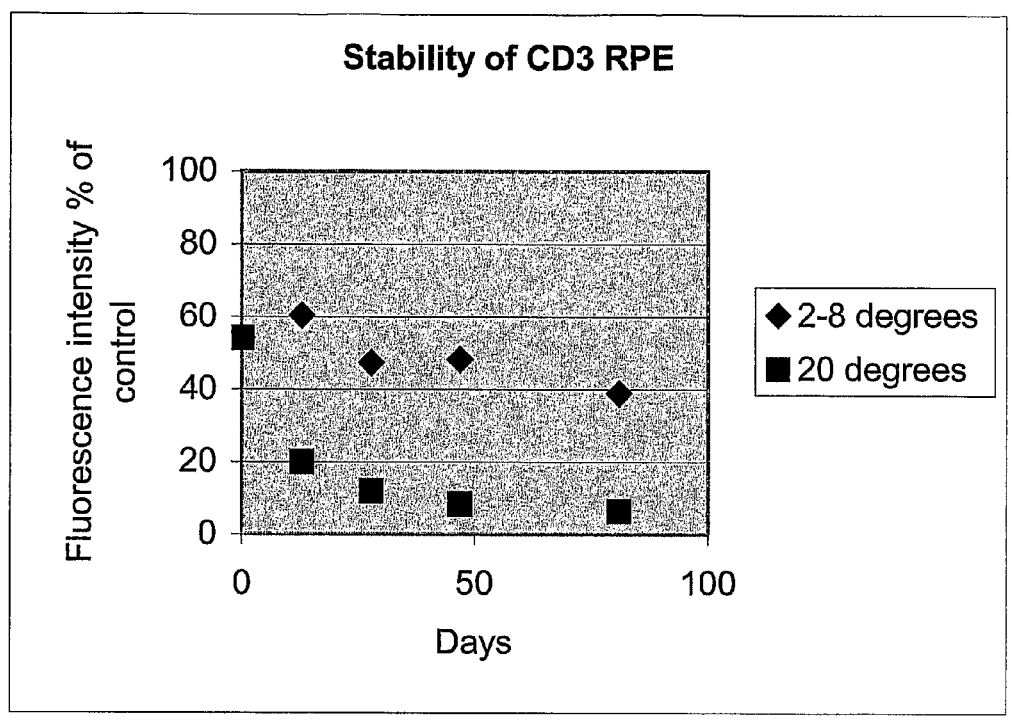
Figure 3C:
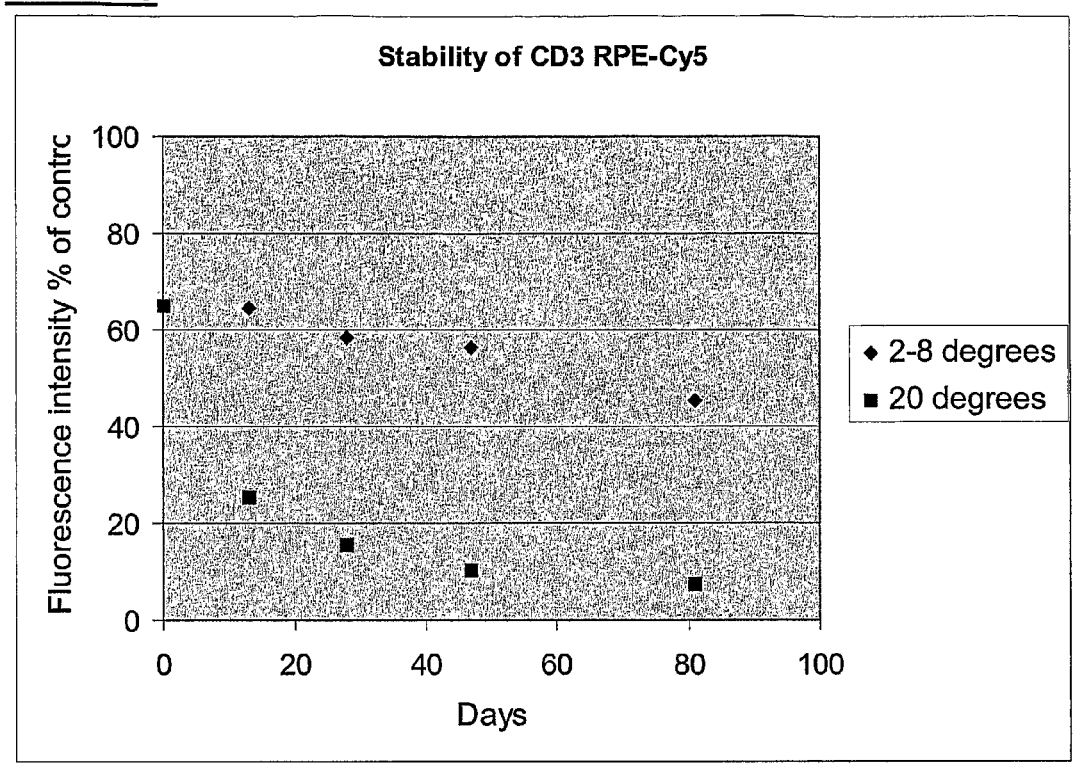
Figure 3D:
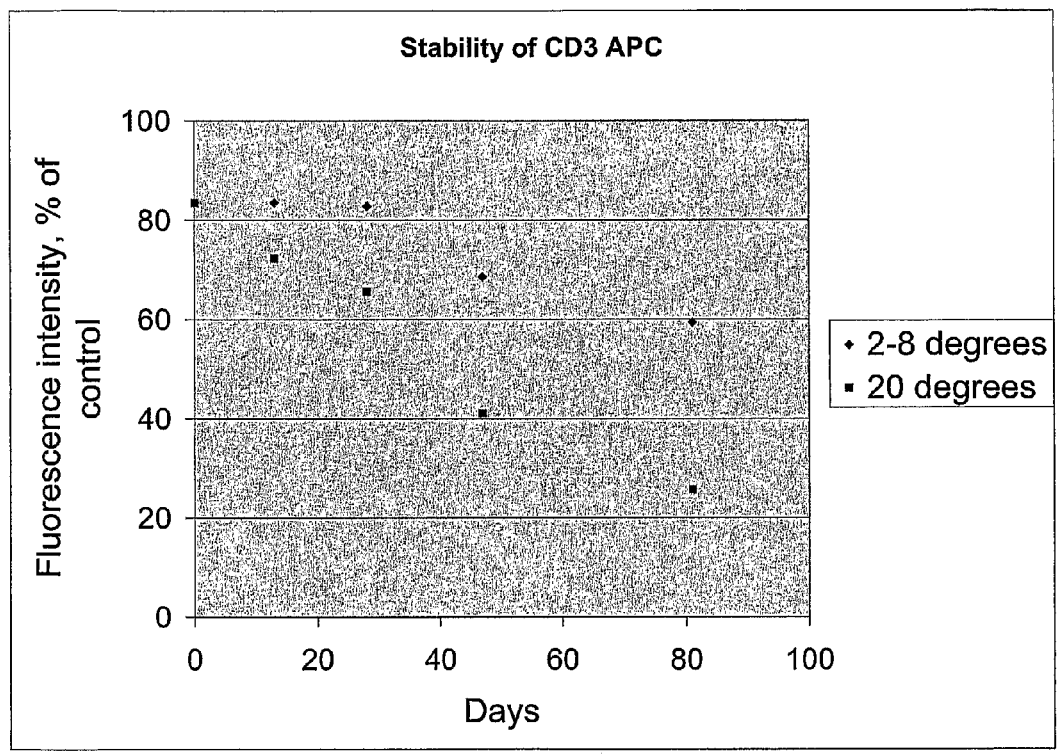
Figure 3E:
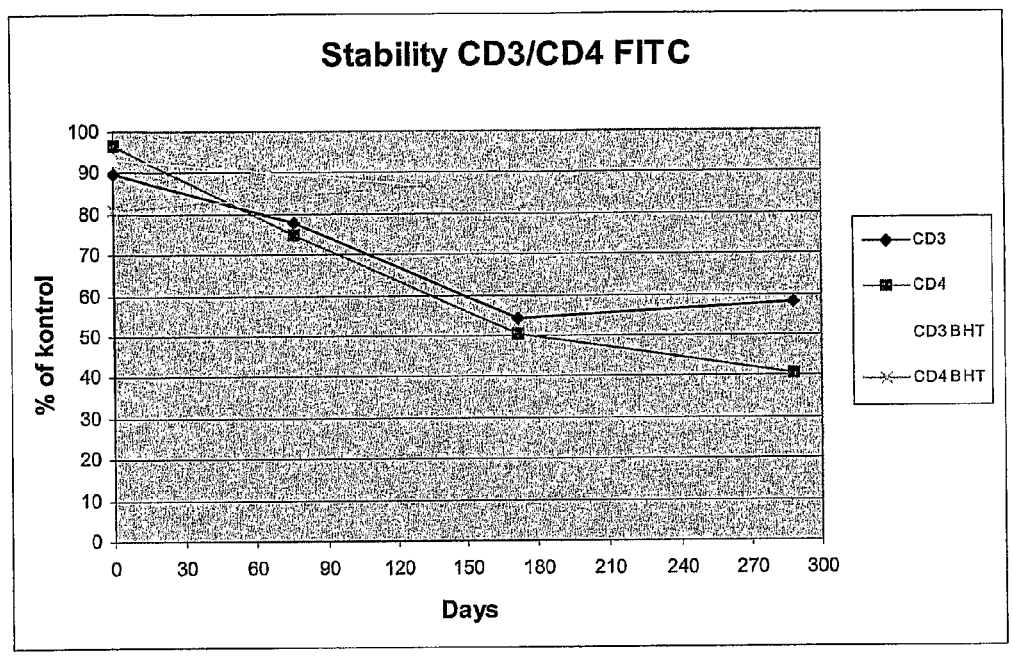
FIGS. 3E-3H show the change in fluorescence intensity in percent of the controls of 4 different 2-colour mixtures (CD3 FITC/CD4-APC, CD3-APC/CD4-FITC, CD3-PB/CD4-RPE and CD3-PB/CD8-RPE) embedded in a Matrix and stored for over 9 months without an antioxidant and over 4 months with an antioxidant.
Figure 3F:
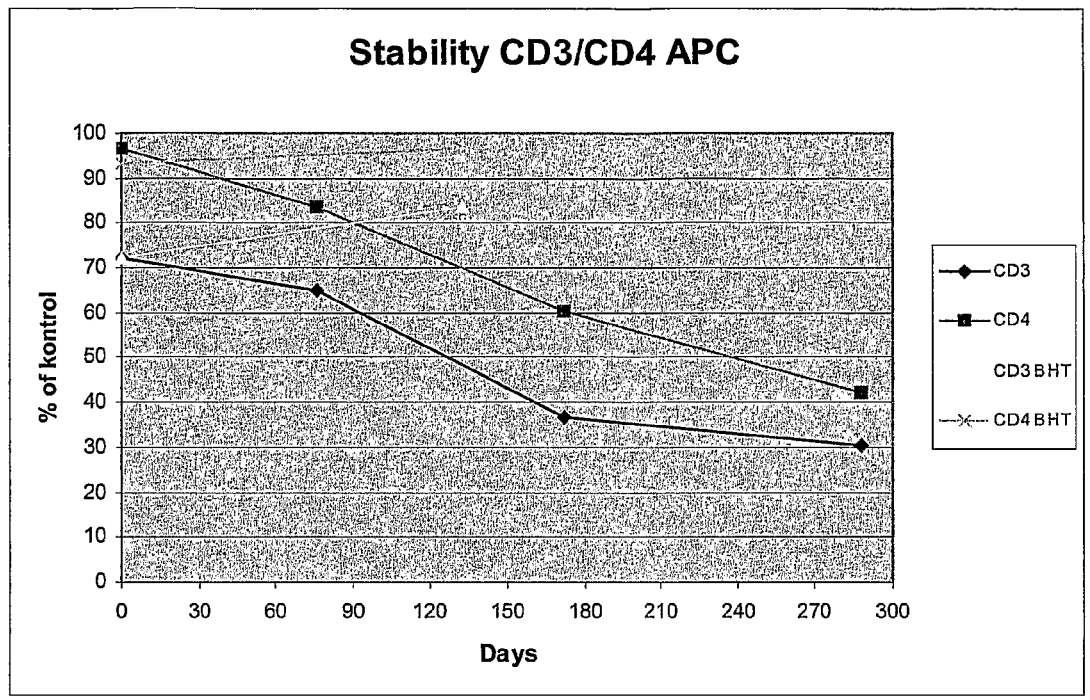
Figure 3G:
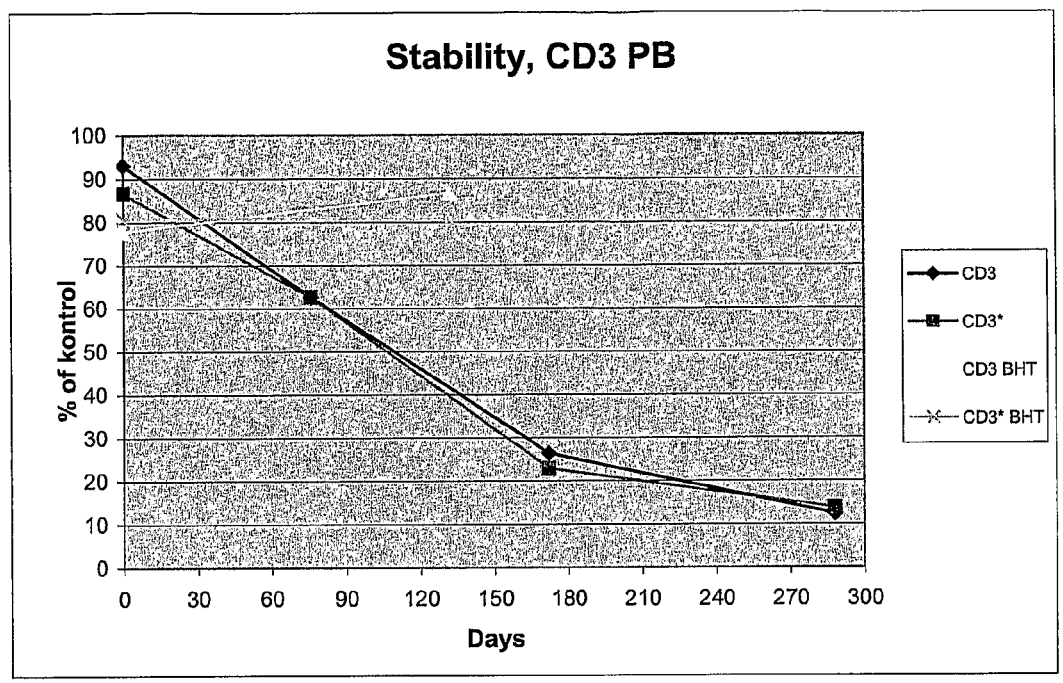
Figure 3H:
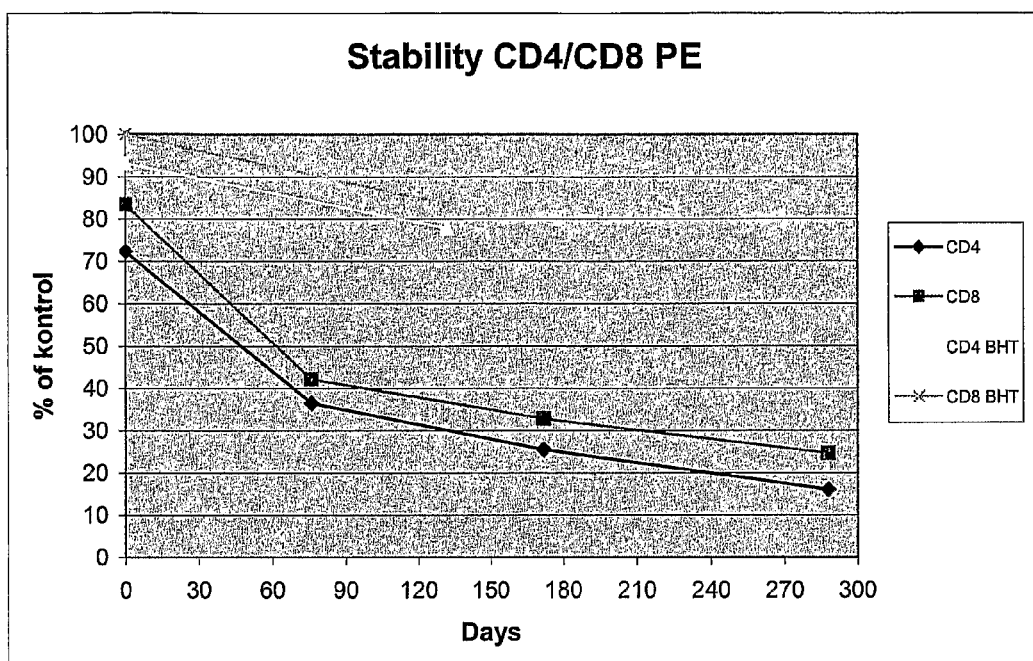
Figure 4A:
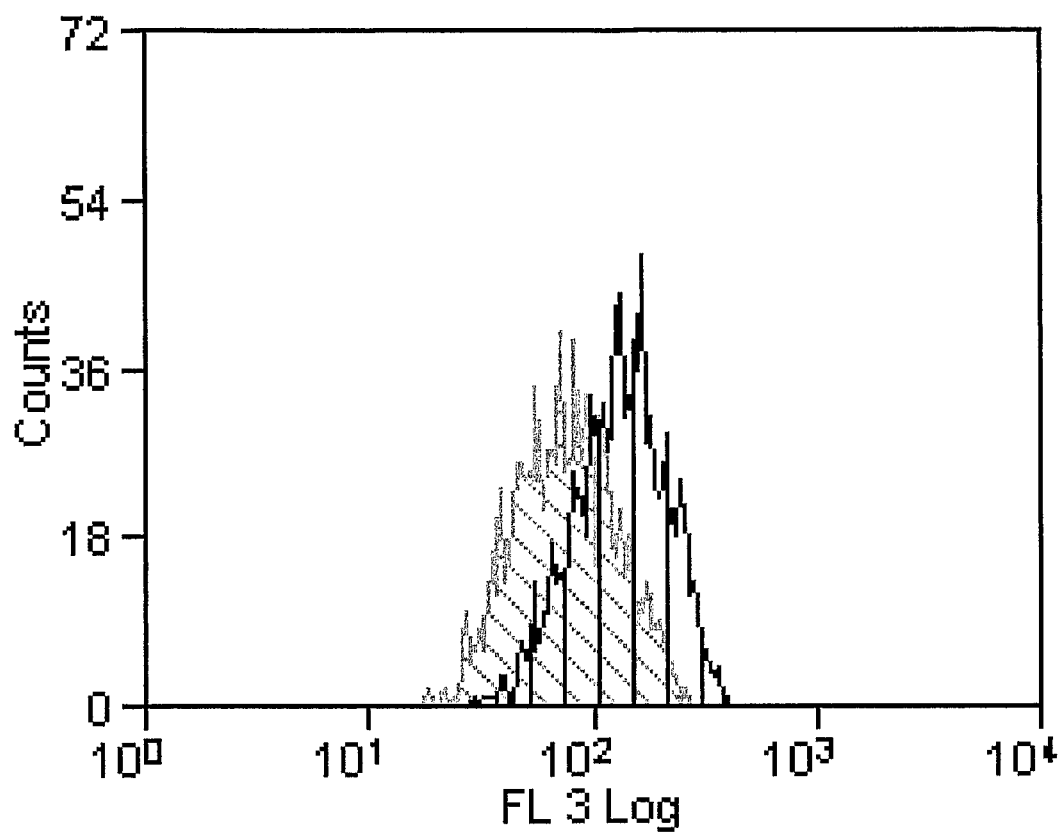
FIGS. 4A-4D show the fluorescent intensity before (Day 0) and after the freezing and heating (Day 8) as described in example 4 for CD3 RPE-A680 and CD4 FITC; comparing in black: Matrix containing beads (4-color mix is added when preparing sample) with in grey: Matrix containing beads and 4-color mix.
Figure 4B:
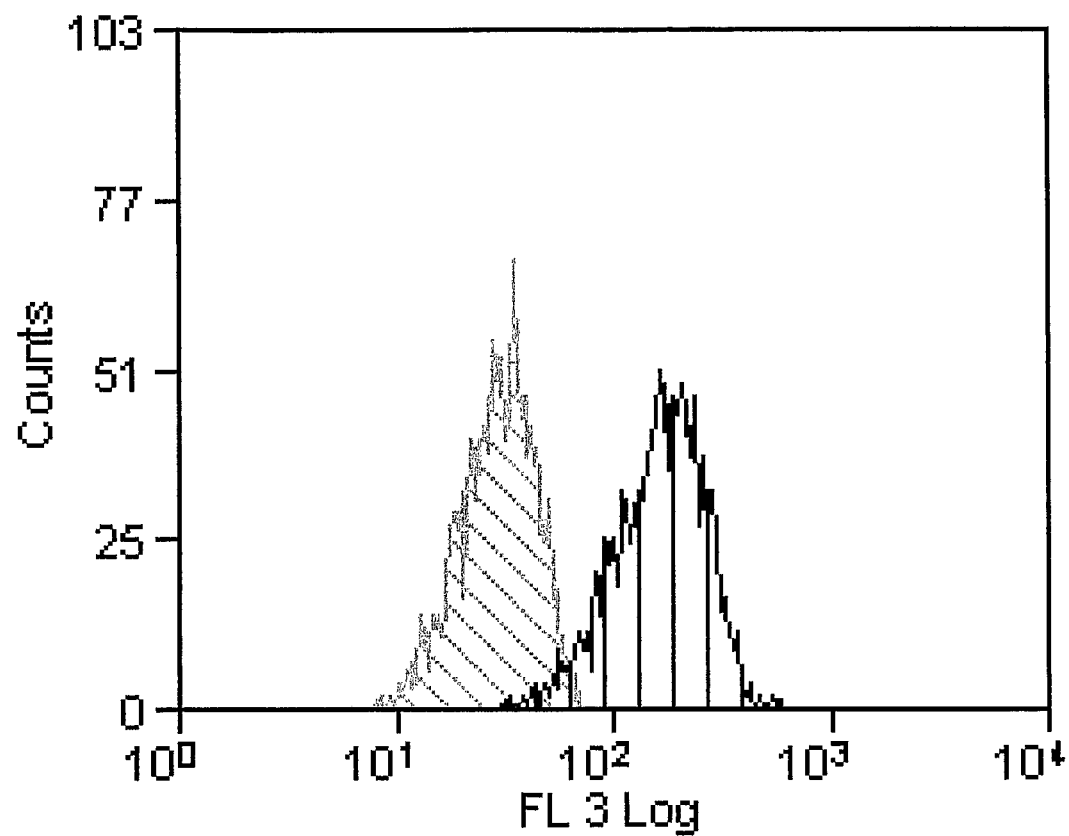
Figure 4C:
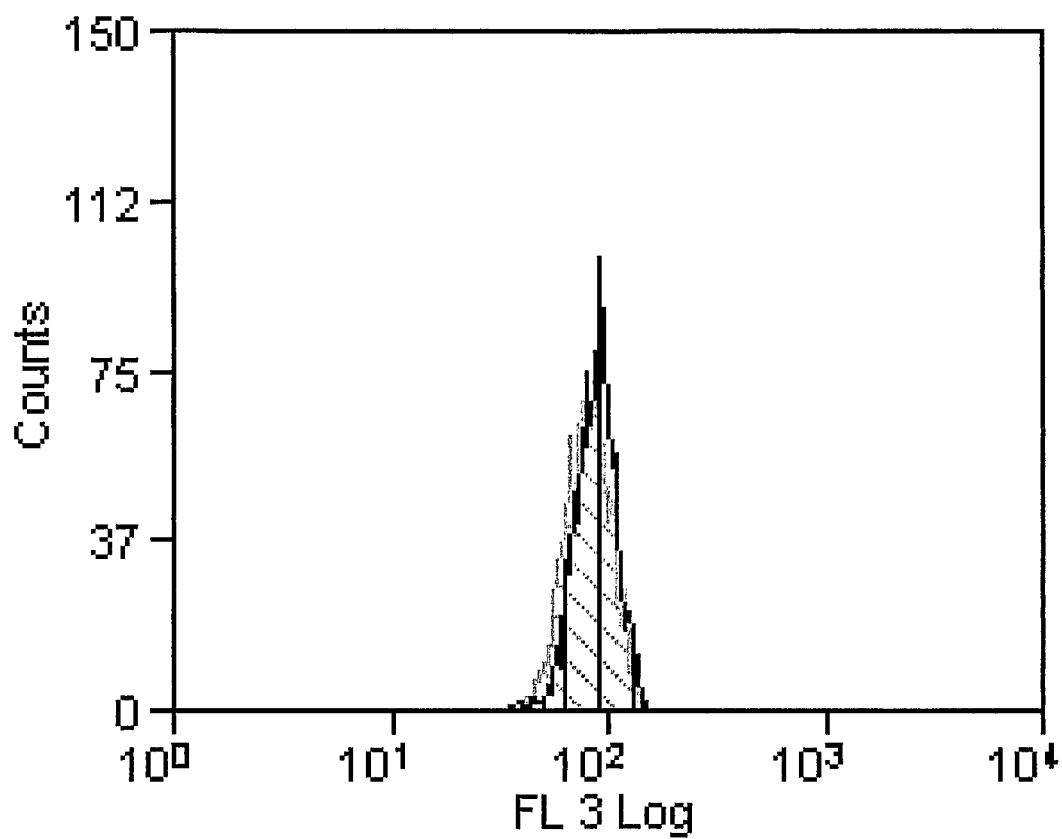
Figure 4D:
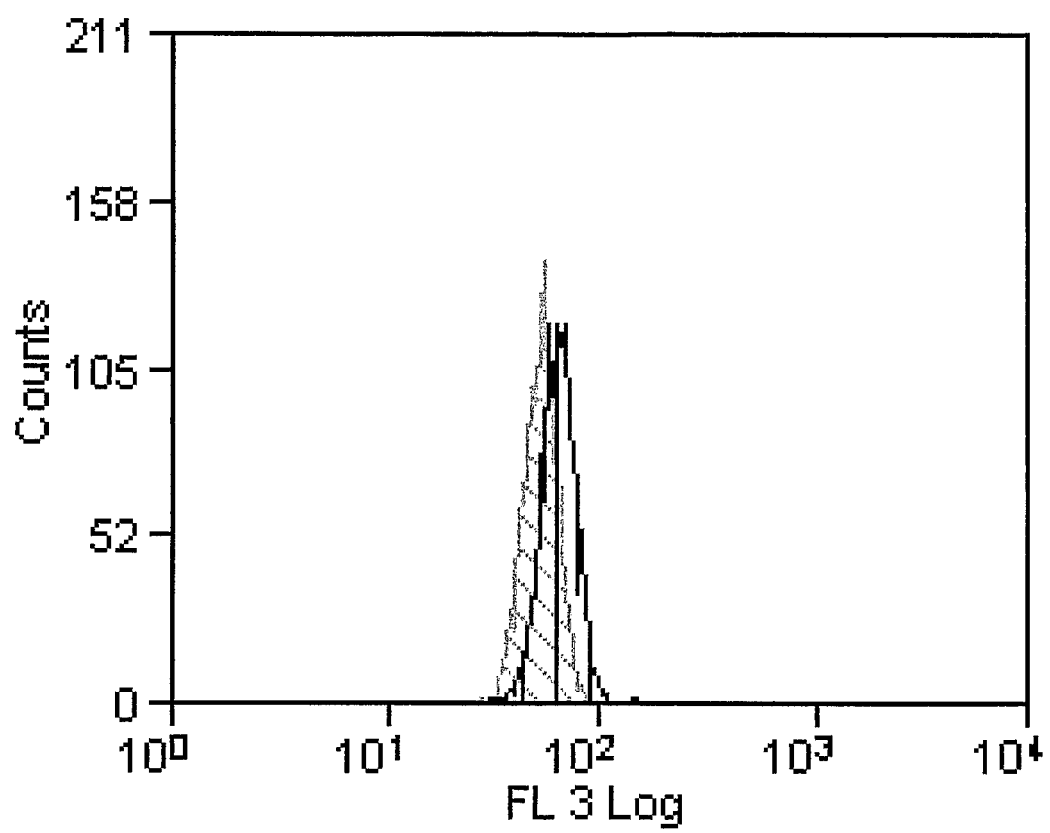
Figure 5A:
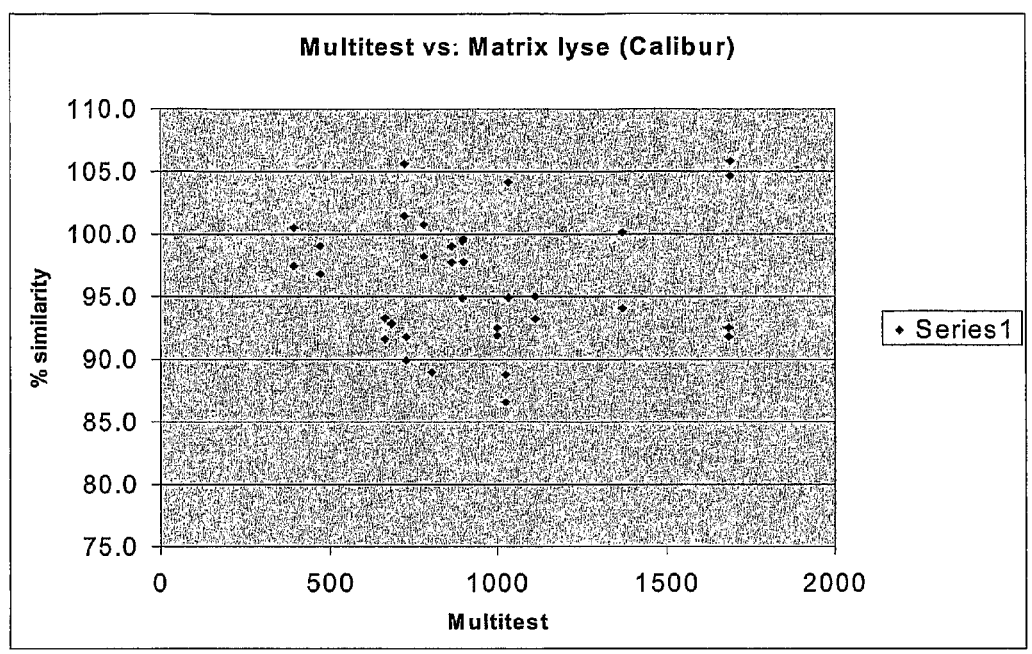
FIGS. 5A-5D show Bland Altman plots of CD4 count obtained with TruCOUNT/MultiTEST compared to lysed and unlysed Matrix samples analysed on both FACSCalibur and Cyan ADP. The percent similarity is calculated as the average of the CD4 counts from TruCOUNT and Matrix divided by the TruCOUNT CD4 count.
Figure 5B:
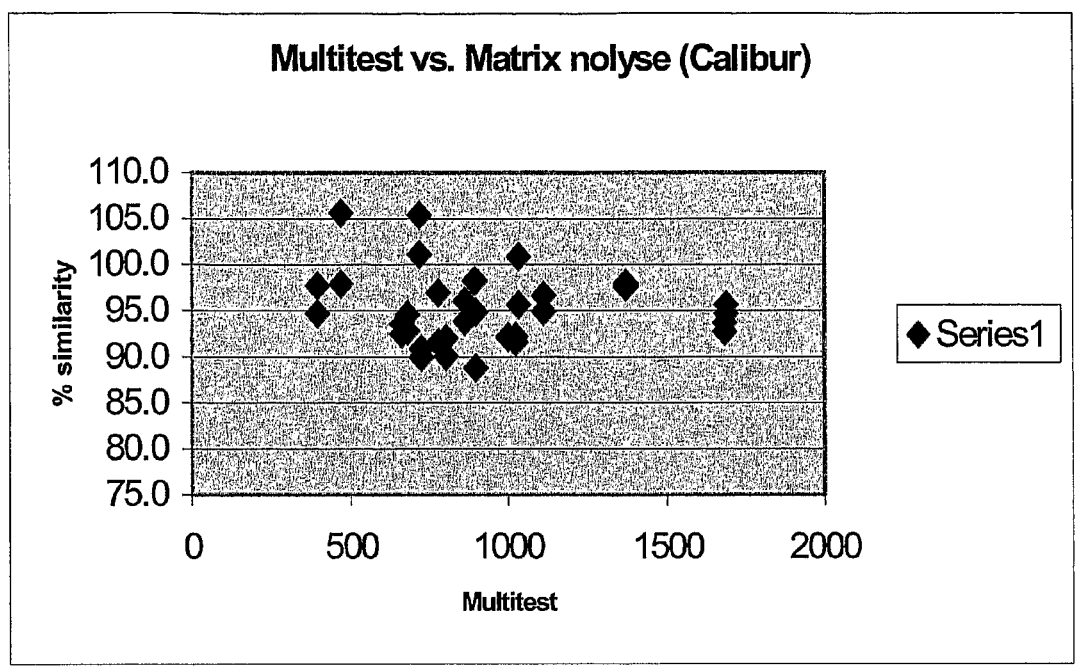
Figure 5C:
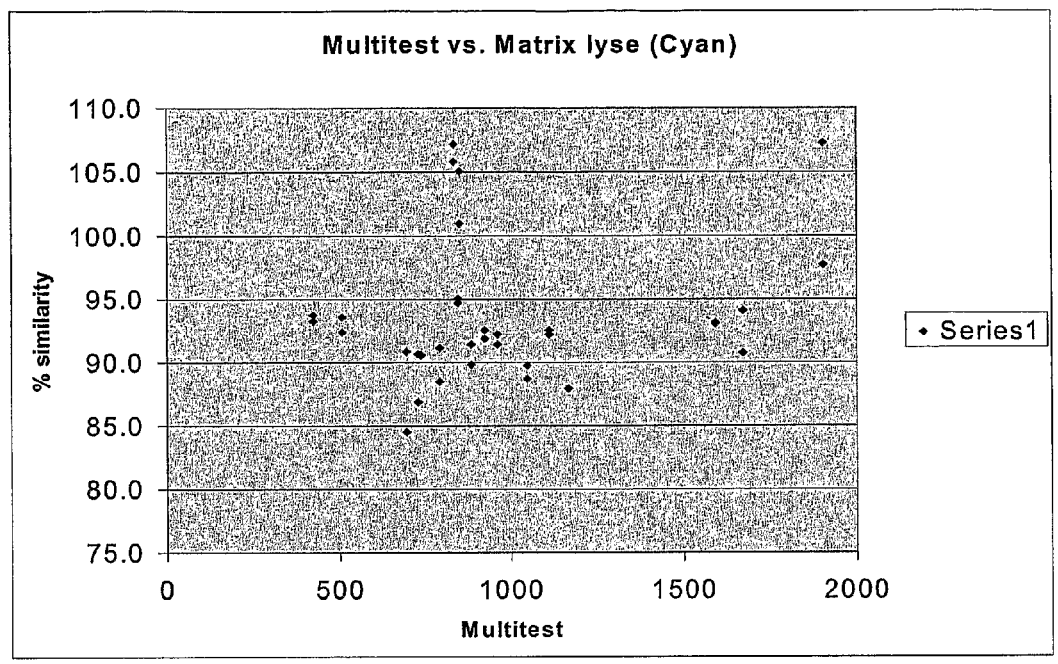
Figure 5D:
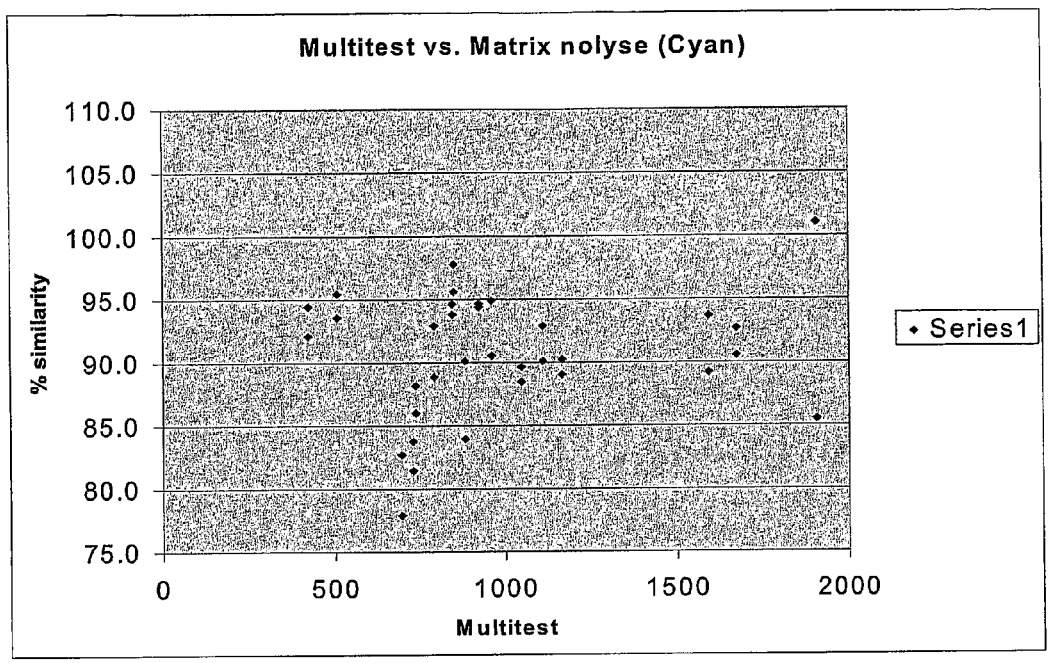
Figure 5E:
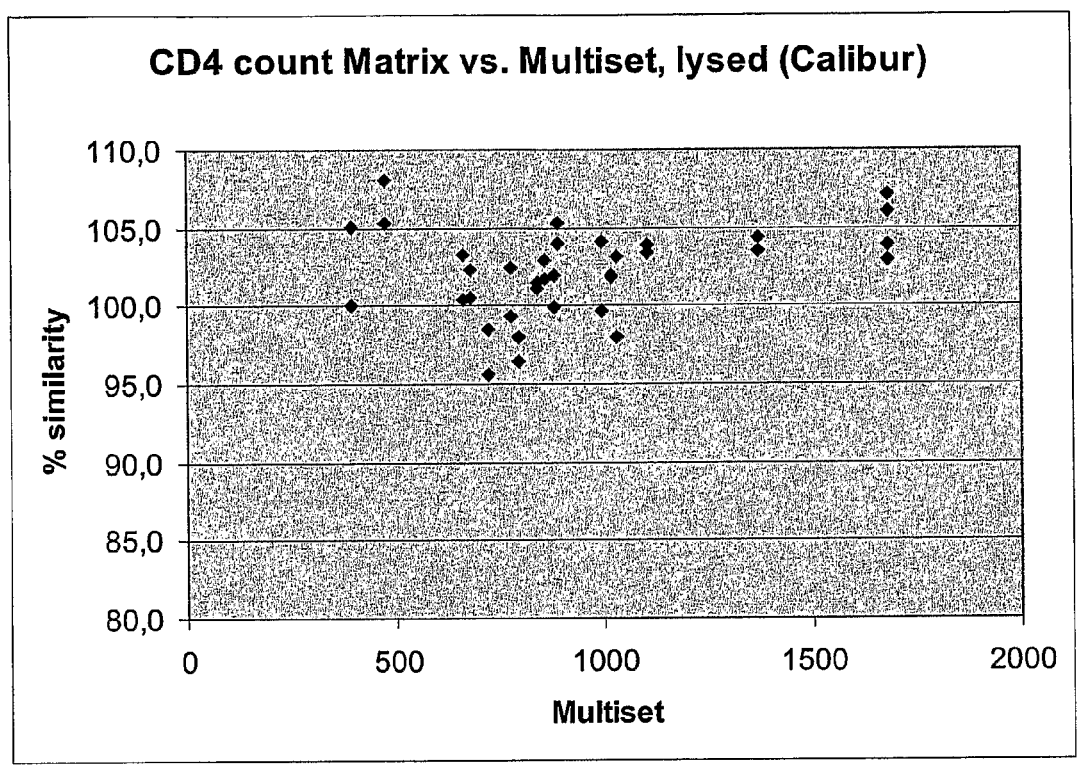
FIGS. 5E-5H: reanalysis of the data from FIGS. 5A-5D, respectively.
Figure 5F:
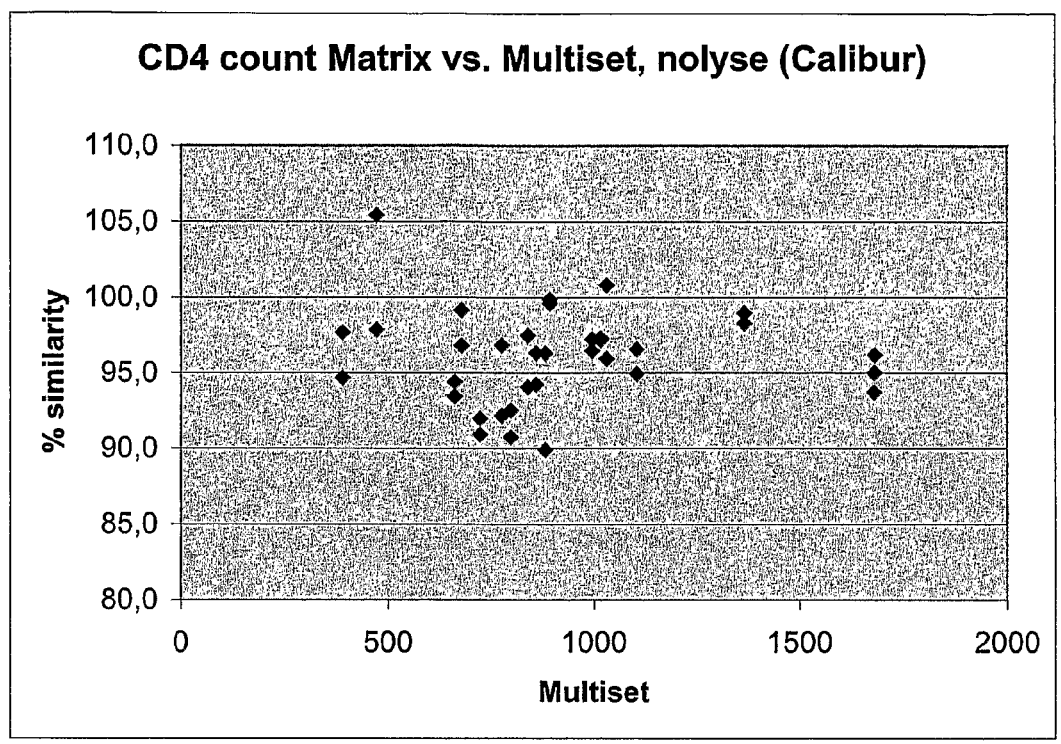
Figure 5G:
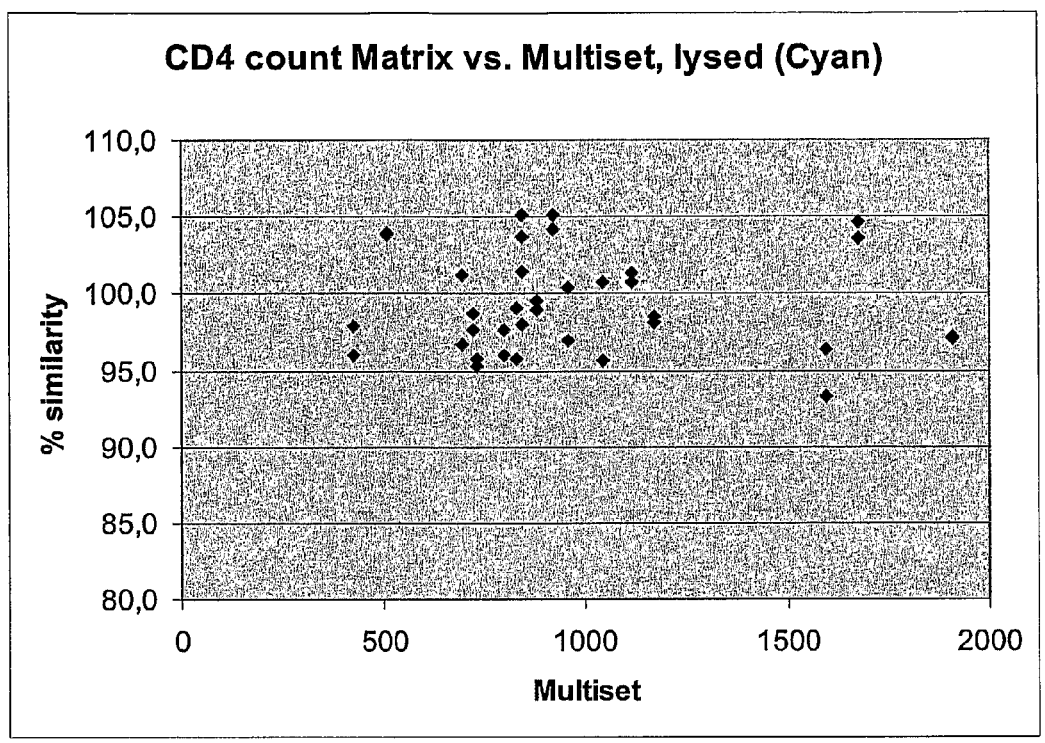
Figure 5H:
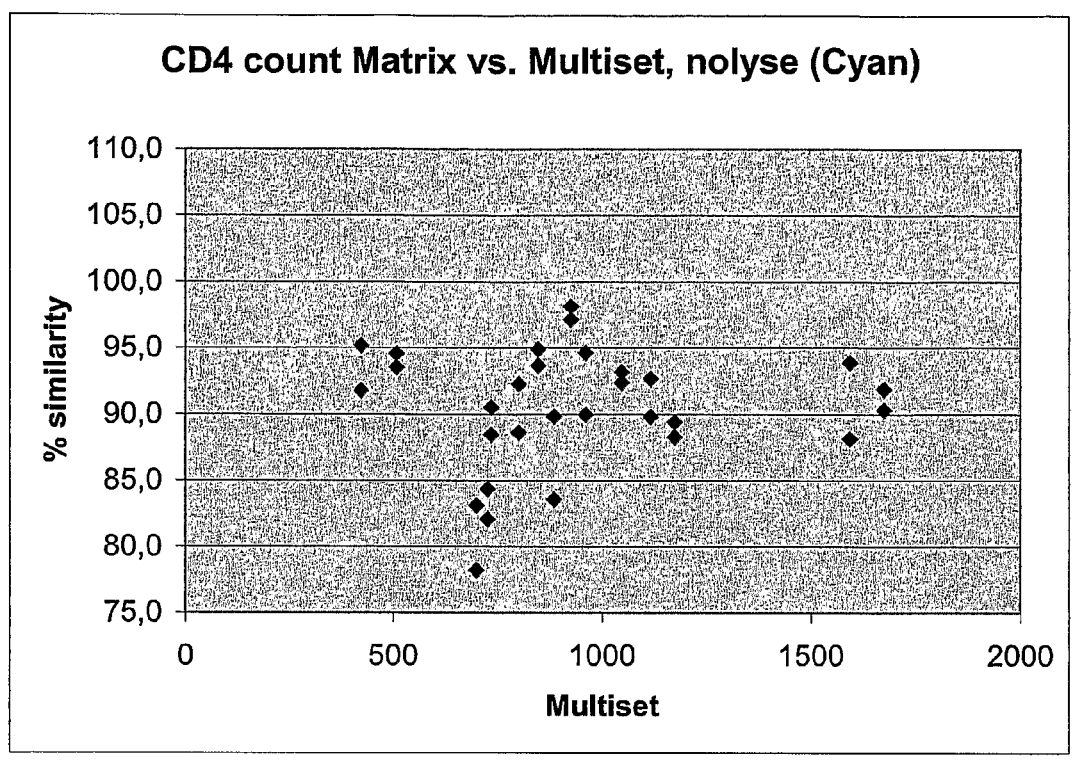
Figure 6A:
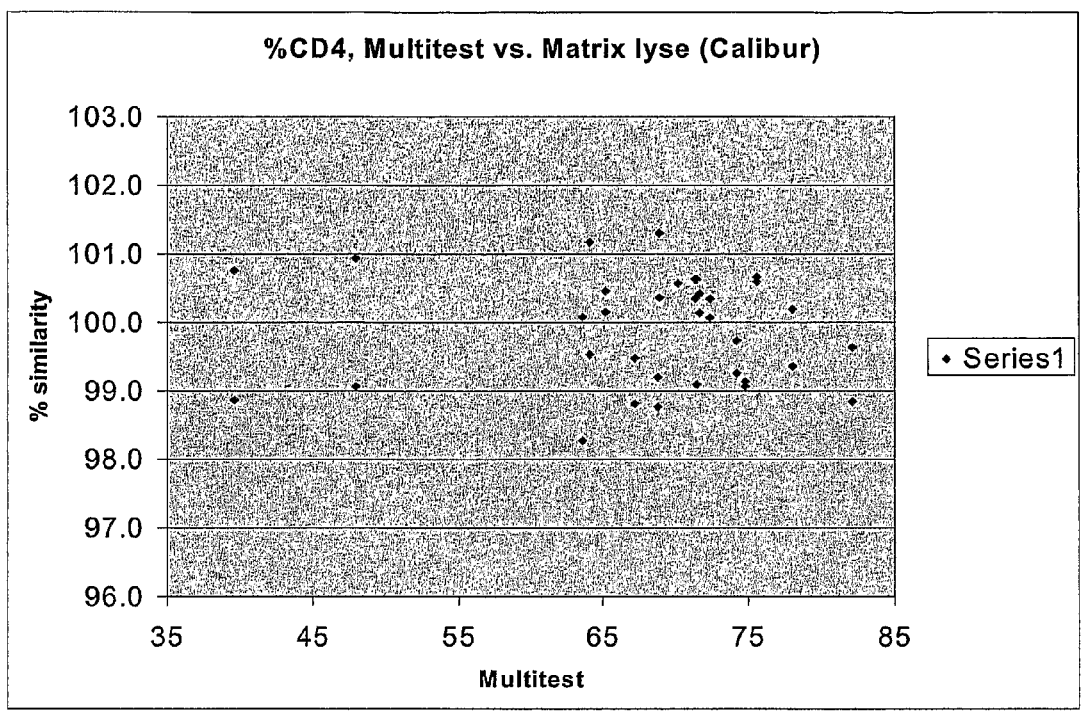
FIGS. 6A-6D show Bland Altman plots of the CD4 percentages (out of CD3-positive cells) for lysed and unlysed Matrix-samples compared to TruCOUNT/MultiTEST, analysed on both FACSCalibur and Cyan ADP. The percent similarity is calculated as in FIG. 5.
Figure 6B:
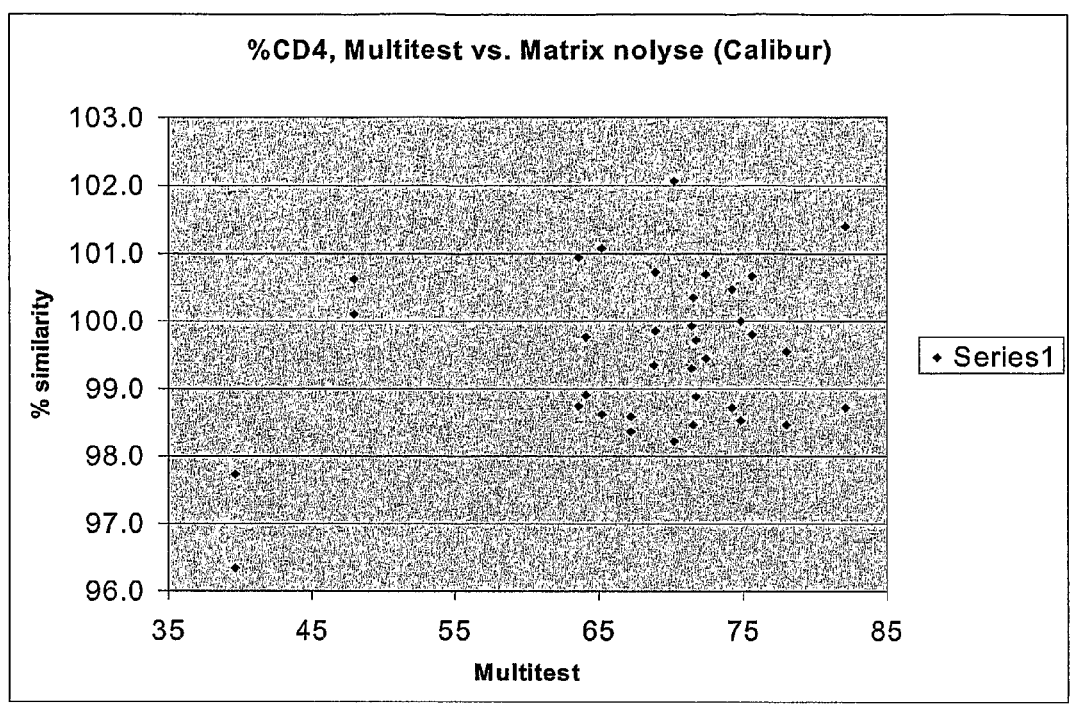
Figure 6C:
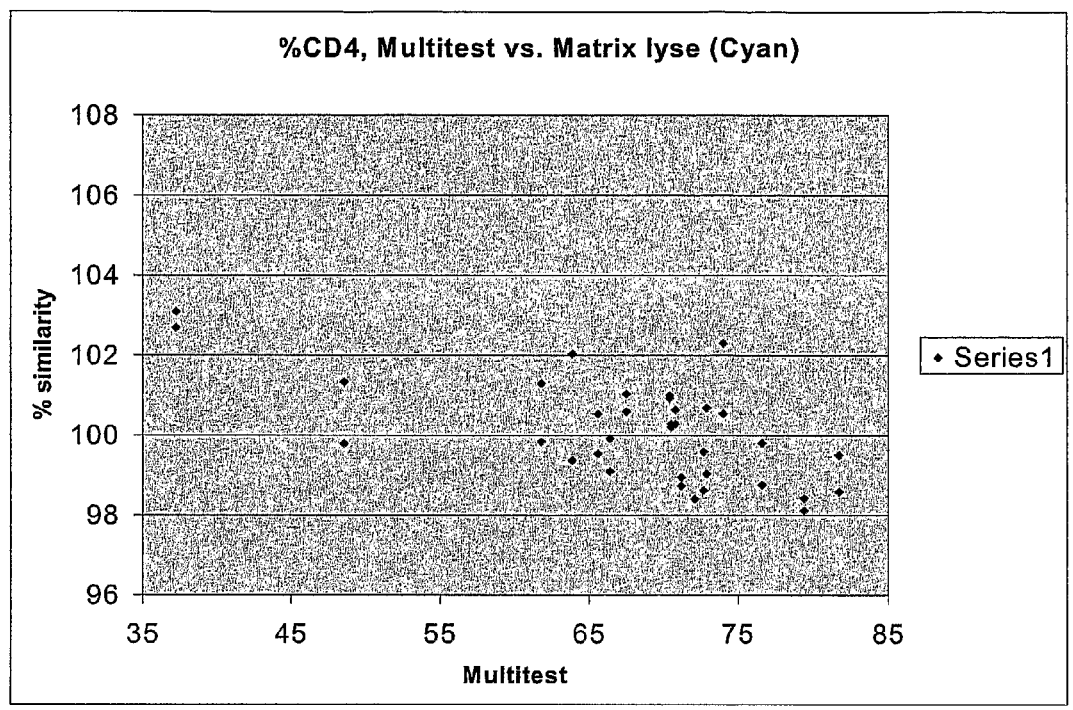
Figure 6D:
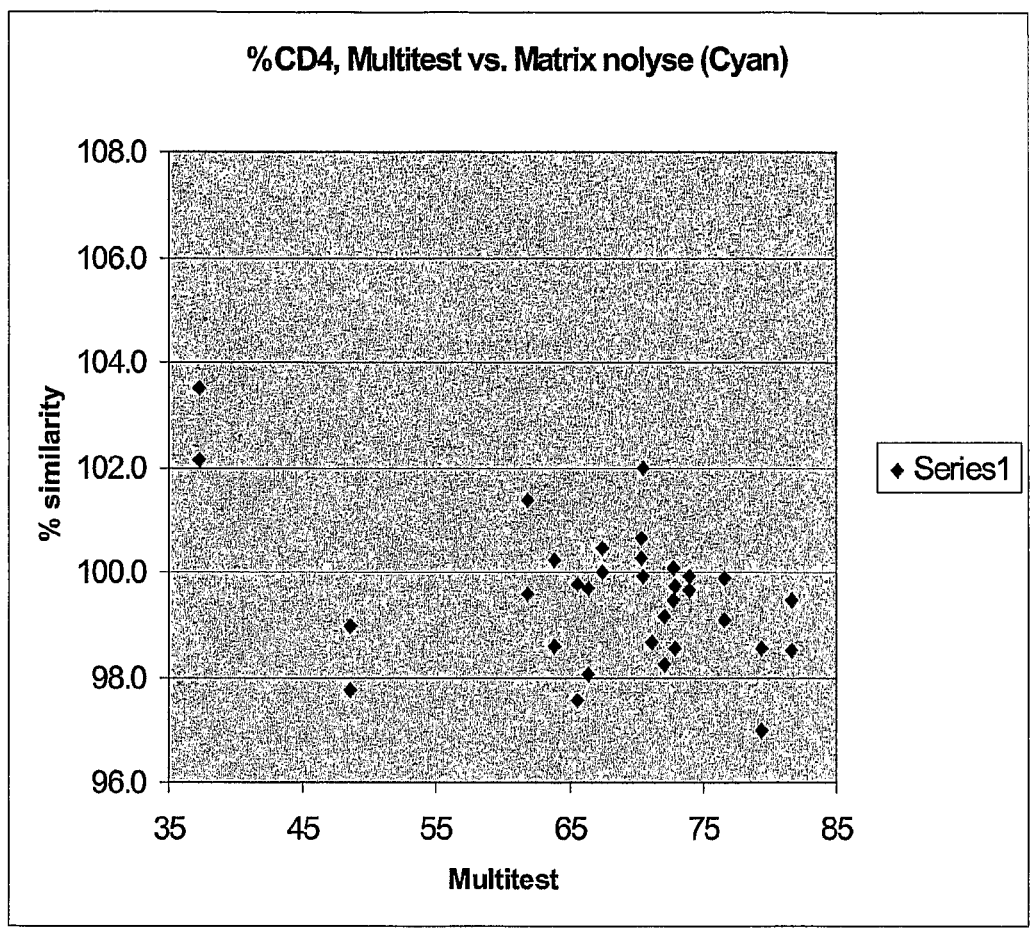

FIGS. 2O and 2P shows the plots for Dual 4 control and matrix, respectively. The plots are CD3-PB vs. side scatter, where the T-lymphocytes (the bottom centre of the plot) and the beads (upper right side of the plot) are gated and the CD3-PB vs. CD8-PE plot showing only the T-lymphocytes where the CD8-positive T-lymphocytes are gated.

The fluorescence intensities are in all cases comparable, and there are no problems with separating the CD3-positive populations (dense population centred at the bottom of the plots) from the negative populations or separating the CD4-positive lymphocytes from the negative.

TABLE 6

Median fluorescent intensities determined in Example 3A

| Two-colour mix | Antibody-conjugate | Control | Matrix | Matrix/Control % |
| --- | --- | --- | --- | --- |
| Dual 1 | CD3-FITC | 339.8 | 305.1 | 89.8 |
| | CD4-APC | 212.9 | 205.4 | 96.5 |
| Dual 2 | CD3-APC | 604.3 | 437.1 | 72.3 |
| | CD4-FITC | 154.0 | 148.6 | 96.5 |
| Dual 3 | CD3-PB | 273.8 | 254.8 | 93.1 |
| | CD4-RPE | 805.8 | 582.9 | 72.3 |
| Dual 4 | CD3-PB | 273.8 | 237.1 | 86.6 |
| | CD8-RPE | 2838.7 | 2371.4 | 83.5 |

Summary

The antibody-conjugates that are incorporated in the matrix displayed fluorescent intensities that are comparable to the controls and allowed for easy and unambiguous gating of the CD3+ CD4+ or CD3+ CD8+ populations.

Example 4

Storage Stability of Matrix Embedded Antibody-Conjugates

This Example describes the storage stability of antibody-conjugates in the Matrix.

Procedure 36 matrices are prepared according to procedure B in Example 1 with 100 µL CytoCount™ beads and 10 µL CD3 FITC, CD3 RPE, CD3 RPE-CY5 and CD3 APC in 9 tubes each, i.e. only one antibody-conjugate per Matrix-tube and 9 tubes with each antibody-conjugate. 16 tubes (4 with each antibody-conjugate) are stored at 2-8° C. and 16 are stored at 20° C. The last 4 are analysed immediately after drying. 8 tubes are analysed after 13, 28, 47 and 81 days, two with each antibody-conjugate, one stored at 2-8° C. and one stored at 20° C.

Preparing the Matrix Samples Along with the Corresponding Controls

1. To 4 new Falcon tubes added 10 µL CD3 FITC, CD3 RPE, CD3 RPE-CY5 and CD3 APC respectively. These are the controls.
2. To all 12 tubes (4 controls and 8 Matrix-tubes) is added 100 µL of whole blood specimen.
3. The samples are vortexed and incubated in the dark for 15 min. at room temperature.
4. The samples are lysed with Uti-Lyse™ according to procedure D, Example 1.

For the controls, 100 µL of CytoCount™ beads are added immediately prior to analysing. All samples are vortexed for 5 seconds immediately before analysing. All the samples are analysed on a FACSCalibur™ flow cytometer with Cellquest™ software version 3.3.

Results

The results are shown in FIGS. 3A, 3B, 3C and 3D.

FIGS. 3A-D show the change in fluorescence intensity in percent of the controls of 4 different antibody-conjugates stored in a Matrix for up to 81 days. The diamond shapes represent storage at 2-8° C., whereas the squares represent storage at 20° C.

The stability of the antibody-conjugates in the matrix is similar to the stability of the conjugates in aqueous solution. The gating is unaffected by storage at 2-8° C. in the dark, which are the storage conditions normally recommended for antibody-conjugates. This is an important property considering the practical use of the ready-to-use reagent Summary All conjugates show sufficient stability when stored at 2-8° C.

Example 4A

Storage Stability of Matrix Embedded Antibody-Conjugates (Two-Colour Mixtures)

This Example describes the storage stability of antibody-conjugates in the Matrix.

Procedure 4 two-colour mixtures are prepared as described in Example 3A.

16 matrices are prepared according to procedure B in Example 1 with 50 µL CytoCount™ beads and 5 µL Dual 1, Dual 2, Dual 3 and Dual 4 in 6 tubes each, i.e. only one antibody mixture per Matrix-tube and 4 tubes with each antibody mixture. The rest of the antibody mixtures are stored at 2-8° C. along with the matrix tubes. After drying 12 tubes are stored at 2-8° C. The last 4, one with each mixture, are analysed immediately after drying. The rest are analysed after 76, 172, 288 days, 4 at a time, one with each antibody mixture.

With the same two-colour antibody mixtures another 8 matrices are prepared according to the procedure in example 2 with 50 µL CytoCount™ beads and 5 µL Dual 1, Dual 2, Dual 3 and Dual 4 in 2 tubes each. A saturated solution of butylated hydroxytoluene (BHT) is made and 100 µL is added to each tube Immediately after drying the first 4 tubes (one with antibody mixture) are analysed. The other 4 are stored for 132 days at 2-8° C. and are then analysed.

Preparing the Matrix Samples Along with the Corresponding Controls for Each Analysis.

1. To 4 new Falcon tubes is added 5 µL Dual 1, Dual 2, Dual 3 and Dual 4 respectively from the mixtures used to make the matrix tubes to be tested. These are the controls.

2. To all 8 tubes (4 controls and 8 Matrix-tubes) is added 50 µL of whole blood specimen.

3. The samples are vortexed and incubated in the dark for 15 min. at room temperature.

4. The samples are lysed with Uti-Lyse™ according to procedure D, Example 1.

For the controls, 50 µL of CytoCount™ beads are added immediately prior to analysing. All samples are vortexed for 5 seconds immediately before analysing. All the samples are analysed on a Cyan™ ADP with Summit v4.2 software to determine the count of CD3+CD4+ or CD3+CD8+ cells. The threshold is set on CD3 except for Dual 2, where it is set on CD4, since the beads are not positive in the APC-channel. The median fluorescence intensity for each antibody-conjugate is determined and compared to the control.

Results

The results are shown in FIG. 3E, FIG. 3F, FIG. 3G and FIG. 3H.

FIGS. 3E-H show the change in fluorescence intensities of all antibody-conjugates in percent of the controls stored for the same length of time under the same conditions.

The stability of the antibody-conjugates in the matrix is reduced compared to the stability of the conjugates in aqueous solution. Unambiguous gating is however still possible in all samples. Adding an antioxidant to the matrix significantly improves the stability of the antibody-conjugates in the matrix to the point where it is comparable to the stability in solution. This is an important property considering the practical use of the ready-to-use reagent Summary All conjugates show sufficient stability in a matrix containing an antioxidant when stored at 2-8° C.

Example 5

4-Color Matrix Reagent

This Example describes the combination of four antibodies in the Matrix and the stability of this reagent Matrix at different temperatures.

Procedure 16 matrices are prepared according to procedure B in Example 1, using a 4-color mix incorporating CD3 RPE-A680, CD4 FITC, CD8 RPE and CD45 APC in a 1:1:1:1 ratio. 8 matrices are made with 100 µL of CytoCount™ beads and 8 with both beads and 20 µL of the 4-color mix.

Preparing the Matrix Samples

Day 0: 4 matrices are analysed (2 of each)

1. 20 µL of the 4-color mix is added to the matrices containing only beads.

2. To all 4 tubes is added 100 µL of whole blood specimen.

3. The samples are vortexed and incubated in the dark for 15 min. at room temperature.

The samples are lysed with Uti-Lyse™ according to procedure D, Example 1.

All samples are vortexed for 5 seconds immediately before analysing. All samples are analysed on a FACSCalibur™ flow cytometer with Cellquest™ software version 3.3 and the median fluorescence intensity of the lymphocytes is found.

The remaining matrices are frozen (−18° C.) for 24 h and thawed for 2 h at 2-8° C. This freeze-thaw cycle is repeated 3 times.

Day 3: 4 matrices are analysed as described above.

The remaining matrices are stored at 37° C. for 24 h in the dark.

Day 4: 4 matrices are analysed as described above.

The remaining matrices are stored at 20° C. for 4 days in the dark.

Day 8: The final 4 matrices are analysed as described above.

Results

The results are shown in FIG. 4.

FIG. 4 shows the fluorescent intensity before (Day 0) and after the freezing and heating (Day 8) for CD3 RPE-A680 and CD4 FITC; comparing in black: Matrix containing beads (4-color mix is added when preparing sample) with in grey: Matrix containing beads and 4-color mix.

The following Table (Table 7) shows median fluorescent intensities expressed in percent of the control of the lymphocytes as it is influenced by freezing and heating (for control of fluorescence intensity is used the Matrix-tubes with beads only, where the 4-color mixture is added when preparing the sample).

TABLE 7

Median fluorescent intensities, as percentages
of controls, determined in Example 5.

|  | CD3 RPE-A680 | CD4 FITC | CD8 RPE | CD45 APC |
|---|---|---|---|---|
| Day 0 | 59 | 89 | 64 | 75 |
| Day 3 (after freezing) | 65 | 95 | 48 | 104 |
| Day 4 (after 37° C.) | 27 | 87 | 20 | 90 |
| Day 8 (after 20° C.) | 14 | 79 | 18 | 63 |

The stability of the antibody-conjugates in the matrix is comparable to the stability of the conjugates in aqueous solution. Stability to some variation in temperature is essential for antibody-conjugates in aqueous solution, since they will be exposed to heating and cooling each time the reagent is used. This demand is not as relevant for the type of ready-to-use reagent described in the claims, since they can be taken out from storage one at a time and used immediately. However, since the reagent may be exposed to some temperature variations during shipping, the observed stability is a great advantage.

Summary

The antibody-conjugates investigated display a stability under varying temperatures that is comparable to their stability in aqueous solution.

Example 6

CD4 Counting in Lysed and Unlysed 3-Colour Matrix Samples Compared to TruCOUNT™/Multitest™ 4-Color Reagent This Example compares CD4 counts and percentages from 18 different whole blood specimens from both lysed and unlysed Matrix samples using a 3-color mixture with CD4 counts obtained using TruCOUNT™ tubes and a MultiTEST™ 4-color reagent.

Procedure 72 matrices are prepared according to procedure B in Example 1, using 15 μL of a 3-color mix incorporating CD3 RPE, CD4 APC and CD45 FITC in a 1:1:1 ratio and 50 μL of CytoCount™ beads.

For each of 18 whole blood specimens, 4 Matrix samples are prepared:

1. To all 4 tubes is added 50 μL of whole blood specimen.
2. The samples are vortexed and incubated in the dark for 15 min. at room temperature.
3. 2 samples are lysed with Uti-Lyse™ according to procedure D, Example 1.
4. The other 2 samples are not lysed, but simply diluted with 0.5 mL PBS.

Furthermore one TruCOUNT™ sample is prepared:

1. To the TruCOUNT™-tube is added 10 μL MultiTEST™ 4-color reagent
2. To the tube is added 50 μL of whole blood specimen.
3. The sample is vortexed and incubated in the dark for 15 min. at room temperature.
4. The sample is lysed with FACS™ Lysing solution according to procedure E, Example 1.

All samples are vortexed for 5 seconds immediately before analysing. All the samples are analysed on a FACSCalibur™ flow cytometer with Cellquest™ version 3.3 or MultiSET™ software and on a Cyan™ ADP flow cytometer with Summit software version 4.1. The CD4-count is obtained as well as the percentage of CD4-positive cells out of the CD3-positive cells.

Results

The results are shown in FIG. 5A, FIG. 5B, FIG. 5C, FIG. 5D, FIG. 5E, FIG. 5F, FIG. 5G, FIG. 5H and FIG. 6.

FIGS. 5A-D show Bland Altman plots of CD4 count obtained with TruCOUNT™/MultiTEST™ compared to lysed and unlysed Matrix samples analysed on both FACSCalibur™ and Cyan™ ADP. The percent similarity is calculated as the average of the CD4 counts from TruCOUNT and Matrix divided by the TruCOUNT™ CD4 count. FIGS. 5E-H show Bland Altman plots of CD4 count obtained when reanalysing the data. The plots show, that the Matrix-tubes generally give counts that are consistent with the counts obtained with the TruCOUNT™-tubes. The CV's are in all cases low.

FIG. 6 shows Bland Altman plots of the CD4 percentages (out of CD3-positive cells) for lysed and unlysed Matrix-samples compared to TruCOUNT™/MultiTEST™, analysed on both FACSCalibur™ and Cyan™ ADP. The percent similarity is calculated as in FIGS. 5A-H above. The plots show, that the CD4 percentages obtained are the same, and the CV's are very low.

TABLE 8

Average, standard deviation and coefficient of variation for
the percent similarities between Matrix and TruCOUNT ™
tubes determined in Example 6.

|  | CD4 counts | | | CD4 percentages | | |
|---|---|---|---|---|---|---|
|  | Average | St. Dev. | CV | Average | St. Dev. | CV |
| Matrix lyse/Calibur ™ | 96.0 | 5.0 | 5.3 | 99.9 | 0.8 | 0.8 |
| Matrix lyse/Cyan ™ | 93.3 | 5.5 | 5.9 | 100.1 | 1.3 | 1.3 |
| Matrix nolyse/Calibur ™ | 95.1 | 3.9 | 4.1 | 99.5 | 1.2 | 1.2 |
| Matrix nolyse/Cyan ™ | 90.6 | 4.9 | 5.4 | 99.6 | 1.3 | 1.3 |

Some small inconsistencies were observed during the analysis of the data. Therefore, the CD4 counts were subsequently reanalysed with a new version of the Summit software (version 4.2) and with optimised gating. This gave the results seen below.

Re-analyzed average, standard deviation and coefficient of variation for the percent similarities between Matrix and TruCOUNT™ tubes determined in Example 6.

|  | CD4 counts | | |
|---|---|---|---|
|  | Average | St. Dev. | CV |
| Matrix lyse/Calibur ™ | 102.1 | 2.9 | 2.8 |
| Matrix lyse/Cyan ™ n | 99.3 | 3.3 | 3.3 |
| Matrix nolyse/Calibur ™ | 96.0 | 3.1 | 3.2 |
| Matrix nolyse/Cyan ™ | 91.5 | 4.6 | 5.1 |

The counts for the Matrix-samples are consistent with the counts obtained with the TruCOUNT™ tubes and the CV's are low. High consistency and low variation are of the outmost importance in absolute counting to ensure that a sample will give the same count and thus the same diagnosis if tested today or tomorrow. It would be possible to adjust the counts to give an even closer match with the counts obtained with the TruCOUNT™ tubes.

Summary

The Matrix-tube counts are consistent with the counts obtained with the TruCOUNT™ tubes, and the CV's are low. The two methods gave the same CD4 percentages with very low CV's.

Example 7

CD4 Counting in Lysed and Unlysed 2-colour Matrix Samples Compared to TruCOUNT™/MultiTEST™ 4-Color Reagent This example compares CD4 counts from 6 different whole blood specimens from both lysed and unlysed Matrix samples using a 2-colour mixture with CD4 counts obtained using TruCOUNT™ tubes and MultiTEST™ 4-color reagent and a 6-colour antibody mixture with CytoCount™ beads added immediately prior to analysis.

Procedure 36 matrices are prepared according to the procedure in Example 1B, using 5 µL of a two-colour mix incorporating CD3-FITC and CD4-RPE in a 1:1 ratio and 50 µL of Cyto-Count™ beads. A 6 colour mixture is prepared with CD3-PB, CD4-FITC, CD8-APC, CD19-RPECy5, CD45-CY and CD56-RPE.

For each of 6 whole blood specimens, 6 Matrix samples are prepared along with 6 CytoCount™ samples:

1. To each of the CytoCount™ samples is added 3 µL 6-colour mixture
2. To all Matrix samples is added 50 µL of whole blood specimen. To the CytoCount™ samples is added 30 µL of whole blood specimen.
3. The samples are vortexed and incubated in the dark for 15 min. at room temperature.
4. 3 samples of each kind are lysed with Uti-Lyse™ according to procedure D, Example 1.
5. The other 3 samples of each kind are not lysed, but simply diluted with 0.5 mL PBS.

Furthermore two TruCOUNT™ samples are prepared:
1. To the TruCOUNT™-tubes are added 10 µL MultiT-EST™ 4-color reagent
2. To the tubes are added 50 µL of whole blood specimen.
3. The sample is vortexed and incubated in the dark for 15 min. at room temperature.
4. The sample is lysed with FACS™ Lysing solution according to procedure E, Example 1.

All samples are vortexed for 5 seconds immediately before analysing. The matrix and CytoCount™ samples are analysed on a Cyan™ ADP flow cytometer with Summit software version 4.2 and the MultiSET™ samples are analysed on a FACSCalibur™ flow cytometer with MultiSET™ software. The absolute count of CD4-positive T-lymphocytes is obtained.

Results

Figure 7:
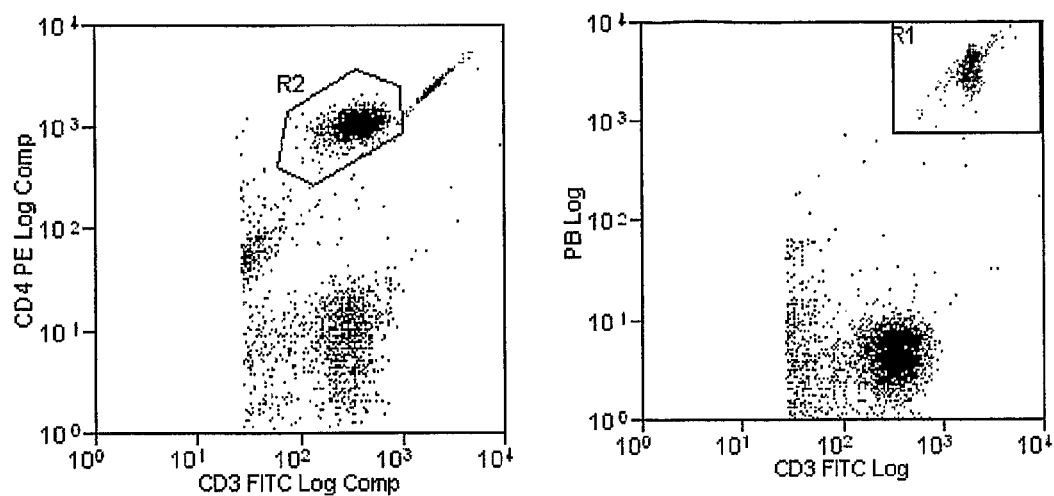
FIG. 7: shows the two fluorescence plots used to gate on cells and beads.
Figure 8:
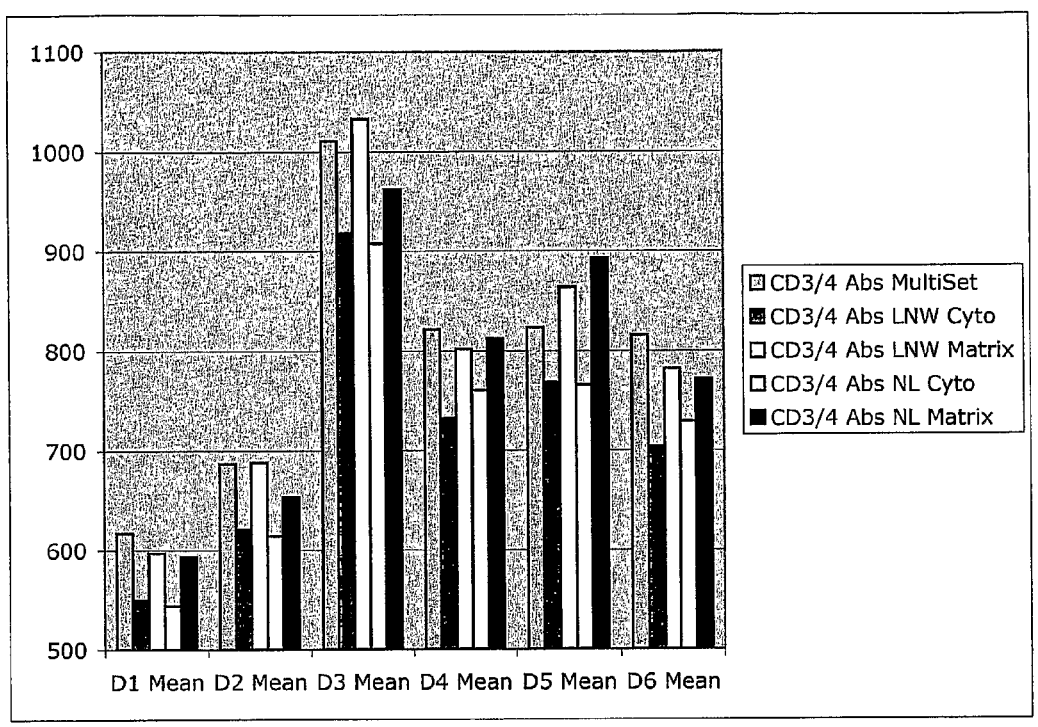
FIG. 8: Compares the counts obtained with TruCOUNT/MultiSET, 6-colout CytoCount™ controls lysed and unlysed and 2-colour Matrix samples lysed and unlysed.

An example of the plots used to calculate the CD4-count in the matrix samples is shown in FIG. 7. The CD4-counts are shown in FIG. 8.

FIG. 7 shows a dot plot of CD3-FITC vs. CD4-RPE, and CD3-FITC vs. Violet 1. The beads are gated in R1 and the CD4-positive cells in R2. The cell-count is defined as events in R2 that are not in R1. FIG. 8 shows the comparison of the CD4-counts from the 6 donors.

Summary

With this method we also find that the Matrix-tube counts are consistent with the counts obtained with the Tru-COUNT™ tubes, in fact the absolute counts from the Matrix tubes are closer to the TruCOUNT results than the results obtained with the CytoCount beads used in the standard way.

Example 8

CD4 Counting in Unlysed 6-colour Matrix Samples Compared to TruCOUNT™/MultiTEST™ 4-Color Reagent This example compares CD4 counts from 5 different whole blood specimens from unlysed Matrix samples using a 6-colour mixture with CD4 counts obtained using TruCOUNT™ tubes and MultiTEST™ 4-color reagent and a 6-colour antibody mixture with CytoCount beads added immediately prior to analysis.

Procedure

A 6-colour mixture is prepared with CD3-PB, CD4-FITC, CD8-APC, CD19-RPECy5, CD45-CY and CD56-RPE. 10 matrices are prepared according to the procedure in Example 1B, using 3 µL of the 6-colour mix and 30 µL of CytoCount™ beads.

For each of 5 whole blood specimens, 6 Matrix samples are prepared along with 15 CytoCount samples:

1. To each of the CytoCount samples is added 3 µL 6-colour mixture
2. To all samples is added 30 µL of whole blood specimen.
3. The samples are vortexed and incubated in the dark for 15 min. at room temperature.
4. 3 CytoCount™ samples of are lysed with Uti-Lyse™ according to procedure D, Example 1.
5. The other 3 CytoCount™ samples along with the matrix samples are not lysed, but simply diluted with 0.5 mL PBS.

Furthermore two TruCOUNT™ samples are prepared:
1. To the TruCOUNT™-tubes are added 10 µL MultiT-EST™ 4-color reagent
2. To the tubes are added 50 µL of whole blood specimen.
3. The sample is vortexed and incubated in the dark for 15 min. at room temperature.
4. The sample is lysed with FACS™ Lysing solution according to procedure E, Example 1.

All samples are vortexed for 5 seconds immediately before analysing. The matrix and CytoCount™ samples are analysed on a Cyan™ ADP flow cytometer with Summit software version 4.2 and the MultiSET samples are analysed on a FACSCalibur™ flow cytometer with MultiSET™ software. The absolute count of CD4-positive T-lymphocytes is obtained.

Results

Figure 9:
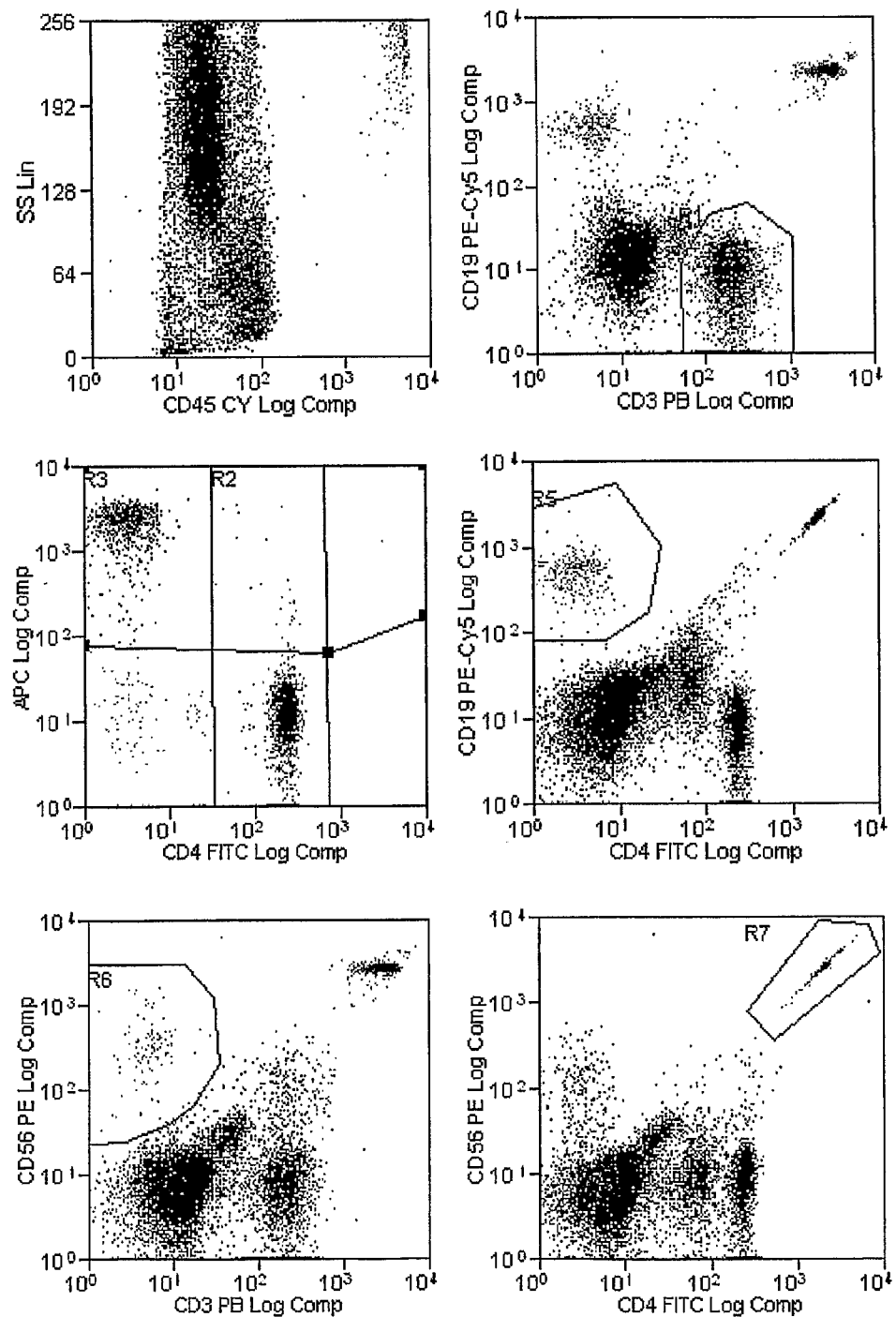
FIG. 9: An example of the plots used to calculate the CD4-count in the matrix samples.
Figure 10:
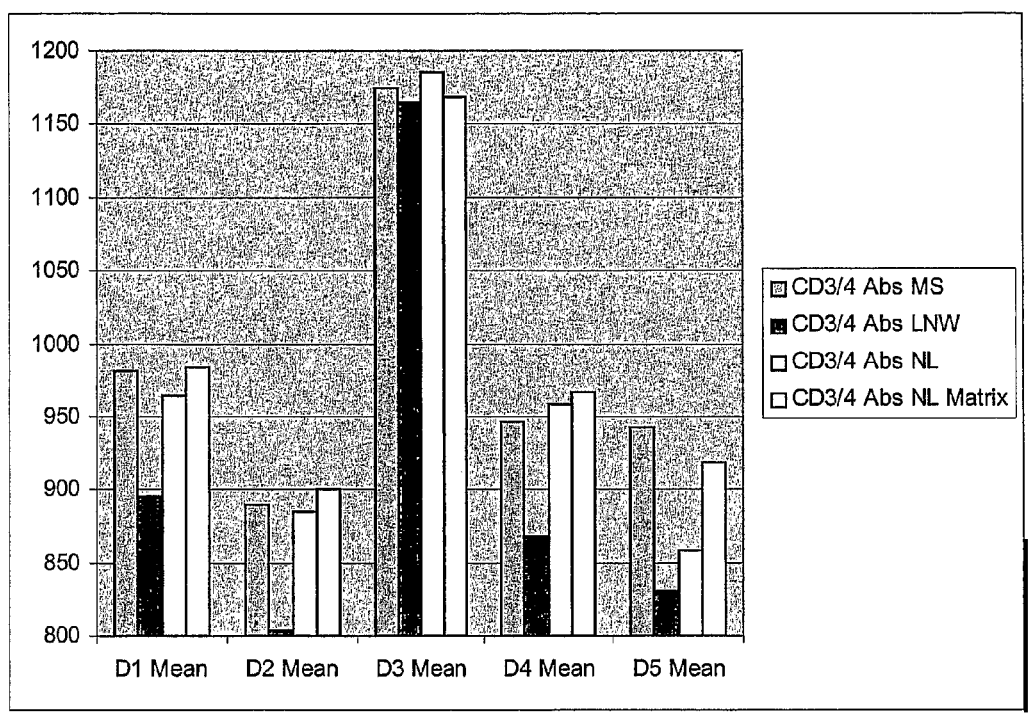
FIG. 10: Comparison of the CD4 counts obtained with 6-colour matrix and CytoCount™ and TruCOUNT.

FIG. 9 is an example of the plots used to calculate the CD4-count in the matrix samples. The threshold is set on CD45-CY. The T-lymphocytes are gated in CD19-RPECY5 vs. CD3-PB and divided into subpopulations in CD8-APC vs. CD4-FITC. The B-cells are gated in CD19-RPECY5 vs. CD4-FITC and the NK-cells are gated in CD56-RPE vs. CD3-PB. Finally the beads are gated in CD56-RPE vs. CD4-FITC. FIG. 10 Comparison of the CD4 counts obtained with matrix, CytoCount and TruCOUNT.

Summary

This method has the advantage that in addition to the CD4-count it is possible to obtain other information concerning the patient's condition. The counts are consistent with the results obtained with TruCOUNT.

Example 9

CD34 Counting in Unlysed 2-Colour Matrix Samples in Stabilized Whole Blood

This example compares the CD34 count of two stabilized whole blood specimen from UK-NEQAS obtained with unlysed 2-colour matrix samples and an unlysed control samples using CytoCount™ beads.

Procedure

A 2-colour mixture is prepared with CD34-RPE and CD45-FITC. 2 matrices are prepared according to the procedure in Example 1B, using 5 μL of the 2-colour mix and 50 μL of CytoCount™ beads.

For each stabilized whole blood specimen, one matrix sample is prepared along with one CytoCount sample:
1. To the CytoCount samples is added 5 μL 2-colour mixture
2. To all samples is added 50 μL of stabilized whole blood specimen.
3. The samples are vortexed and incubated in the dark for 15 min. at room temperature.
4. The samples are not lysed, but simply diluted with 0.5 mL PBS.

All samples are vortexed for 5 seconds immediately before analysing. The samples are analysed on a Cyan™ ADP flow cytometer with Summit software version 4.2. The absolute count of CD34-positive cells is obtained using the ISHAGE gating strategy.

Results

Figure 11A:
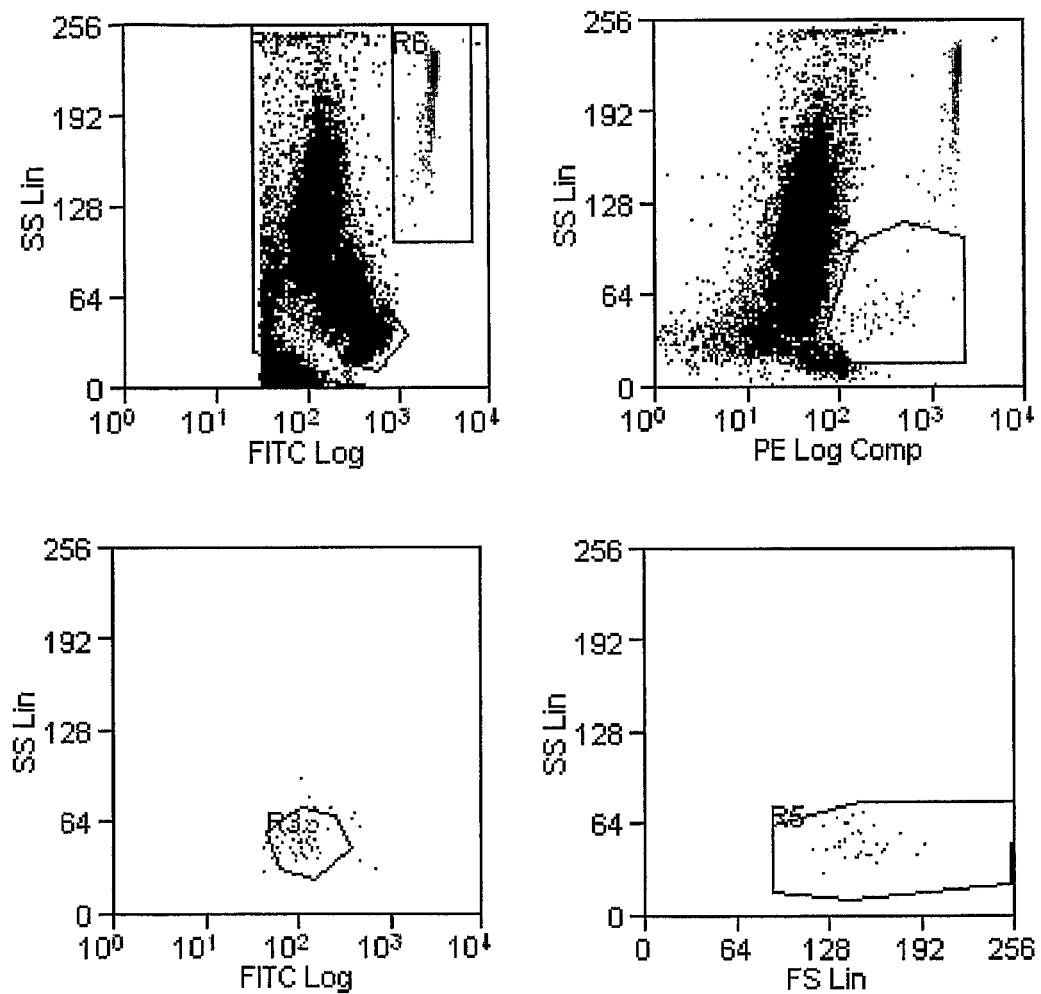
FIG. 11A control, FIG. 11B matrix.
Figure 11B:
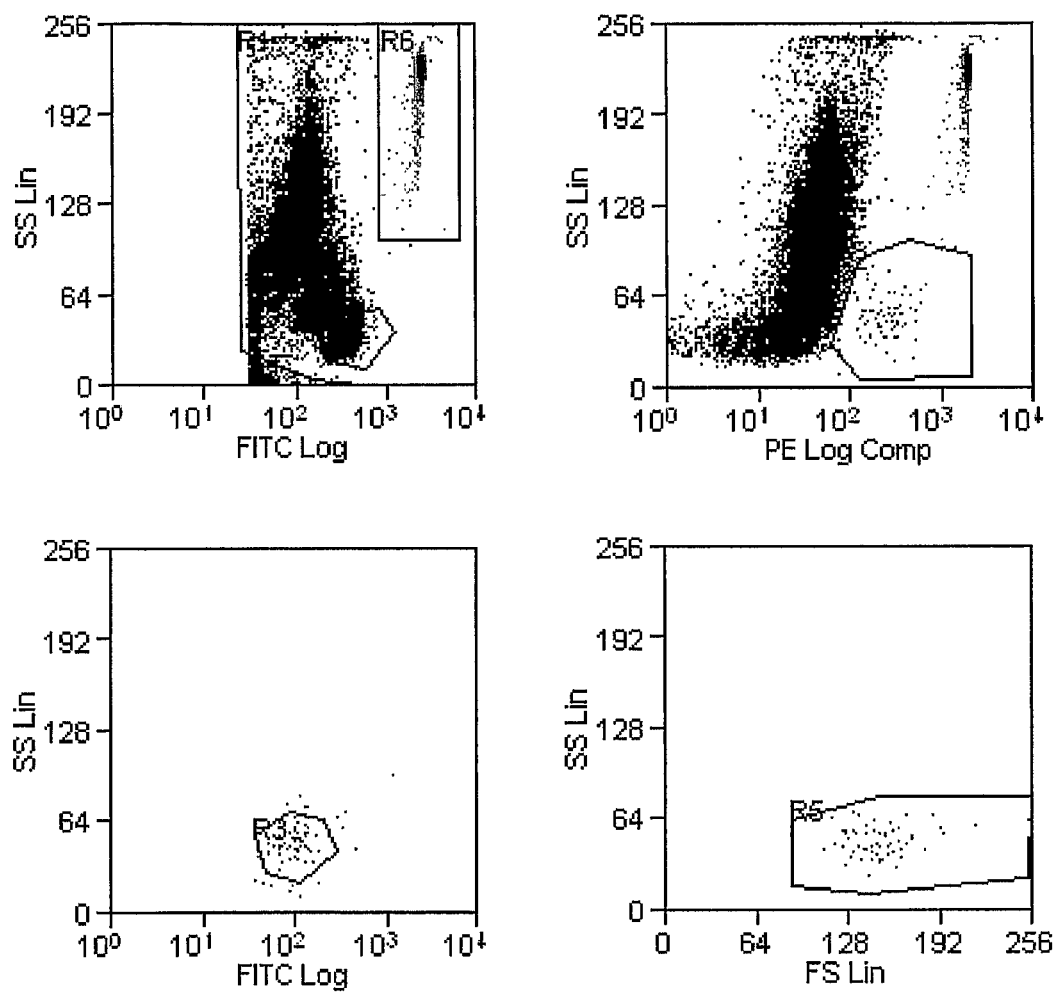
FIG. 11: Comparison of the plots for CD34 counting obtained with matrix and control samples.

FIG. 11 Comparison of the plots obtained with matrix and control samples. All cells except erythrocytes are selected in the SSC vs. CD45-FITC plot. This gate is set on the SSC vs. CD34-RPE plot, where the CD34-positive cells are gated. In the SSC vs. CD45-FITC plot below, the cluster of cells is selected and in the SSC vs. FSC plot it is verified that the cells are in the same area as the lymphocytes. FIG. 11A control, FIG. 11B matrix.

TABLE 10

Comparison of CD34 counts determined in Example 9

| Sample | Control count | Matrix count | NEQAS count |
|---|---|---|---|
| 0502 #94 | 62.2 | 62.8 | 61.09 |
| 0504 #98 | 14.2 | 12.5 | 13.05 |

Summary

The matrix samples give plots that are indistinguishable from the controls and the counts obtained are very close to the counts determined by UK-NEQAS.

Example 10

Staining of an Intercellular Target Using Matrix-Tubes

This example verifies that it is also possible to stain intercellular markers using the matrix-technology.

Procedure 1 matrix is prepared according to the procedure in Example 1B, using 3 μL anti-myeloperoxidase (MPO) and 1 using 3 μL of a negative control antibody.

Two samples of whole blood are prepared with IntraStain:
1. 100 μL of whole blood are added to each of two tubes.
2. To both samples is added 200 μL of IntraStain reagent A. The tubes are vortexed and incubated at room temperature for 15 min.
3. 2 mL of PBS is added to each tube. The tubes are centrifuged and the supernatant is aspirated leaving approximately 50 μL of fluid.
4. To each tube is added 200 μL of IntraStain reagent B.
5. From these tubes are pipetted 100 μL of cell-suspension to the matrix-tubes and to two control tubes containing 3 μL of anti-MPO and the negative control antibody, respectively.
6. All tubes are vortexed and incubated in the dark for 15 min at room temperature.
7. 2 mL of PBS is added to each tube. The tubes are centrifuged and the supernatant is aspirated leaving approximately 50 μL of fluid.
8. The cells are resuspended in 0.4 mL PBS All samples are vortexed for 5 seconds immediately before analysing. The samples are analysed on a Cyan™ ADP flow cytometer with Summit software version 4.2.

Results

Figure 12A:
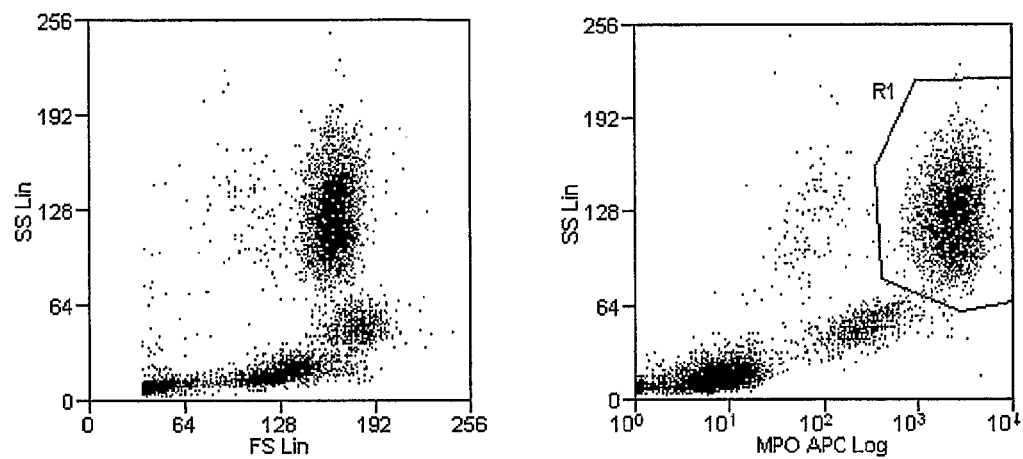
FIG. 12A control, FIG. 12B matrix.
Figure 12B:
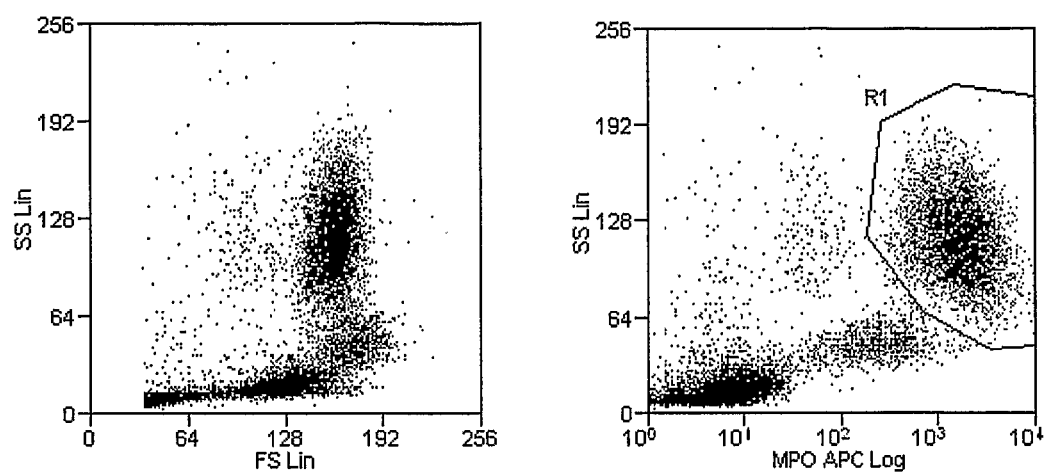
FIG. 12.

FIG. 12 Comparison of the plots obtained with anti-myeloperoxidase in solution and embedded in a matrix. The first plot displays the FSC vs. SSC and the second shows anti-MPO-APC vs. SSC, where the positive granulocytes can be gated. FIG. 12A control, FIG. 12B matrix.

Summary

The matrix samples give plots that are very similar to the controls and the negative controls show no unspecific binding in either matrix or control samples.

REFERENCES

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method for determining the absolute counts of cells of interest per unit volume of a sample, said method comprising:
    (a) providing a container containing:
        (i) a matrix adhered to at least one wall of said container, said matrix being semi-solid, of gel-like consistency, or in dry form;
        (ii) a predetermined quantity of reference microparticles, distinguishable from a labeled cell-binding agent, disposed in or on said matrix such that substantially all the reference microparticles are thereby attached to said container; and (iii) the labeled cell-binding agent in or on the matrix, wherein the labeled cell-binding agent is capable of binding to and identifying said cells of interest in the sample;

(b) adding a known sample volume of said sample to said container, whereby:
(i) said known sample volume, labeled cell binding agent, and matrix are mixed;
(ii) said labeled cell-binding agent binds to cells of interest are in said known sample volume; and
(iii) said reference microparticles are released into the added known sample volume;

(c) counting, in a portion of the sample volume obtained in (b), both the number of said cells of interest identified as cells bound to said labeled cell-binding agent and the number of reference microparticles, and from this determining the ratio of said cells of interest per reference microparticles in said portion of the sample volume; and (d) determining an absolute count of said cells of interest in said known sample volume by multiplying the ratio of cells of interest per reference microparticle obtained in (c) by the predetermined quantity of reference microparticles in said known sample volume.

2. The method according to claim 1, in which said matrix retains substantially all said reference microparticles in or on said container during routine handling of said container.

3. The method according to claim 1, in which said matrix retains substantially all said reference microparticles in or on said container when said container is inverted.

4. The method according to claim 1 in which said matrix is the only means for retaining said reference microparticles in or on said container.

5. The method according to claim 1, in which said matrix comprises a carbohydrate.

6. The method according to claim 1, in which said matrix comprises a sugar, a mixture of sugars, a polymer, or a protein.

7. The method according to claim 1, in which said matrix comprises a 1:2, 1:1, or 2:1 mixture of any two components chosen from the group consisting of fructose, trehalose, and raffinose.

8. The method according to claim 1, in which said matrix is present at a quantity of less than 5 mg.

9. The method according to claim 1, in which said matrix comprises an antioxidant.

10. The method according to claim 1, in which substantially all said reference microparticles are released from said at least one wall of said container into said quantity known sample volume of said sample on addition of said known sample volume of said sample to said container.

11. The method according to claim 1, in which substantially all said reference microparticles are discrete when counted.

12. The method according to claim 1, in which said counting in (c) comprises the step of counting said cells of interest and said reference microparticles in a flow cytometer.

13. The method according to claim 1, in which said cells of interest comprise microorganisms.

14. The method according to claim 13, in which said microorganisms comprise yeast or bacteria.

15. The method according to claim 1, in which said cells of interest comprise lymphocytes and said sample comprises unlysed whole blood.

16. The method according to claim 1, in which said labeled cell-binding agent comprises an antibody capable of binding to an antigen selected from the group consisting of: CD2, CD3, CD4, CD5, CD7, CD8, CD10, CD13, CD14, CD15, CD16, CD19, CD20, CD22, CD33, CD34, CD38, CD45, CD56, CD57, CD64, CDw65, CD117, and CD133.

17. The method according to claim 1, in which said reference microparticles are chosen from the group consisting of polystyrene beads, latex beads, agarose beads, and acrylamide beads.

18. The method according to claim 1, in which (c) comprises the step of individually detecting said reference microparticles and said labeled cell-binding agent by virtue of a signal-generating means.

19. The method according to claim 18, in which said signal generating means comprises a fluorochrome selected from the group consisting of: fluorescein isothiocyanate (FITC), phycoerythrin (PE), PE-Cy5, PE-Cy5.5, PE-Cy7, PE-A680, PE-TR (TEXAS RED), allophycocyanin (APC), APC-Cy7, PACIFIC BLUE, CASCADE YELLOW, ALEXA dyes, coumarins, and Q-DOTS.

20. The method according to claim 19, in which said reference microparticles and said labeled cell-binding agent are labeled with different fluorochromes.

21. The method according to claim 1, in which said container contains more than one labeled cell-binding agent.

22. The method according to claim 1, in which said labeled cell-binding agent comprises an anti-CD3 antibody coupled to phycoerythrin and in which the container contains a second labeled cell-binding agent comprising an anti-CD4 antibody coupled to APC and a third labeled cell-binding agent comprising an anti-CD45 antibody coupled to FITC.

23. The method according to claim 1, in which said cell-binding agent comprises an anti-CD34 antibody coupled to phycoerythrin and in which the container contains a second labeled cell-binding agent comprising an anti-CD45 antibody coupled to FITC or APC.

24. The method according to claim 1, in which the container contains propidium iodide and TWEEN.

25. The method according to claim 1, in which the container is disposable.

26. An apparatus for preparing a sample for absolute counting of cells of interest in said sample, said apparatus comprising:
(a) a container;
(b) a matrix adhered to at least one wall of said container, said matrix being semi-solid, of gel-like consistency, or in dry form;
(c) a predetermined quantity of reference distinguishably distinct microparticles disposed on or in said matrix such that substantially all said reference microparticles are thereby attached to said container; and
(d) a labeled cell-binding agent in or on the matrix, in which said matrix is configured to release said reference microparticles into said sample upon addition of a known volume of said sample to said container.

27. A kit for preparing a sample for determining the absolute counts of cells of interest in said sample comprising:
(a) an apparatus comprising:
(i) a container;
(ii) a matrix adhered to at least one wall of said container, said matrix being semi-solid, of gel-like consistency, or in dry form;
(iii) a predetermined quantity of reference distinguishably distinct microparticles disposed on or in said matrix such that substantially all said reference microparticles are thereby attached to said container; and
(iv) a labeled cell-binding agent; in or on said matrix, in which said matrix is configured to release said reference microparticles into said sample upon addition of said sample to said container; and (b) instructions for adding incubating, and mixing said sample in said apparatus.

28. The kit according to claim 27, in which said cells of interest comprise CD3+ and CD4+ cells.

29. The kit according to claim 27, wherein the labeled cell-binding agent is of a type that binds to and enables determining of said absolute counts of cells of interest present in a sample.

* * * * *